US012091681B2

(12) United States Patent
Manting et al.

(10) Patent No.: US 12,091,681 B2
(45) Date of Patent: Sep. 17, 2024

(54) EX VIVO USE OF MODIFIED CELLS OF LEUKEMIC ORIGIN FOR ENHANCING THE EFFICACY OF ADOPTIVE CELL THERAPY

(71) Applicant: MENDUS B.V., Leiden (NL)

(72) Inventors: Erik Hans Manting, Leiden (NL); Jeroen Rovers, Leiden (NL); Satwinder Kaur Singh, Leiden (NL)

(73) Assignee: MENDUS B.V., Leiden (NL)

( * ) Notice: Subject to any disclaimer, the term of this patent is extended or adjusted under 35 U.S.C. 154(b) by 327 days.

(21) Appl. No.: 17/213,461

(22) Filed: Mar. 26, 2021

(65) Prior Publication Data

US 2021/0324332 A1 Oct. 21, 2021

Related U.S. Application Data

(60) Provisional application No. 63/110,003, filed on Nov. 5, 2020, provisional application No. 63/001,189, filed on Mar. 27, 2020.

(51) Int. Cl.
*C12N 5/0783* (2010.01)
*A61K 35/17* (2015.01)
*A61P 35/00* (2006.01)
*C12N 5/0784* (2010.01)

(52) U.S. Cl.
CPC ............ *C12N 5/0636* (2013.01); *A61K 35/17* (2013.01); *A61P 35/00* (2018.01); *C12N 5/0639* (2013.01)

(58) Field of Classification Search
None
See application file for complete search history.

(56) References Cited

U.S. PATENT DOCUMENTS 4,690,915 A 9/1987 Rosenberg
4,797,368 A 1/1989 Carter et al.
4,956,778 A 9/1990 Naito
5,091,513 A 2/1992 Huston et al.
5,132,405 A 7/1992 Huston et al.
5,139,941 A 8/1992 Muzyczka et al.
5,858,358 A 1/1999 June et al.
5,876,989 A 3/1999 Berg et al.
5,883,223 A 3/1999 Gray
5,993,434 A 11/1999 Dev et al.
5,994,136 A 11/1999 Naldini et al.
6,013,516 A 1/2000 Verma et al.
6,054,297 A 4/2000 Carter et al.
6,080,840 A 6/2000 Slanetz et al.
6,181,964 B1 1/2001 Hofmann et al.
6,207,156 B1 3/2001 Kuchroo et al.
6,233,482 B1 5/2001 Hofmann et al.
6,516,223 B2 2/2003 Hofmann
6,534,055 B1 3/2003 June et al.
6,567,694 B2 5/2003 Hayakawa
6,582,959 B2 6/2003 Kim
6,678,556 B1 1/2004 Nolan et al.
6,680,301 B2 1/2004 Berg et al.
6,692,964 B1 2/2004 June et al.
6,703,020 B1 3/2004 Thorpe et al.
6,797,514 B2 9/2004 Berenson et al.
6,867,041 B2 3/2005 Berenson et al.
6,884,879 B1 4/2005 Baca et al.
6,887,466 B2 5/2005 June et al.
6,905,680 B2 6/2005 June et al.
6,905,681 B1 6/2005 June et al.
6,905,874 B2 6/2005 Berenson et al.
7,060,269 B1 6/2006 Baca et al.
7,067,318 B2 6/2006 June et al.
7,144,575 B2 12/2006 June et al.
7,171,264 B1 1/2007 Hofmann et al.
7,172,869 B2 2/2007 June et al.
7,173,116 B2 2/2007 Fewell et al.
7,175,843 B2 2/2007 June et al.
7,232,566 B2 6/2007 June et al.
7,569,664 B2 8/2009 Jakobsen et al.
7,700,546 B2 4/2010 Mekada et al.
7,754,482 B2 7/2010 Riley et al.
8,008,449 B2 8/2011 Korman et al.
8,017,114 B2 9/2011 Korman et al.
8,119,129 B2 2/2012 Jure-Kunkel et al.
8,354,509 B2 1/2013 Carven et al.
8,440,431 B2 5/2013 Voytas et al.
8,440,432 B2 5/2013 Voytas et al.
8,450,471 B2 5/2013 Voytas et al.
8,507,443 B2 8/2013 Mekada et al.
8,586,363 B2 11/2013 Voytas et al.
8,697,853 B2 4/2014 Voytas et al.
8,722,400 B2 5/2014 Riley et al.
8,735,553 B1 5/2014 Li et al.
(Continued)

FOREIGN PATENT DOCUMENTS

CA 3104833 A1 1/2020
EP 0666868 B1 4/2002
EP 1894575 B1 2/2013
EP 2743344 A1 6/2014
EP 2931878 B1 11/2016
WO WO 1994/010202 A1 5/1994
WO WO 1996/007432 A1 3/1996
WO WO 1996/013593 A2 5/1996
WO WO 1996/018105 A1 6/1996
WO WO 1996/030046 A1 10/1996
WO WO 1996/040200 A1 12/1996
WO WO 1997/027873 A1 8/1997
WO WO 1998/042752 A1 10/1998
WO WO 1998/045332 A2 10/1998
WO WO 1998/054311 A1 12/1998
(Continued)

OTHER PUBLICATIONS

Trivedi, 2005, Blood, vol. 105: 2793-2801.*
(Continued)

*Primary Examiner* — Amy E Juedes
(74) *Attorney, Agent, or Firm* — LATHROP GPM LLP; James H. Velema, Esq.; Judith L. Stone-Hulslander

(57) ABSTRACT

The present disclosure provides ex vivo methods which employ modified cells of leukemic origin to enhance the efficacy of adoptive cell therapy.

30 Claims, 19 Drawing Sheets

(56) References Cited

U.S. PATENT DOCUMENTS 8,771,985 B2 7/2014 Cui et al.
9,187,758 B2 11/2015 Cai et al.
9,206,404 B2 12/2015 Cui et al.
9,393,257 B2 7/2016 Osborn et al.
9,555,105 B2 1/2017 Riley et al.
9,855,298 B2 1/2018 Bot et al.
10,064,923 B2 9/2018 Van Wetering et al.
10,513,686 B2 12/2019 Ostertag et al.
11,027,001 B2 6/2021 Van Wetering et al.
2003/0170238 A1 9/2003 Gruenberg et al.
2003/0190317 A1 10/2003 Baca et al.
2003/0203409 A1 10/2003 Kim
2003/0206899 A1 11/2003 Ferrara et al.
2004/0014645 A1 1/2004 Draghia-Akli et al.
2004/0057935 A1 3/2004 Yu et al.
2004/0059285 A1 3/2004 Mathiesen et al.
2004/0092907 A1 5/2004 Mathiesen et al.
2005/0052630 A1 3/2005 Smith et al.
2005/0070841 A1 3/2005 Mathiesen et al.
2005/0075308 A1 4/2005 Wilson et al.
2005/0112126 A1 5/2005 Baca et al.
2005/0186208 A1 8/2005 Fyfe et al.
2005/0196754 A1 9/2005 Drmanac et al.
2006/0009360 A1 1/2006 Pifer et al.
2006/0121005 A1 6/2006 Berenson et al.
2007/0041954 A1 2/2007 Ichim
2007/0128708 A1 6/2007 Gamelin
2012/0294796 A1 11/2012 Johnson et al.
2013/0274134 A1 10/2013 Lindstedt et al.
2013/0330399 A1 12/2013 Reisfeld et al.
2015/0166955 A1 6/2015 Van Wetering et al.
2015/0297698 A1 10/2015 Van Wetering et al.
2018/0002397 A1 1/2018 Shah et al.
2018/0236054 A1 8/2018 Sampson et al.
2019/0000945 A1 1/2019 Van Wetering et al.
2019/0055297 A1 2/2019 Zhao et al.
2019/0134091 A1 5/2019 Dropulic et al.
2019/0151363 A1* 5/2019 Brentjens .............. A61K 35/17
2019/0263908 A1 8/2019 Van Der Vliet et al.

FOREIGN PATENT DOCUMENTS

WO WO 1999/018129 A1 4/1999
WO WO 1999/040940 A1 8/1999
WO WO 2000/037504 A2 6/2000
WO WO 2000/054708 A1 9/2000
WO WO 2000/054802 A2 9/2000
WO WO 2001/014424 A2 3/2001
WO WO 2001/018636 A1 3/2001
WO WO 2001/049317 A2 7/2001
WO WO 2001/093897 A2 12/2001
WO WO 2002/023994 A1 3/2002
WO WO 2002/044395 A1 6/2002
WO WO 2002/044396 A1 6/2002
WO WO 2002/092784 A2 11/2002
WO WO 2003/020309 A2 3/2003
WO WO 2004/033685 A1 4/2004
WO WO 2005/012359 A2 2/2005
WO WO 2005/026318 A2 3/2005
WO WO 2005/040220 A1 5/2005
WO WO 2005/044853 A2 5/2005
WO WO 2005/044857 A1 5/2005
WO WO 2006/000830 A2 1/2006
WO WO 2006/037960 A2 4/2006
WO WO 2006/121168 A1 11/2006
WO WO 2007/011693 A2 1/2007
WO WO 2008/119567 A2 10/2008
WO WO 2009/019320 A2 2/2009
WO WO 2009/034172 A1 3/2009
WO WO 2009/046541 A1 4/2009
WO WO 2009/101611 A1 8/2009
WO WO 2009/114335 A2 9/2009
WO WO 2009/127988 A1 10/2009
WO WO 2010/037838 A2 4/2010
WO WO 2010/070047 A1 6/2010
WO WO 2011/018636 A2 2/2011
WO WO 2011/044186 A1 4/2011
WO WO 2011/143624 A2 11/2011
WO WO 2012/056236 A2 5/2012
WO WO 2012/136824 A1 10/2012
WO WO 2012/145493 A1 10/2012
WO WO-2012140130 A1 * 10/2012 ............ A61K 35/17
WO WO 2012/170250 A1 12/2012
WO WO 2013/025779 A1 2/2013
WO WO 2013/026833 A1 2/2013
WO WO 2013/026837 A1 2/2013
WO WO 2013/067492 A1 5/2013
WO WO 2013/109752 A1 7/2013
WO WO 2013/119714 A1 8/2013
WO WO 2013/126794 A1 8/2013
WO WO 2013/181634 A2 12/2013
WO WO 2014/006058 A1 1/2014
WO WO 2014/087010 A1 6/2014
WO WO 2014/087248 A2 6/2014
WO WO 2014/090795 A1 6/2014
WO WO 2014/138314 A1 9/2014
WO WO 2014/179664 A2 11/2014
WO WO-2014186469 A2 * 11/2014 ............ A61K 35/17
WO WO 2014/191525 A1 12/2014
WO WO 2014/194302 A2 12/2014
WO WO 2015/035606 A1 3/2015
WO WO 2015/073801 A1 5/2015
WO WO 2015/085847 A1 6/2015
WO WO 2015/112800 A1 7/2015
WO WO 2015/112900 A1 7/2015
WO WO 2015/191861 A1 12/2015
WO WO 2016/022971 A1 2/2016
WO WO 2016/023040 A1 2/2016
WO WO 2016/024021 A1 2/2016
WO WO 2016/081423 A1 5/2016
WO WO 2016/109415 A1 7/2016
WO WO 2016/141328 A2 9/2016
WO WO 2016/149201 A2 9/2016
WO WO 2016/154628 A1 9/2016
WO WO 2016/176164 A1 11/2016
WO WO 2016/188449 A1 12/2016
WO WO 2017/027422 A1 2/2017
WO WO 2017/049251 A2 3/2017
WO WO 2017/053423 A1 3/2017
WO WO 2017/112797 A1 6/2017
WO WO 2017/121771 A1 7/2017
WO WO 2017/134140 A1 8/2017
WO WO 2017/180519 A1 10/2017
WO WO 2017/194634 A1 11/2017
WO WO 2017/196793 A1 11/2017
WO WO 2017/215585 A1 12/2017
WO WO 2018/017020 A1 1/2018
WO WO 2018/075813 A1 4/2018
WO WO 2018/075857 A1 4/2018
WO WO 2018/075960 A1 4/2018
WO WO 2018/089508 A2 5/2018
WO WO 2018/095428 A1 5/2018
WO WO 2018/137705 A1 8/2018
WO WO 2018/233575 A1 12/2018
WO WO 2019/027903 A1 2/2019
WO WO 2019/034895 A1 2/2019
WO WO 2019/042119 A1 3/2019
WO WO 2019/042285 A1 3/2019
WO WO 2019/042470 A1 3/2019
WO WO 2019/046815 A1 3/2019
WO WO 2019/075385 A1 4/2019
WO WO 2019/086573 A1 5/2019
WO WO 2019/108733 A2 6/2019
WO WO 2019/138367 A1 7/2019
WO WO 2019/144895 A1 8/2019
WO WO 2019/157843 A1 8/2019
WO WO 2019/173636 A1 9/2019
WO WO 2019/179366 A1 9/2019
WO WO 2019/184912 A1 10/2019
WO WO 2019/185717 A1 10/2019
WO WO 2019/201236 A1 10/2019
WO WO 2019/238012 A1 12/2019
WO WO 2019/241732 A1 12/2019
WO WO 2020/009725 A1 1/2020

(56) References Cited

FOREIGN PATENT DOCUMENTS

| | | | |
|---|---|---|---|
| WO | WO 2020/014366 | A1 | 1/2020 |
| WO | WO 2020/017962 | A1 | 1/2020 |
| WO | WO 2020/019135 | A1 | 1/2020 |
| WO | WO 2020/036977 | A1 | 2/2020 |
| WO | WO 2020/043188 | A1 | 3/2020 |
| WO | WO 2020/217226 | A1 | 10/2020 |

OTHER PUBLICATIONS

Welte et al., "Purification and biochemical characterization of human pluripotent hematopoietic colony-stimulating factor", PNAS 82: 1526-30, 1985.*

Aerts-Toegaert et al., "CD83 expression on dendritic cells and T cells: Correlation with effective immune responses", European Journal of Immunology, 37:686-695, 2007.

Agarwal et al., In Vivo Generation of CAR T Cells Selectively in Human CD4+ Lymphocytes Molecular Therapy 28(8):1783-1794 (2020).

Alemany, "Oncolytic Adenoviruses in Cancer Treatment", Biomedicines 2:36-49, 2014.

Alibakhshi et al., "Targeted cancer therapy through antibody fragments-decorated nanomedicines", J Control Release, 2017, 268: 323-334.

Alvey et al., "SIRPA-Inhibited, Marrow-Derived Macrophages Engorge, Accumulate, and Differentiate in Antibody-Targeted Regression of Solid Tumors", Current Biology, 27(14):2065-207, 2017.

Amir et al., "PRAME-Specific Allo-HLA-Restricted T Cells with Potent Antitumor Reactivity Useful for Therapeutic T-Cell Receptor Gene Transfer", Clinical Cancer Research, 17(17):5615-5625, 2011.

Andtbacka et al., "Talimogene Laherparepvec Improves Durable Response Rate in Patients With Advanced Melanoma", Journal of Clinical Oncology, 2015, 22(25):2780-2788.

Anguille et al., "Dendritic cell vaccination as postremission treatment to prevent or delay relapse in acute myeloid leukemia", Blood, Oct. 2017, 130(15): 1713-1721.

Awate et al., "Mechanisms of action of adjuvants", Frontiers in Immunology, 4(114):1-10 (2013).

Baars et al., "Skin tests predict survival after autologous tumor cell vaccination in metastatic melanoma: Experience in 81 patients", Annals of Oncology, 11(8):965-970, 2000.

Bell et al., "Crystal structure of nucleotide-free diphtheria toxin", Biochemistry, 1997, 36(3): 481-488.

Bender et al., "Inactivated Influenza Virus, when Presented on Dendritic Cells, Elicits Human CD8+ Cytolytic T Cell Responses", J. Exp. Med. 182:1663-1671 (1995).

Bengala, et al., Mobilization; Collection, and Characterization of Peripheral Blood Hemopoietic Progenitors after Chemotherapy with Epirubicin, Paclitaxel, and Granulocyte-Colony Stimulating Factor Administered to Patients with Metastatic Breast Carcinoma; Cancer; Mar. 1, 1998; vol. 82; No. 5; pp. 867-873.

Bennett et al., "Help for cytotoxic-T-cell responses is mediated by CD40 signalling", Nature, 393:478-480 (1998).

Bergmann et al., "An endogenously synthesized decamer peptide efficiently primes cytotoxic T cells specific for the HIV-1 envelope glycoprotein", Eur J Immunol., 1993, 23(11): 2777-2781.

Bernhard et al., Generation of Immunostimulatory Dendritic Cells from Human CD34+ Hematopoietic Progenitor Cells of the Bone Marrow and Peripheral Blood, Cancer Research, 1995, pp. 1099-1104, vol. 55.

Bhaya et al., "CRISPR-Cas Systems in Bacteria and Archaea: Versatile Small RNAs for Adaptive Defense and Regulation", Annual Review Genetics, 45:273-297, 2011.

Bikard et al., "Programmable repression and activation of bacterial gene expression using an engineered CRISPR-Cas system", Nucleic Acids Research, 41(15):7429-7437, 2013.

Bommareddy et al., "Integrating oncolytic viruses in combination cancer immunotherapy", Nature Reviews Immunology, 2018, 18: 498-513.

Brocks et al., "A TNF receptor antagonistic scFv, which is not secreted in mammalian cells, is expressed as a soluble mono- and bivalent scFv derivative in insect cells", Immunotechnology 3(3):173-184 (1997).

Burdek et al., "Three-day dendritic cells for vaccine development: Antigen uptake, processing and presentation", Journal of Translational Medicine, 8(90):1-13, 2010.

Buzzi et al., "Cancer immunity after treatment of Ehrlich tumor with diphtheria toxin", Cancer Res., Dec. 1974, 34(12): 3481-3486.

Buzzi et al., "CRM197: Effects of intravenous administration to advanced cancer patients", Cancer Res., Apr. 2004, 64(7 Supplement): 878.

Buzzi et al., "Diphtheria toxin in cancer therapy", The Lancet, 1974, 1(7858): 628-629.

Buzzi, "Diphtheria toxin treatment of human advanced cancer", Cancer Res., 1982, 42(5): 2054-2058.

Buzzi, et al., "CRM197 (nontoxic diphtheria toxin): effects on advanced cancer patients", Cancer Immunol. Immunother., 2004, 53: 1041-1048 (2004).

Buzzi, et al., "CRM197 and cancer: Effects of intratumoral administration", Therapy, Sep. 2004, 1(1): 61-66.

Buzzi, et al., "CRM197; Effects of intravenous administration to advanced cancer patients", American Association for Cancer Research, 2004, 64(7), Supplement.

Cermak et al., "Efficient design and assembly of custom TALEN and other TAL effector-based constructs for DNA targeting", Nucleic Acids Research, 39(12):e82-e82, 2011.

Chang et al., "A general method for facilitating heterodimeric pairing between two proteins: Application to expression of αand β T-cell receptor extracellular segments", PNAS USA 91:11408-11412 (1994).

Chao et al., "Therapeutic Targeting of the Macrophage Immune Checkpoint CD47 in Myeloid Malignancies", Frontiers in Oncology, vol. 9, Art. 1380, pp. 1-9, 2019.

Cheever et al., "The Prioritization of Cancer Antigens: A National Cancer Institute Pilot Project for the Acceleration of Translational Research", Clinical Cancer Research, 15(17):5323-5337, 2009.

Chen et al., "Enhanced proofreading governs CRISPR-Cas9 targeting accuracy", Nature, 550(7676):407-410, 2017.

Chervin et al., "Engineering higher affinity T cell receptors using a T cell display system", The Journal of Immunology Methods 339(2):175-184 (2008).

Cho et al., "Targeted genome engineering in human cells with the Cas9 RNA-guided endonuclease", Nature Biotechnology, 31(3):230-232, 2013.

Chothia et al., "The outline structure of the T-cell αβ receptor", The EMBO Journal 7(12):3745-3755 (1988).

Cignetti et al., CD34+ Acute Myeloid and Lymphoid Leukemic Blasts Can Be Induced to Differentiate Into Dendritic Cells, Blood, 1999, pp. 2048-2055, vol. 94.

Cohen et al., "Recognition of Fresh Human Tumor by Human Peripheral Blood Lymphocytes Transduced with a Bicistronic Retroviral Vector Encoding a Murine Anti-p53 TCR", The Journal of Immunology 175:5799-5808 (2005).

Cong et al., "Multiplex Genome Engineering using CRISPR/Cas Systems", Science, 339(6121):819-823, 2013.

Cougot et al., "'Cap-tabolism", Trends in Biochemical Science 29(8):436-444, (2004).

Cripe et al., "Phase 1 Study of Intratumoral Pexa-Vec (JX-594), an Oncolytic and Immunotherapeutic Vaccinia Virus, in Pediatric Cancer Patients", Molecular Therapy, 2015, 23(3): 602-608.

Danthinne et al., Production of first generation adenovirus vectors: a review, Gene Therapy, 7(20):1707-1714, 2000.

Davila et al., "CD19 CAR-Targeted T Cells Induce Long-Term Remission and B Cell Aplasia in an Immunocompetent Mouse Model of B Cell Acute Lymphoblastic Leukemia", PLOS ONE 8(4):e61338 (2013).

Davis et al., "Basic Methods in Molecular Biology," 1986.

Davodeau et al., "Secretion of Disulfide-linked Human T-cell Receptor γδ Heterdimers", The Journal of Biological Chemistry 268(21):15455-15460 (1993).

DCPRIME BV, "Leukemic Dendritic Cell Vaccination in Patients With Acute Myeloid Leukemia", ClinicalTrials.gov Identifier:

(56) References Cited

OTHER PUBLICATIONS

NCT01373515, Retrieved from: << https://clinicaltrials.gov/ct2/show/NCT01373515?term=NCT01373515&draw=2&rank=1>>, 5 pages, 2011.
De Gruijil et al., "Allogeneic dendritic cell (DC) vaccination as an "off the shelf" treatment to prevent or delay relapse in elderly acute myeloid leukemia patients: results of Phase I/IIa safety and feasibility study", Journal for Immunotherapy of Cancer, Supplement 1, No. P205, 2013.
Elango et al., "Optimized transfection of mRNA transcribed from a d(A/T) 100 tail-containing vector", Biochemical Biophysical Research Commun., 330:958-966, 2005.
EPO Comms, EP 08826916.2, dated Jan. 24, 2011, Jul. 20, 2012, and May 11, 2012.
Erben et al., "CS-1, A Novel c-kithi+ Acute Myeloid Leukemia Cell Line With Dendritic Cell Differentiation Capacity and Absent Immunogenicity", International Journal of Cancer, 105(2):232-240, 2003.
Ferlini et al.; A New Method to Evaluate in vitro Myelotoxicity of Antitumour Agents in the First Steps of Drug Development; Pharmacology & Toxicology 2001, 89; 231-236.
Ferrari et al.; Lack of dendritic cell mobilization into the peripheral blood of cancer patients following standard-or high-dose chemotherapy plus granulocyte-colony stimulating factor; Cancer Immunol Immunother; 2003; 52: 359-366.
Fife et al., "Inhibition of T cell activation and autoimmune diabetes using a B cell surface-linked CTLA-4 agonist", The Journal of Clinical Investigation 116(8):2252-2261 (2006).
Fiorentini et al., "Clinical experience of treatment of metastatic melanoma and solid tumours adopting a derivative of diphtheria toxin: cross-reacting material 197", In Vivo, 2013, 27(2): 197-202.
Frietze et al., "Engineering virus-like particles as vaccine platforms", Curr Opin Virol., 2016, 18: 44-49.
Gaj et al., "Zfn, Talen, and CRISPR/Cas-based methods for genome engineering", Trends in Biotechnology, Jul. 2013, 31(7): 1-20, (Epub May 9, 2013).
Galluzzi et al., "Trial watch: Dendritic cell-based interventions for cancer therapy", OncoImmunology, 1(7):1111-1134, 2012.
Gao et al., "Selective elimination of leukemic CD34+ progenitor cells by cytotoxic T lymphocytes specific for WT1", Blood, 95(7):2198-2203, 2000.
Garboczi et al., "Assembly, Specific Binding, and Crystallization of a Human TCR-αβ with an Antigenic Tax Peptide from Human T Lymphotropic Virus Type 1 and the Class I MHC Moledule HLA-A2[1]", The Journal of Immunology 157(12):5403-5410 (1996).
Garboczi et al., "Structure of the complex between human T-cell receptor, viral peptide and HLA-A2", Nature 384(6605):134-141 (1996).
Garfall et al., "T-cell phenotypes associated with effective CAR T-cell therapy in postinduction vs relapsed multiple myeloma", Blood Advances 3(19):2812-2815 (2019).
Geha et al., "The genetic basis of immunoglobulin-class switching", N Engl J Med., 1994, 330(14): 1008-1009.
Gilbert et al., "CRISPR-Mediated Modular RNA-Guided Regulation of Transcription in Eukaryotes", Cell, 154(2):442-451, 2013.
Gillis et al., "Contribution of human FcgRs to disease with evidence from human polymorphisms and transgenic animal studies", Frontiers in Immunology 5:254 (2014).
Giomarelli et al., "Inhibition of thrombin-induced platelet aggregation using human single-chain Fv antibodies specific for TREM-like transcript-I", Thromb Haemost 97(6):955-964 (2007).
Golden et al., "High-level production of a secreted, heterodimeric αβ murine T-cell receptor in *Escherichia coli*", Journal of Immunological Methods 206:163-169 (1997).
Graham et al., "A new technique for the assay of infectivity of human adenovirus 5 DNA", Virology, 1973, 52(2): 456-467.
Greiner et al., "High-dose RHAMM-R3 peptide vaccination for patients with acute myeloid leukemia, myelodysplastic syndrome and multiple myeloma", Haematologica, 95(7):1191-1197, 2010.
Greiner et al., "Identification and characterization of epitopes of the receptor for hyaluronic acid-mediated motility (RHAMM/CD168) recognized by CD8+ T Cells of HLA-A2-positive patients with acute myeloid leukemia", Blood, 106(3):938-945, 2005.
Grossardt et al., "Granulocyte-macrophage colony-stimulating factor-armed oncolytic measles virus is an effective therapeutic cancer vaccine", Human Gene Therapy, 2013, 24: 644-654.
Guba, et al., "Rapamycin inhibits primary and metastatic tumor growth by antiangiogenesis: involvement of vascular endothelial growth factor", Nature Medicine 8(2):128-135 (2002).
Haddad, "Genetically Engineered Vaccinia Viruses As Agents for Cancer Treatment, Imaging, and Transgene Delivery", Frontiers in Immunology, 2017, 7: 96.
He et al., "CCL3 and CCL20-recruited dendritic cells modified by melanoma antigen gene-1 induce anti-tumor immunity against gastric cancer ex vivo and in vivo", Journal of Experimental & Clinical Cancer Research, 2010, 29: 37.
Hermans et al., "The VITAL assay: a versatile fluorometric technique for assessing CTL- and NKT-mediated cytotoxicity against multiple targets in vitro and in vivo", Journal of Immunological Methods 285(1):25-40 (2004).
Hermanson et al., "Utilizing chimeric antigen receptors to direct natural killer cell activity", Frontiers in Immunology 6(195):1-6 (2015).
Himanen et al., "Crystal structure of an Eph receptor-ephrin complex", Nature 414(6866):933-938 (2001).
Hirooka et al., "Comprehensive immunotherapy combined with intratumoral injection of zoledronate-pulsed dendritic cells, intravenous adoptive activated T lymphocyte and gemcitabine in unresectable locally advanced pancreatic carcinoma: a phase I/II trial", Oncotarget, 2018, 9(2): 2838-2847.
Ho et al., "Inhibition of cocaine binding to the human dopamine transporter by a single chain anti-idiotypic antibody: its cloning, expression, and functional properties", Biochima et Biophysica Acta 1638(3):257-266 (2003).
Holler et al., "In vitro evolution of a T cell receptor with high affinity for peptide/MHC", PNAS USA 97(10):5387-5392 (2000).
Holler et al., "TCRs with high affinity for foreign pMHC show self-reactivity", Nature Immunology 4(1):55-62 (2003).
Howells et al., "Oncolytic Viruses-Interaction of Virus and Tumor Cells in the Battle to Eliminate Cancer", Front Oncol., 2017, 7: 195.
Hu et al., "Evolved Cas9 variants with broad PAM compatibility and high DNA specificity", Nature, 556(7699):57-63, 2018.
Huang et al., "MIR-708 promotes phagocytosis to eradicate T-ALL cells by targeting CD47", Molecular Cancer, Jan. 24, 2018, 17(12): 1-6.
Huck et al., "Sequence of a human immunoglobulin gamma 3 heavy chain constant region gene: comparison with the other human Cy genes", Nucleic Acids Research 14(4):1779-1789 (1986).
Hudecek et al., "The Nonsignaling Extracellular Spacer Domain of Chimeric Antigen Receptors Is Decisive for In Vivo Antitumor Activity", Cancer Immunology Research 3(2):125-135 (2015).
Huston et al., "Protein engineering of antibody binding sites: Recovery of specific activity in an anti-digoxin single-chain Fv analogue produced in *Escherichia coli*", PNAS USA 85:5879-5883 (1988).
Hutzler et al., "Antigen-specific oncolytic MV-based tumor vaccines through presentation of selected tumor-associated antigens on infected cells or virus-like particles", Scientific Reports, 2017, 7: 16892.
Hwang et al., "Controlled differentiation of stem cells", Advanced Drug Delivery Reviews, 60(2):199-214, 2007.
International Search Report and Written Opinion for PCT International Application No. PCT/IB2020/053898, mailed Jul. 2, 2020.
International Search Report and Written Opinion for PCT International Application No. PCT/IB2021/052542, mailed Jun. 25, 2021.
International Search Report and Written Opinion for PCT International Application No. PCT/IB2021/055822, mailed Sep. 30, 2021.
International Search Report and Written Opinion for PCT International Application No. PCT/NL2019/050451, mailed Oct. 4, 2019.
International Search Report and Written Opinion for PCT International Patent Application No. PCT/EP2008/065391, mailed Feb. 26, 2009.

(56) References Cited

OTHER PUBLICATIONS

International Search Report and Written Opinion for PCT International Patent Application No. PCT/EP2013/076067, mailed Feb. 5, 2014.
International Search Report and Written Opinion for PCT International Patent Application No. PCT/IB2021/052543, mailed May 31, 2021.
International Search Report and Written Opinion for PCT International Patent Application No. PCT/IB2021/060233, mailed Apr. 4, 2022.
International Search Report and Written Opinion for PCT International Patent Application No. PCT/IB2022/050555, mailed Apr. 20, 2022.
International Search Report and Written Opinion for PCT International Patent Application No. PCT/IB2022/052211 mailed Jul. 19, 2022.
Jinek et al., "RNA-programmed genome editing in human cells", eLife, 2:e00471, 2013.
Jores et al., "Resolution of hypervariable regions in T-cell receptor β chains by a modified Wu-Kabat index of amino acid diversity", PNAS USA 87:9138-9142 (1990).
Jurincic-Winkler et al., "Antibody response to keyhole limpet hemocyanin (KLH) treatment in patients with superficial bladder carcinoma", Anticancer Res., 1996, 16(4A): 2105-2110.
Kalinski et al., "Consensual immunity: success-driven development of T-helper-1 and T-helper-2 responses", Nature Review 5:251-260 (2005).
Kleinstiver et al., "High-fidelity CRISPR-CAS9 variants with undetectable genome-wide off-targets," Nature, 529(7587):490-495, 2016.
Kloosterman et al., "Deciphering the pathogenic consequences of chromosomal aberrations in human genetic disease", Molecular Cytogenetics, 7(100):1-12, 2014.
Kochenderfer et al., "Construction and Pre-clinical Evaluation of an Anti-CD19 Chimeric Antigen Receptor", Journal of Immunotherapy 32(7):689-702 (2009).
Kohrt et al., "Donor immunization with WT1 peptide augments antileukemic activity after MHC-matched bone marrow transplantation", Blood, 118(19):5319-5329, 2011.
Kotb, "Bacterial Pyrogenic Exotoxins as Superantigens", Clinical Microbiology Reviews 8(3):411-426 (1995).
Koup et al., "Vaccine design for CD8 T lymphocyte responses", Cold Spring Harb Perspect Med., 2011, 1(1): a007252.
Krug et al., "WT1 Peptide Vaccinations Induce CD4 and CD8 T Cell Immune Responses in Patients With Mesothelioma and Non-small Cell Lung Cancer", Cancer Immunology, Immunotherapy, 59(10):1467-1479, 2010.
Kruisbeek, "Adoption of Cryostor® in Manufacturing of a Dendritic Cell Vaccine Platform", BioPreservation Today®, vol. 3, Issue 1, p. 10, 2011.
Kudo-Saito, et al., "Intratumoral vaccination and diversified subcutaneous/intratumoral vaccination with recombinant poxviruses encoding a tumor antigen and multiple costimulatory molecules", Clin Cancer Res., 2004, 10(3): 1090-1099.
Kurtzberg et al., "CD7+, CD4−, CD8-Acute Leukemia: A Syndrome of Malignant Pluripotent Lymphohematopoietic Cells", Blood, 73(2):381-390, 1989.
Lal et al., "Recombinant viruses with other anti-cancer therapeutics: a step towards advancement of oncolytic virotherapy", Cancer Gene Ther., 2018, 25: 216-226.
Larsson et al., "Functional and transcriptional profiling of MUTZ-3, a myeloid cell line acting as a model for dendritic cells", Immunology, 117:156-166, 2006.
Laurell et al., "Intratumorally injection pro-inflammatory allogeneic dendritic cells as immune enhancers: a first in-human study in unfavourable risk patients with metastatic renal cell carcinoma", Journal for Immunotherapy of Cancer 5:52 (2017).
Lawler et al., "Oncolytic Viruses in Cancer Treatment: A Review", JAMA Oncol. Review, 2017, 3(6): 841-849.
Leaf et al., "DCOne as an Allogeneic Cell-based Vaccine for Multiple Myeloma", Journal of Immunotherapy 40(9):315-322 (2017).
Lee et al., "ASTCT Consensus Grading for Cytokine Release Syndrome and Neurologic Toxicity Associated with Immune Effector Cells", Biology of Blood and Marrow Transplantation 25:625-638, doi.org/10.1016/j.bbmt.2018.12.758 (2019).
LeFranc et al., "IMGT unique numbering for immunoglobulin and T cell receptor variable domains and Ig superfamily V-like domains", Developmental and Comparative Immunology 27:55-77 (2003).
Li et al., "Directed evolution of human T-cell receptors with picomolar affinities by phage display", Nature Biotechnology 23(3):349-354 (2005).
Li et al., "Vaccination with CD47 deficient tumor cells elicits an antitumor immune response in mice", Nature Communications, 11:581, 2020.
Liu et al., "Pre-Clinical Development of a Humanized Anti-CD47 Antibody with Anti-Cancer Therapeutic Potential", PLoS One, 10(9): e0137345, 2015.
Logtenberg et al., "Glutaminyl cyclase in an enzymatic modifier of the CD47-SIRPα axis and target for cancer immunotherapy", Nat. Med., 25(4):612-619, 2019.
Lu et al., "Potential New Cancer Immunotherapy: Anti-CD47-SIRPα Antibodies", OncoTargets and Therapy, 13:9323-9331, 2020.
Lundstrom, K., "Viral Vectors in Gene Therapy", Diseases 6(2):42, DOI: 10.3390/diseases6020042 (2018).
Ma et al., "Preclinical development of a novel CD47 nanobody with less toxicity and enhanced anti-cancer therapeutic potential", Journal of Nanobiotechnology, 18:12, pp. 1-15, 2020.
Mali et al., "CAS9 transcriptional activators for target specificity screening and paired nickases for cooperative genome engineering", Nature Biotechnology, 31(9):833-838, 2013.
Mali et al., "RNA-Guided Human Genome Engineering via Cas9", Science, 339(6121):823-826, 2013.
Malito et al., "Structural basis for lack of toxicity of the diphtheria toxin mutant CRM197", Proc Natl Acad Sci U S A, 2012, 109(14): 5229-5234.
Marelli et al., "Oncolytic Viral Therapy and the Immune System: A Double-Edged Sword Against Cancer", Frontiers in Immunology, 2018, 9: 866.
Masterson et al., "MUTZ-3, a human cell line model for the cytokine-induced differentiation of dendritic cells from CD34+ precursors", Blood, 100(2):701-703, 2002.
May et al., "Peptide Epitopes From the Wilms' Tumor 1 Oncoprotein Stimulate CD4+ and CD8+ T Cells That Recognize and Kill Human Malignant Mesothelioma Tumor Cells", Clinical Cancer Research, 13(15):4547-4555, 2007.
Mishra et al., "Structural and immunological characterization of *E. coli* derived recombinant CRM197 protein used as carrier in conjugate vaccines", Bioscience reports, 2018, 38(5): BSR20180238.
Mitchell et al. "Tetanus toxoid and CCL3 improve dendritic cell vaccines in mice and glioblastoma patients", Nature 519(7543):366-369 (2015).
Miyamoto et al., "Heparin-binding epidermal growth factor-like growth factor as a novel targeting molecule for cancer therapy", Cancer Science 97(5):341-347 (2006).
Miyamoto, et al., "New approach to cancer therapy: heparin binding-epidermal growth factor-like growth factor as a novel targeting molecule", Anticancer Res., 2007, 27(6A): 3713-3721.
Mohan et al., "Applications of chemokines as adjuvants for vaccine immunotherapy", Immunobiology, 2018, 223(6-7): 477-485.
Moldenhauer et al., "Tumor Necrosis Factor Alpha-Stimulated Endothelium: An Inducer of Dendritic Cell Development from Hematopoietic Progenitors and Myeloid Leukemic Cells", Stem Cells, 22(2):144-157, 2004.
Montfoort et al., "NKG2A Blockade Potentiates CD8 T Cell Immunity Induced by Cancer Vaccines", Cell 175(7):1744-1755 (2018).
Moosmayer et al., "A single-chain TNF receptor antagonist is an effective inhibitor of TNF mediated cytotoxicity", Therapeutic Immunology, 2(10):31-40 (1995).
Morris, "Cryopreservation of Animal and Human Cell Lines", Methods in Molecular Biology, vol. 368: Cryopreservation and Freeze-Drying Protocols, 2nd Ed. (J. G. Day and G. N. Stacey eds.), Humana Press Inc. Totowa, N.J., pp. 227-236, .2007.

(56) References Cited

OTHER PUBLICATIONS

Moya et al., "Inhibition of Coated Pit Formation in $Hep_2$ Cells Blocks the Cytotoxicity of Diphtheria Toxin But Not That of Ricin Toxin", The Journal of Cell Biology 101(2):548-559 (1985).
Mumtaz et al., "Design of liposomes for circumventing the reticuloendothelial cells", Glycobiology 1(5):505-510 (1991).
Murata et al., "CD47-signal regulatory protein a signaling system and its application to cancer immunotherapy", Cancer Sci., Aug. 2018, 109(8): 2349-2357 (Epub Jul. 4, 2018).
Nacheva et al., "Preventing nondesired RNA-primed RNA extension catalyzed by T7 RNA polymerase", Eur. J. Biochem. 270:1485-1465 (2003).
Nagasawa et al., "DCP-001 stimulates T cell proliferation and increases memory CD4 + T cells in OC patients' PBMC Preclinical studies support therapeutic application of the leukemic cell-based cancer relapse vaccine DCP-001 in ovarian cancer", Nov. 1, 2020, Retrieved from the Internet: URL:https://immunicum.se/wp-content/uploads/2021/04/Poster-DCprime_SITC2020-FINAL.pdf.
Nagasawa et al., "Preclinical studies support therapeutic application of the leukemic cell-based cancer relapse vaccine DCP-001 in ovarian cancer", Journal for Immunotherapy Cancer 8(Suppl. 3): A102-A103 (Abstract 171) (2020).
Nam, et al., "Anti-tumor Effect of Intravenous Administration of CRM197 for Triple-negative Breast Cancer Therapy", Anticancer Res., 2016, 36(7): 3651-3657.
Narita et al., "WT1 Peptide Vaccination in Combination With Imatinib Therapy for a Patient With CML in the Chronic Phase", International Journal of Medical Sciences, 7(2):72-81, 2010.
Neelapu et al., "Chimeric antigen receptor T-cell therapy—assessment and management of toxicities", Nat Rev Clin Oncology 15(1):47-62 (2018).
Neuhaus et al., Multiple sclerosis: Mitoxantrone promotes differential effects on immunocompetent cells in vitro; Journal of Neuroimmunology 168: 128-137 (2005).
Nguyen-Hoai et al., "CCL21 (SLC) improves tumor protection by a DNA vaccine in a Her2/neu mouse tumor model", Cancer Gene Therapy, 2012, 19: 69-76.
Nijman et al., "Phase 1 Study to Evaluate the Safety, Feasibility and Immunogenicity of an Allogeneic, Cell-based Vaccine (DCP-001) in High Grade Serous Ovarian Cancer Patients After Primary Treatment (ALISON)", Feb. 4, 2021, Retrieved from the Internet: URL:https://clinicaltrials.gov/ct2/show/NCT04739527.
Ochsenreither et al., "Wilms Tumor Protein 1 (WT1) Peptide Vaccination-induced Complete Remission in a Patient With Acute Myeloid Leukemia is Accompanied by the Emergence of a Predominant T-cell Clone Both in Blood and Bone Marrow", Journal of Immunotherapy, 34(1):85-91, 2011.
Olusanya et al., "Liposomal Drug Delivery Systems and Anticancer Drugs", Molecules, 2018, 23(4): 907.
Palucka et al., "Recent Developments in Cancer Vaccines", The Journal of Immunology, 186(3):1325-1331, 2011.
Park et al., "Are All Chimeric Antigen Receptors Created Equal?", Journal of Clinical Oncology 33(6):651-653 (2015).
Parkhurst et al., "Characterization of Genetically Modified T-Cell Receptors that Recognize the CEA:691-699 Peptide in the Context of HLA-A2.1 on Human Colorectal Cancer Cells", Clinical Cancer Research 15(1):169-180 (2009).
Pashine et al., "Targeting the innate immune response with improved vaccine adjuvants", Nature Medicine Supplement 11(4): S63-S68 (2005).
Peter et al., "Protective effects of an anti-melanocortin-4 receptor scFv derivative in lipopolysaccharide-induced cachexia in rats", J Cachexia Sarcopenia Muscle Aug. 12, 2012.
Peter et al., "scFv Single Chain Antibody Variable Fragment as Inverse Agonist of the $\beta_2$-Adrenergic Receptor", The Journal of Biological Chemistry 278(38):36740-36747 (2003).
Popkov et al., "Human/mouse cross-reactive anti-VEGF receptor 2 recombinant antibodies selected from an immune b9 allotype rabbit antibody library", Journal of Immunological Methods 288:149-164 (2004).
Presta et al., "Humanization of an Anti-Vascular Endothelial Growth Factor Monoclonal Antibody for the Therapy of Solid Tumors and Other Disorders", Cancer Research 57:4593-4599 (1997).
Qi et al., "Repurposing CRISPR as an RNA-Guided Platform for Sequence-Specific Control of Gene Expression", Cell, 152(5):1173-1183, 2013.
Quintarelli et al., "Cytotoxic T lymphocytes directed to the preferentially expressed antigen of melanoma (PRAME) target chronic myeloid leukemia", Blood, 112(5):1876-1885, 2008.
Quintarelli et al., "High-avidity cytotoxic T lymphocytes specific for a new PRAME-derived peptide can target leukemic and leukemic-precursor cells", Blood, 117(12):3353-3362, 2011.
Rezvani et al., "Leukemia-associated antigen-specific T-cell responses following combined PR1 and WT1 peptide vaccination in patients with myeloid malignancies", Blood, 111(1):236-242, 2008.
Rezvani et al., "T-Cell Responses Directed against Multiple HLA-A* 0201-Restricted Epitopes Derived from Wilms' Tumor 1 Protein in Patients with Leukemia and Healthy Donors: Identification, Quantification, and Characterization", Clinical Cancer Research, 11(24):8799-8807, 2005.
Rosato et al., "Virus-specific memory T cells populate tumors and can be repurposed for tumor immunotherapy", Nature Communications 10:567 (2019).
Rosenberg "Cell transfer immunotherapy for metastatic solid cancer—what clinicians need to know", Nat Rev Clinical Oncology 8(10):577-585 (2011).
Rosenfeld et al., "WT1 in acute leukemia, chronic myelogenous leukemia and myelodysplastic syndrome: therapeutic potential of WT1 targeted therapies", Leukemia, 17:1301-1312, 2003.
Santegoets et al., "A CD34+ Human cell line model of myeloid dendritic cell differentiation: evidence for a CD14+CD11b+ Langerhans cell precursor", Journal of Leukocyte Biology, 80:1337-1344, 2006.
Santegoets et al., "In vitro priming of tumor-specific cytotoxic T lymphocytes using allogeneic dendritic cells derived from the human MUTZ-3 cell line", Cancer Immunology, Immunotherapy, 55:1480-1490, 2006.
Saxena et al., "Re-emergence of Dendritic Cell Vaccines for Cancer Treatment", Trends in Cancer, 2018, 4:2: 119-137.
Schenborn et al., "A novel transcription property of SP6 and T7 RNA polymerases: dependence on template structure", Nucleic Acids Research 13:6223-36 (1985).
Scheraga "Predicting Three-Dimensional Structures of Oligopeptides" Reviews in Computational Chemistry 2:73-142 (1992).
Schlueter et al., "Specificity and Binding Properties of a Single-chain T Cell Receptor", J. Mol. Biol. 256:859-869 (1996).
Schmitt et al., "Chronic myeloid leukemia cells express tumor-associated antigens eliciting specific CD8+ T-cell responses and are lacking costimulatory molecules", Experimental Hematology, 34(12):1709-1719, 2006.
Schmitt et al., "RHAMM-R3 peptide vaccination in patients with acute myeloid leukemia, myelodysplastic syndrome, and multiple myeloma elicits immunologic and clinical responses", The Journal of the American Society of Hematology, 111(3):1357-1365, 2008.
Shankar et al., "Interferon-[gamma] Added During Bacillus Calmette-Guerin Induced Dendritic Cell Maturation Stimulates Potent T h 1 Immune Responses", Oct. 10, 2003, Retrieved from the Internet: URL:https://link.springer.com/content/pdf/10.1186/1479-5876-1-7.pdf.
Shen et al. "Engineering Peptide Linkers for scFv Immunosensors", Anal. Chem. 80(6):1910-1917 (2008).
Shieh et al., "Transgenic Expression of Single-Chain Anti-CTLA-4 Fv on β Cells Protects Nonobese Diabetic Mice from Autoimmune Diabetes", The Journal of Immunology 183(4):2277-2285 (2009).
Slaymaker et al., "Rationally engineered Cas9 nucleases with improved specificity", Science, 351(6268):84-88, 2016.
Smith, et al., "In situ programming of leukaemia-specific T cells using synthetic DNA nanocarriers", Nat. Nanotechnology 12(8):813-820 (2017).
Sockolosky et al., "Durable antitumor responses to CD47 blockade require asaptive immune stimulation", PNAS, 113(19):E2646-2654, 2016.
Sommandas et al., "Novel vaccination strategies using tumour-independent antigens to induce anti-tumour immunity in solid

(56) References Cited

OTHER PUBLICATIONS tumours", https://dcprime.com/wp-content/uploads/2018/07/Poster-FINAL-DCprime_SITC2019-NOV2019.pdf [retrieved on Apr 4, 2022] poster.
Sommandas et al., "Novel vaccination strategies using tumour-independent antigens to induce anti-tumour immunity in solid tumours", Journal for Immunotherapy of Cancer 7(Suppl. 1):P687 (2019) & $34^{th}$ Annual Meeting of the Society for Immunotherapy of Cancer, National Harbour, MD, USA, Nov. 10, 2019.
Sommermeyer et al., "Chimeric antigen receptor-modified T cells derived from defined $CD8^+$ and $CD4^+$ subsets confer superior antitumor reactivity in vivo", Leukemia 30(2):492-500 (2016).
Stepinski et al., "Synthesis and properties of mRNAs containing the novel "anti-reverse" cap analogs 7-methyl(3'-O-methyl)GpppG and 7-methyl(3'-deoxy)GpppG", RNA, 7:1468-1495 (2001).
Stickings, et al., "Transcutaneous immunization with cross-reacting material CRM(197) of diphtheria toxin boosts functional antibody levels in mice primed parenterally with adsorbed diphtheria toxoid vaccine", Infect Immun., 2008, 76(4): 1766-1773.
Subhadra et al., "Inducing Tumor Suppressive Microenvironments through Genome Edited CD47−/− Syngeneic Cell Vaccination", Scientific Reports, Dec. 27, 2019, 9(1): 20057.
Suhrbier, "Multi-epitope DNA vaccines", Immunol Cell Biol., 1997, 75(4): 402-408.
Tack et al., "Phenotypic and genomic analysis of an exceptional case of enteropathy associated T-cell lymphoma", Leukemia Research, 34(8):e183-e189, 2010.
Tacken et al., "Effective induction of naive and recall T-cell responses by targeting antigen to human dendritic cells via a humanized anti-DC-SIGN antibody", Blood, 2005, 106(4): 1278-1285.
Tan et al., "Influence of the hinge region on complement activation, C1q binding, and segmental flexibility in chimeric human immunoglobulins", PNAS USA 87(1):162-166 (1990).
Teachey et al. "Identification of Predictive Biomarkers for Cytokine Release Syndrome afer Chimeric Antigen Receptor T-cell Therapy for Acute Lymphoblastic Leukemia", Cancer Discovery 6(6):664-679 (2016).
Temizoz et al., "Vaccine adjuvants as potential cancer immunotherapeutics", International Immunology 28(7):329-338 (2016).
Themeli et al., "Generation of tumor-targeted human T lymphocytes from induced pluripotent stem cells for cancer therapy", Nature Biotechnology 31(10):928-933 (2013).
Thurner et al., "Generation of large numbers of fully mature and stable dendritic cells from leukapheresis products for clinical application", Journal of Immunological Methods, 223(1):1-15, 1999.
Töpfer et al., "DAP12-Based Activating Chimeric Antigen Receptor for NK Cell Tumor Immunotherapy", The Journal of Immunology 194(7):3201-3212 (2015).
Triozzi et al., "Intratumoral injection of dendritic cells derived in vitro in patients with metastatic cancer", Cancer, 2000, 89(12): 2646-2654.
Tseng et al., "Anti-CD47 antibody-mediated phagocytosis of cancer by macrophages primes an effective antitumor T-call response", PNAS, 110(27):11103-11108, 2013.
Tsukahara et al., "CD19 target-engineered T-cells accumulate at tumor lesions in human B-cell lymphoma xenograft mouse models", Biochem Biophys Res Commun 438(1):84-89 (2013).
Twumasi-Boateng et al., "Oncolytic viruses as engineering platforms for combination immunotherapy", Nature Reviews Cancer 18:419-432 (2018).
Uchida et al., "Mutation in the structural gene for diphtheria toxin carried by temperate phage", Nat New Biol., 1971, 233(35): 8-11.
Ud Din et al., "Effective use of nanocarriers as drug delivery systems for the treatment of selected tumors", Int J Nanomedicine, 2017, 12: 7291-7309.
Ueno et al., "Harnessing Human Dendritic Cell Subsets for Medicine", Immunological Reviews, 234(1):199-212, 2010.
Van De Loosdrecht et al., "A novel allogeneic off-the-shelf dendritic cell vaccine for post-remission treatment of elderly patients with acute myeloid leukemia", Cancer Immunology, Immunotherapy 67(10):1505-1518 (2018).
Van De Ven et al., "Exposure of CD34+ precursors to cytostatic anthraquinone-derivatives induces rapid dendritic cell differentiation: implications for cancer immunotherapy", Cancer Immunology, Immunotherapy, Springer, Berlin, DE, 61(2):181-191, 2011.
Van Helden et al., "Human and murine model cell lines for dendritic cell biology evaluated", Immunology Letters, 117(2):191-197, 2008.
Van Nuffel et al., "Loading of dendritic cells for immunotherapy", ISBT Science Series, 2013, 8: 161-164.
Van Tendeloo et al., "Induction of complete and molecular remissions in acute myeloid leukemia by Wilms' tumor 1 antigen-targeted dendritic cell vaccination", PNAS, 107(31):13824-13829, 2010.
Varela-Rohena et al., "Control of HIV-1 immune escape by CD8 T-calls expressing enhanced T-cell receptor", Nat Med. 14(12):1390-1395 (2008).
Vermeij et al., "Potential Target Antigens for a Universal Vaccine in Epithelial Ovarian Cancer", Clinical and Developmental Immunology, vol. 2010, Article ID 891505, pp. 1-8. 2010.
Vigneron et al, "Database of T cell-defined human tumor antigens: the 2013 update", Cancer Immunity, 2013, 13: 15.
Wadelin et al., "Leucine-rich repeat protein PRAME: expression, potential functions and clinical implications for leukemia", Molecular Cancer, 9(1):1-10, 2010.
Wallgren et al., "Direct Allorecognition Promotes Activation of Bystander Dendritic Cells and Licenses Them for Th1 Priming: A Functional Link Between Direct and Indirect Allosensitization", Scandinavian Journal of Immunology 62:234-242 (2005).
Wang et al., "CMVpp65 Vaccine Enhances the Antitumor Efficacy of Adoptively Transferred CD19-Redirected CMV-Specific T Cells", Clinical Cancer Research 21(13):2993-3002 (2015).
Weiskopf et al., "CD47-blocking immunotherapies stimulate macrophage-mediated destruction of small-cell lung cancer", Journal of Clinical Investigation, 126(7):2610-2620, 2016.
Weiskopf et al., "Engineered SIRPα Variants as Immunotherapeutic Adjuvants to Anticancer Antibodies", Science, 341(6141):88-91, 2013.
Westers et al., Rapid generation of antigen-presenting cells from leukaemic blasts in acute myeloid leukaemia, Cancer Immunology, Immunotherapy. 2003, pp. 17-27, vol. 52.
Wlodarska et al., "A New Subtype of Pre-B Acute Lymphoblastic Leukemia With t(5;12)(q31q33;p12), Molecularly and Cytogenetically Distinct From t(5;12) in Chronic Myelomonocytic Leukemia", Blood, 89(5):1716-1722, 1997.
Xie et al., "Direct demonstration of MuSK involvement in acetylcholine receptor clustering through identification of agonist ScFv", Nature Biotechnology 15(8):768-771 (1997).
Yan et al., "Engineering Upper Hinge Improves Stability and Effector Function of a Human IgG1", The Journal of Biological Chemistry 287(8):5891-5897 (2012).
Yilmaz et al., Activated myeloid dendritic cells accumulate and colocalize with CD3+ T cells in coronary artery lesions in patients with Kawasaki disease, Experimental Molecular Pathology 2007, pp. 93-103, vol. 83, No. 1.
Zhang et al., "Advances in Anti-Tumor Treatments Targeting the CD47/SIRPα Axis", Frontiers Immunology, vol. 11, Art. 18, pp. 1-15, 2020.
Zhang et al., "An NKp30-Based Chimeric Antigen Re3ceptor Promotes T Cell Effector Functions and Antitumor Efficacy In Vivo", The Journal of Immunology 189(5):2290-2299 (2012).
Zhao et al., "Characteristics of an scFv Antibody Fragment That Binds to Immunoglobulin G of Graves' Disease Patients and Inhibits Autoantibody-Mediated Thyroid-Stimulating Activity", Hybridoma 27(6):455-451 (2008).
Zhao et al., "Multiple injections of electroporated autologous T cells expressing a chimeric antigen receptor mediate regression of human disseminated tumor", Cancer Research 70(22):9053-9061 (2010).
Zhou et al., "Exclusive Transduction of Human $CD4^+$ T Cells upon Systemic Delivery of CD4-Targeted Lentiviral Vectors", The Journal of Immunology 195(5):2493-2501 (2015).

(56) References Cited

OTHER PUBLICATIONS

Zhou et al., "T-cell receptor gene transfer exclusively to human $CD8^+$ cells enhances tumor cell killing", Blood 120(22):4334-4342 (2012).
Zibera, et al.; An epirubicin/paclitaxel combination mobilizes large amounts of hematopoietic progenitor cells in patients with metastatic breast cancer showing optimal response to the same chemotherapy regimen; Haematologica 1999; 84:924-929.
Zuo et al., "Transfer of Cellular Content from the Allogeneic Cell-Based Cancer Vaccine DCP-001 to Host Dendritic Cells Hinges on Phosphatidylserine and Is Enhanced by CD47 Blockade", Cells, Nov. 19, 2021, 10(11): 3233.
U.S. Appl. No. 12/736,920 2011/0117051 U.S. Pat. No. 8,470,789, filed Nov. 19, 2010 May 19, 2011 Jun. 25, 2013, Sandra Van Wetering, Method for Inducing and Accelerating Cells.
U.S. Appl. No. 14/648,210 2015/0297698 U.S. Pat. No. 10,064,923, filed May 28, 2015 Oct. 22, 2015 Sep. 4, 2018, Sandra Van Wetering, Therapeutic Cancer Vaccines Derived from a Novel Dendritic Cell Line.
U.S. Appl. No. 16/101,028 2019/0000945 U.S. Pat. No. 11,027,001, filed Aug. 10, 2018 Jan. 3, 2019 Jun. 8, 2021, Sandra Van Wetering, Therapeutic Cancer Vaccines Derived from a Novel Dendritic Cell Line.
U.S. Appl. No. 17/239,097 2021/0346479, filed Apr. 23, 2021 Nov. 11, 2021, Sandra Van Wetering, Therapeutic Cancer Vaccines Derived from a Novel Dendritic Cell Line.
U.S. Appl. No. 16/857,851 2020/0390876 U.S. Pat. No. 11,052,144, filed Apr. 24, 2020 Dec. 17, 2020 Jul. 6, 2021, Erik Hans Manting, Methods of Tumor Vaccination.
U.S. Appl. No. 17/342,893 2021/0401961, filed Jun. 9, 2021 Dec. 30, 2021, Erik Hans Manting, Methods of Tumor Vaccination.
U.S. Appl. No. 16/858,326 2020/0397883 U.S. Pat. No. 11,071,778, filed Apr. 24, 2020 Dec. 24, 2020 Jul. 27, 2021, Erik Hans Manting, Combination Product for Use in Tumor Vaccination.
U.S. Appl. No. 17/361,462 2022/0023406, filed Jun. 29, 2021 Jan. 27, 2022, Erik Hans Manting, Combination Product for Use in Tumor Vaccination.
U.S. Appl. No. 17/361,477 2022/0023405, filed Jun. 29, 2021 Jan. 27, 2022, Erik Hans Manting, Use of Leukemia-Derived Cells in Ovarian Cancer Vaccines.
U.S. Appl. No. 17/213,460 2021/0322471, filed Mar. 26, 2021 Oct. 21, 2021, Erik Hans Manting, In Vivo Use of Modified Cells of Leukemic Origin For Enhancing the Efficacy of Adoptive Cell Therapy.
U.S. Appl. No. 17/213,461 2022/0168407, filed Mar. 26, 2021 Oct. 21, 2021, Erik Hans Manting, Ex Vivo Use of Modified Cells of Leukemic Origin for Enhancing the Efficacy of Adoptive Cell Therapy.
U.S. Appl. No. 17/519,101 2022/0168407, filed Nov. 4, 2021 Jun. 2, 2022, Erik Hans Manting, Use of Tumor-Independent Antigens In Immunotherapies.
U.S. Appl. No. 17/580,919 2022/0249639, filed Jan. 21, 2022 Aug. 11, 2022, Erik Hans Manting, Methods of Tumor Vaccination.
U.S. Appl. No. 17/692,321 2022/0305100, filed Mar. 11, 2022 Sep. 29, 2022, Erik Hans Manting, Methods of Vaccination and Use of CD47 Blockade.
Akahori et al., "Antitumor of CAR-T cells targeting the intracellular onco-protein WT1 can be enhanced by vaccination", Blood, 2018, 132(11): 1134-1145.
Dranoff et al., "Vaccination with irradiated tumor cells engineered to secrete murine granulocyte-macrophage colony-stimulating factor stimulates potent, specific, and long-lasting anti-tumor immunity", PNAS USA, Apr. 1993, 90: 3539-3543.

* cited by examiner

IL-1β

GM-CSF

IFNγ

IL-2

TNFα

IL-8

RANTES
pg/mL
PBMC only
progenitor only
prog + PBMC
DCP-001 only
DCP-001 + PBMC

CD3 T cells

CD4+T cells

CD8+ T cells

CTL against SKOV 3

Induction of cytotoxic CD8⁺ T cells against SKOV 3

Strong responses

| | Measurable anti-tumor responses | |
|---|---|---|
| | OC patients | Healthy donors |
| +++ | 5/8 | 1/7 |
| ++ | 0/8 | 2/4 |
| + | 1/8 | 1/4 |
| Total positive responses | 6/8 | 4/7 |

Induction of strong anti-tumour responses in ovarian cancer patients

EX VIVO USE OF MODIFIED CELLS OF LEUKEMIC ORIGIN FOR ENHANCING THE EFFICACY OF ADOPTIVE CELL THERAPY

RELATED APPLICATIONS

This application claims priority to U.S. Provisional Patent Application Ser. No. 63/001,189, filed Mar. 27, 2020, and 63/110,003, filed Nov. 5, 2020, the entire disclosures of which are hereby incorporated by reference herein

BACKGROUND

The use of chimeric antigen receptor (CAR) and T cell receptor (TCR) engineered T cells has recently been the subject of much preclinical and clinical research. These genetically modified T cells combine the principles of basic immunology with current advances in immunotherapy and provide a promising approach to utilize the body's own immune system to attack diseases such as cancer. Adoptive cell therapies generally involve the collection of a patient's own immune cells, ex vivo expansion and genetic modification of the immune cells to encode a tumor antigen-specific receptor. In some cases, the immune cells may be obtained from an allogeneic source. The genetically modified immune cells are infused back into the patient resulting in effective tumor clearance. Current immunotherapies based on the infusion of ex vivo expanded immune cells have shown remarkable success in cancer treatment, particularly in hematological malignancies. For example, clinical trials in patients with advanced B cell leukemias and lymphomas treated with CD19-specific CAR T cells have induced durable remissions in adults and children.

Genetically modified immune cells infused back into the patients (in particular autologous cells) are mainly terminally differentiated and often fail in maintaining long-lasting memory responses against tumor. Further, despite impressive clinical effectiveness, adoptive cell therapies face challenges as durable clinical responses are affected by inadequate in vivo expansion, survival and long-term persistence of the engineered cells after treatment. One challenge arises in the propensity of T cells to become exhausted, a phenomenon defined by the development of suboptimal effector function, increased expression of inhibitory receptors and the development of an expression profile that is distinct from that of functional effector or memory T cells. T cell exhaustion leads to reduced effector functions such as cytotoxicity against disease-causing cells and cytokine expression.

There is a need in the art for genetically modified immune cells with improved function and therapeutic effectiveness, and methods for making the same. The present disclosure addresses and satisfies this need.

SUMMARY

The present disclosure is based, at least in part, on the finding that certain cells of leukemic origin can improve the expansion, efficacy and/or functionality of certain modified immune cells (e.g., autologous patient derived CAR-T cells) employed in adoptive cell therapy when these cells are combined together ex vivo. In certain embodiments, immune cells that are expanded and co-cultured in the presence of the cells of leukemic origin exhibit improved expansion and persistence following subsequent administration to a patient by adoptive cell transfer. In other embodiments, immune cells exposed to the modified cells of leukemic origin demonstrate improved CD4 help, e.g., based on CD4 phenotype and CD4/CD8 ratios. In still other aspects, and without being bound to any particular theory, it is thought that the exposure to "background" anti-tumor immunity enables prolonged T cell activation and survival of the modified immune cell post-infusion. In certain embodiments, the modified immune cell may be exhibit prolonged post-infusion survival due to co-culturing the modified immune cell ex vivo with a cell of leukemic origin that expresses the same tumor antigen that the modified immune cells is designed to target in the patient. Accordingly, the methods of the present disclosure address one of the main bottlenecks in CAR-T and other adoptive T cell therapies, namely the limited expansion capacity of T cells, particularly patient derived autologous T cells.

In certain aspects, a method for activating, stimulating and and/or expanding a population of immune cells, comprising: obtaining a population of cells comprising immune cells; contacting the population of cells with a modified cell of leukemic origin, wherein the modified cell comprises a mature dendritic cell phenotype and is non-proliferating; and co-culturing the population of cells and the modified cell of leukemic origin under conditions suitable to stimulate proliferation of the immune cells, thereby activating and expanding the population of immune cells, is provided.

In other aspects, a method for generating a population of memory T cells, comprising: obtaining a population of cells comprising immune cells; contacting the population of cells with a modified cell of leukemic origin, wherein the modified cell comprises a mature dendritic cell phenotype and is non-proliferating; and co-culturing the population of cells and the modified cell of leukemic origin under conditions suitable to stimulate proliferation of the immune cells, thereby generating the population of memory T cells, is provided.

In certain exemplary embodiments, the population of cells comprise immune cells comprising an engineered immune receptor. In certain exemplary embodiments, the engineered immune receptor is a chimeric antigen receptor (CAR) or a T cell receptor (TCR).

In other aspects, a method for generating a population of autologous T cells with enhanced activation status, comprising: obtaining a population of autologous T cells from a patient suffering from a cancer; modifying the population of autologous T cells to express an engineered immune receptor selected from a chimeric antigen receptor (CAR) or a T cell receptor (TCR) which binds a tumor antigen in the patient; contacting the population of modified autologous T cells with a modified cell of leukemic origin, wherein the modified cell comprises a mature dendritic cell phenotype and is non-proliferating; and co-culturing the population of modified autologous T cells and the modified cell of leukemic origin under conditions suitable to stimulate proliferation of the modified autologous T cells, thereby generating the population of autologous T cells with enhanced activation status, is provided.

In certain exemplary embodiments, the method is for treating the patient suffering from the cancer, the method further comprising administering the population of autologous cells with enhanced activation status to the patient suffering from the cancer.

In other aspects, a method for expanding a population of autologous T cells comprising anti-tumor antigen specificity, comprising: obtaining a population of autologous T cells from a patient suffering from a cancer; modifying the population of autologous T cells to express an engineered immune receptor selected from a chimeric antigen receptor (CAR) or a T cell receptor (TCR) which binds a tumor antigen on a tumor cell in the patient; contacting the population of modified autologous T cells with a modified cell of leukemic origin, wherein the modified cell comprises a mature dendritic cell phenotype and is non-proliferating; and co-culturing the population of modified autologous T cells and the modified cell of leukemic origin under conditions suitable to expand and stimulate the population of modified autologous T cells, thereby generating a population of modified autologous T cells comprising anti-tumor antigen specificity, wherein the population of modified autologous T cells comprising anti-tumor antigen specificity is capable of reacting with tumor cells of the patient.

In certain exemplary embodiments, the population of modified autologous cells is capable of reacting with tumor cells of the patient that do not express the tumor antigen to which the engineered immune receptor binds.

In certain exemplary embodiments, the modified cell comprises at least one tumor antigen selected from the group consisting of WT-1, RHAMM, PRAME, MUC-1, p53, and Survivin.

In certain exemplary embodiments, the immune cells are activated following exposure to the endogenous cells expressed by the modified cell of leukemic origin.

In certain exemplary embodiments, the modified cell is CD34-positive, CD1a-positive, CD83-positive, and CD14-negative. In certain exemplary embodiments, the modified cell further comprises a cell surface marker selected from the group consisting of DC-SIGN, Langerin, CD40, CD70, CD80, CD83, CD86, and any combination thereof. In certain exemplary embodiments, the modified cell is further: CD40-positive, CD80-positive, and CD86-positive. In certain exemplary embodiments, the modified cell comprises a costimulatory molecule. In certain exemplary embodiments, the costimulatory molecule is CD70. In certain exemplary embodiments, the modified cell comprises an MHC class I molecule. In certain exemplary embodiments, the modified cell comprises an MHC class II molecule.

In certain exemplary embodiments, the modified cell is loaded with an exogenous antigen or peptide fragments thereof. In certain exemplary embodiments, the exogenous antigen is a tumor-associated antigen (TAA) or non-tumor-associated antigen. In certain exemplary embodiments, the modified cell is capable of expressing the exogenous antigen. In certain exemplary embodiments, the modified cell is not capable of expressing the exogenous antigen. In certain exemplary embodiments, the exogenous antigen is provided in the form of a peptide, a nucleotide sequence, whole protein, or tumor lysate. In certain exemplary embodiments, the exogenous antigen is matched with the antigen to which the engineered immune receptor binds. In certain exemplary embodiments, the exogenous antigen is different from the antigen to which the engineered immune receptor binds.

In certain exemplary embodiments, the modified cell of leukemic origin is loaded with the exogenous antigen or peptide fragments thereof prior to its exhibiting a mature dendritic cell phenotype. In certain exemplary embodiments, the modified cell of leukemic origin is loaded with the exogenous antigen or peptide fragments thereof during transition of the modified cell of leukemic origin to a mature dendritic cell phenotype. In certain exemplary embodiments, the modified cell of leukemic origin is loaded with the exogenous antigen or peptide fragments thereof prior to, after the modified cell of leukemic origin exhibits a mature dendritic cell phenotype.

In certain exemplary embodiments, the modified cell comprises a genetic aberration between chromosome 11p15.5 to 11p12. In certain exemplary embodiments, the genetic aberration encompasses about 16 Mb of genomic regions.

In certain exemplary embodiments, the modified cell has been irradiated.

In certain exemplary embodiments, the conditions suitable to stimulate proliferation of the immune cells or autologous T cells comprises providing signal-1 to the immune cells. In certain exemplary embodiments, signal-1 is provided by the modified cell. In certain exemplary embodiments, signal-1 comprises activation of a TCR/CD3 complex.

In certain exemplary embodiments, the conditions suitable to stimulate proliferation of the immune cells or autologous T cells comprises providing signal-2 to the immune cells. In certain exemplary embodiments, signal-2 is provided by the modified cell. In certain exemplary embodiments, signal-2 comprises activation of a costimulatory molecule. In certain exemplary embodiments, the costimulatory molecule is CD70.

In certain exemplary embodiments, the population of cells or autologous T cells is derived from a human. In certain exemplary embodiments, the population of cells or autologous T cells comprise both CD4+ and CD8+ cells, and wherein the method results in combined stimulation of both the CD4+ and CD8+ cells. In certain exemplary embodiments, the population of cells or autologous T cells comprise both CD4+ and CD8+ cells, and wherein the method results in an increased ratio of CD4+ to CD8+ cells. In certain exemplary embodiments, the population of cells or autologous T cells comprise non-stimulated T cells.

In certain exemplary embodiments, the population of cells or autologous T cells comprise a functional endogenous TCR repertoire.

In certain exemplary embodiments, the population of cells or autologous T cells engineered to target the exogenous antigen of the modified immune cell of leukemic origin.

In certain exemplary embodiments, the population of cells or autologous T cells is engineered to target the same tumor-associated antigen (TAA) of the modified cell of leukemic origin.

In certain exemplary embodiments, the population of cells or autologous T cells is cross-reactive with non-tumor derived antigens displayed by the modified immune cell of leukemic origin.

In certain exemplary embodiments, the non-tumor derived antigens are viral or vaccine-derived recall antigens.

In certain exemplary embodiments, the engineered immune cells are Epstein Barr Virus (EBV)-specific T cells.

In certain exemplary embodiments, the CAR comprises an antigen binding domain, a transmembrane domain, and an intracellular domain comprising a costimulatory domain and a primary signaling domain. In certain exemplary embodiments, the antigen binding domain comprises a full-length antibody or antigen-binding fragment thereof, a Fab, a single-chain variable fragment (scFv), or a single-domain antibody. In certain exemplary embodiments, the antigen binding domain is specific for a tumor-associated antigen (TAA) or a non-tumor-associated antigen.

In certain exemplary embodiments, the modified cell comprises an exogenous antigen or peptide fragments thereof, and wherein the antigen binding domain is specific for a tumor-associated antigen (TAA) or non-tumor-associated antigen that is distinct from the exogenous antigen.

In certain exemplary embodiments, the CAR further comprises a hinge region. In certain exemplary embodiments, the hinge region is a hinge domain selected from the group consisting of an Fc fragment of an antibody, a hinge region of an antibody, a CH2 region of an antibody, a CH3 region of an antibody, an artificial hinge domain, a hinge comprising an amino acid sequence of CD8, or any combination thereof. In certain exemplary embodiments, the transmembrane domain is selected from the group consisting of an artificial hydrophobic sequence, a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), ICOS (CD278), or CD154, and a transmembrane domain derived from a killer immunoglobulin-like receptor (KIR). In certain exemplary embodiments, the intracellular domain comprises a costimulatory signaling domain and an intracellular signaling domain. In certain exemplary embodiments, the costimulatory signaling domain comprises one or more of a costimulatory domain of a protein selected from the group consisting of proteins in the TNFR superfamily, CD27, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS (CD278), NKG2C, B7-H3 (CD276), and an intracellular domain derived from a killer immunoglobulin-like receptor (KIR), or a variant thereof. In certain exemplary embodiments, the intracellular signaling domain comprises an intracellular domain selected from the group consisting of cytoplasmic signaling domains of a human CD3 zeta chain (CD3), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof.

In certain exemplary embodiments, the TCR is endogenous to the immune cells or autologous T cells. In certain exemplary embodiments, the TCR is exogenous to the immune cells or autologous T cells. In certain exemplary embodiments, the TCR comprises a TCR alpha chain and a TCR beta chain. In certain exemplary embodiments, the TCR is selected from the group consisting of a wildtype TCR, a high affinity TCR, and a chimeric TCR. In certain exemplary embodiments, the TCR is selected from the group consisting of a full-length TCR, a dimeric TCR, and a single-chain TCR.

In certain exemplary embodiments, the modified cell comprises an exogenous antigen or peptide fragments thereof, and wherein the TCR is specific for a tumor-associated antigen (TAA) or non-tumor-associated antigen that is distinct from the exogenous antigen. In certain exemplary embodiments, the modified cell comprises an exogenous antigen or peptide fragments thereof, and wherein the TCR is specific for a tumor-associated antigen (TAA) or non-tumor-associated antigen that is the same as the exogenous antigen.

In other aspects, a method for generating an antigen-specific immune cell, comprising inducing generation of the antigen-specific immune cell by contacting an immune cell with a modified cell of leukemic origin, wherein the modified cell comprises a mature dendritic cell phenotype and is non-proliferating, is provided.

In certain exemplary embodiments, the modified cell comprises a target antigen. In certain exemplary embodiments, the target antigen is endogenous to the modified cell and selected from the group consisting of WT-1, RHAMM, PRAME, MUC-1, p53, Survivin, and any combination thereof. In certain exemplary embodiments, the target antigen is exogenous to the modified cell. In certain exemplary embodiments, the target antigen is a tumor-associated antigen (TAA) or a non-tumor-associated antigen.

In certain exemplary embodiments, the modified cell is CD34-positive, CD1a-positive, CD83-positive, and CD14-negative. In certain exemplary embodiments, the modified cell further comprises a cell surface marker selected from the group consisting of DC-SIGN, Langerin, CD40, CD70, CD80, CD83, CD86, and any combination thereof. In certain exemplary embodiments, the modified cell is further: CD40-positive, CD80-positive, and CD86-positive. In certain exemplary embodiments, the modified cell comprises a costimulatory molecule. In certain exemplary embodiments, the costimulatory molecule is CD70. In certain exemplary embodiments, the modified cell comprises an MHC class I molecule. In certain exemplary embodiments, the modified cell comprises an MHC class II molecule. In certain exemplary embodiments, the modified cell comprises a genetic aberration between chromosome 11p15.5 to 11p12. In certain exemplary embodiments, the genetic aberration encompasses about 16 Mb of genomic regions.

In certain exemplary embodiments, the modified cell has been irradiated.

In other aspects, a method for expanding a population of modified immune cells, comprising: obtaining a population of modified immune cells, wherein the modified immune cells comprise an immune receptor; contacting the population of cells with a modified cell of leukemic origin, wherein the modified cell comprises a mature dendritic cell phenotype and is non-proliferating; and culturing the population of modified immune cells under conditions suitable to stimulate proliferation of the modified immune cells, thereby expanding the population of modified immune cells, is provided.

In certain exemplary embodiments, the modified cell comprises a target antigen. In certain exemplary embodiments, the target antigen is endogenous to the modified cell and selected from the group consisting of WT-1, RHAMM, PRAME, MUC-1, p53, Survivin, and any combination thereof. In certain exemplary embodiments, the target antigen is exogenous to the modified cell. In certain exemplary embodiments, the target antigen is a tumor-associated antigen (TAA) or a non-tumor-associated antigen.

In certain exemplary embodiments, the modified cell is CD34-positive, CD1a-positive, CD83-positive, and CD14-negative. In certain exemplary embodiments, the modified cell further comprises a cell surface marker selected from the group consisting of DC-SIGN, Langerin, CD40, CD70, CD80, CD83, CD86, and any combination thereof. In certain exemplary embodiments, the modified cell is further: CD40-positive, CD80-positive, and CD86-positive. In certain exemplary embodiments, the modified cell comprises a costimulatory molecule. In certain exemplary embodiments, the costimulatory molecule is CD70. In certain exemplary embodiments, the modified cell comprises an MHC class I molecule. In certain exemplary embodiments, the modified cell comprises an MHC class II molecule. In certain exemplary embodiments, the modified cell comprises a genetic aberration between chromosome 11p15.5 to 11p12. In certain exemplary embodiments, the genetic aberration encompasses about 16 Mb of genomic regions.

In certain exemplary embodiments, the modified cell has been irradiated.

In certain exemplary embodiments, the conditions suitable to stimulate proliferation of the immune cells comprises providing signal-1 to the immune cells. In certain exemplary embodiments, signal-1 is provided by the modified cell. In certain exemplary embodiments, signal-1 comprises activation of a TCR/CD3 complex.

In certain exemplary embodiments, the conditions suitable to stimulate proliferation of the immune cells comprises providing signal-2 to the immune cells. In certain exemplary embodiments, signal-2 is provided by the modified cell. In certain exemplary embodiments, signal-2 comprises activation of a costimulatory molecule. In certain exemplary embodiments, the costimulatory molecule is CD70.

In other aspects, a method for treating a disease or disorder in a subject in need thereof, comprising: administering to the subject a modified immune cell produced by any one of the methods of the preceding claims, is provided.

In certain exemplary embodiments, the disease or disorder is a cancer.

In certain exemplary embodiments, the modified cell is an autologous cell derived from the patient suffering from the cancer.

In certain exemplary embodiments, the cancer is a tumor. In certain exemplary embodiments, the tumor is a liquid tumor. In certain exemplary embodiments, the tumor is a solid tumor.

In other aspects, a method for treating a tumor in a subject in need thereof, comprising: administering to the subject a modified immune cell produced by any one of the preceding methods, is provided.

In certain exemplary embodiments, the immune cell comprises specificity for the exogenous antigen or peptide fragments thereof. In certain exemplary embodiments, the immune cell comprises an engineered immune receptor comprising specificity for the exogenous antigen or peptide fragments thereof. In certain exemplary embodiments, the engineered immune receptor is a chimeric antigen receptor (CAR) or a T cell receptor (TCR).

In certain exemplary embodiments, the method further comprises a tumor-marking step comprising administering a composition to the subject at the tumor site, wherein the composition comprises an exogenous antigen or peptide fragments thereof.

In certain exemplary embodiments, the exogenous antigen is a tumor-associated antigen (TAA) or a non-tumor-associated antigen.

In certain exemplary embodiments, the tumor marking-step comprises administering the composition into the tumor or proximal to the tumor. In certain exemplary embodiments, the tumor-marking step is performed after the modified immune cell is administered. In certain exemplary embodiments, the tumor-marking step is performed before the modified immune cell is administered.

In certain exemplary embodiments, the immune cell is a T cell. In certain exemplary embodiments, the immune cell is an autologous T cell.

In certain exemplary embodiments, the non-tumor-associated antigen is of a viral, a bacterial, or a fungal origin. In certain exemplary embodiments, the non-tumor-associated antigen is an allergen, a toxin, or a venom. In certain exemplary embodiments, the non-tumor-associated antigen is an allergen, a toxin, or a venom. In certain exemplary embodiments, the non-tumor-associated antigen is a diphtheria toxin or a non-toxic variant thereof. In certain exemplary embodiments, the non-tumor-associated antigen is CRM197 or a variant thereof. In certain exemplary embodiments, the non-tumor-associated antigen is a peptide derived from cytomegalovirus (CMV). In certain exemplary embodiments, the non-tumor-associated antigen is a pp65 peptide.

Other embodiments will become apparent from a review of the ensuing detailed description, drawings and accompanying claims.

BRIEF DESCRIPTION OF THE DRAWINGS

The foregoing and other features and advantages of the present disclosure will be more fully understood from the following detailed description of illustrative embodiments taken in conjunction with the accompanying drawings.

FIG. 6A shows the response of PRAME T cell clones to DCP-001; FIG. 6B shows the response of WT-1 T cell clones to DCP-001; FIG. 6C shows the response of MUC-1 T cell clones to DCP-001, and FIG. 6D shows the response of RHAMM T cell clones to DCP-001.

FIG. 7A shows stimulation of WT-1 specific T cells by DCOne mDCs loaded with exogenous antigens including matched exogenous antigen (WT-1). FIG. 7B shows stimulation of NY-ESO-1 specific T cells by DCOne mDCs loaded with exogenous antigens including matched exogenous antigen (NY-ESO-1) IFN response the induction of IFNγ in response to NY-ESO-1 specific T cells.

FIG. 8A and FIG. 8C) and healthy donors (FIG. 8B and FIG. 8D).

FIG. 9A and FIG. 9C) and healthy donors (FIG. 9B and FIG. 9D).

DETAILED DESCRIPTION

Figure 1A:
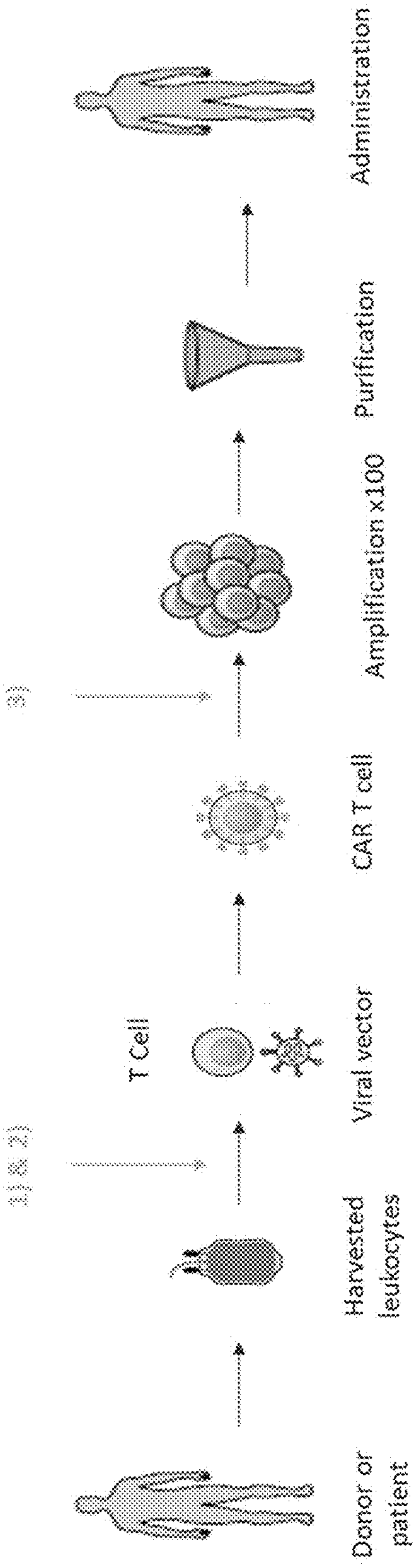
FIG. 1A shows that DCOne mDCs could be added at two different steps in the CAR T manufacturing process to: 1) Improve the enrichment and activation status of T cells (memory phenotype); 2) Induce additional tumor-targeting specificity in the adoptive T cell pool (based on endogenous or exogenous antigens); and/or 3) Improve the expansion of CAR expressing T cells (phenotype, viability and CAR expression levels).

Provided herein are methods for improving the stimulation and expansion of immune cells, as well as methods for generating antigen-specific immune cells and immune cells of a memory phenotype. Methods for enhancing the effect of genetically modified immune cells are also provided. In certain embodiments, the methods comprise contacting a population of cells (e.g., comprising immune cells) with a modified cell of leukemic origin. Methods of treating a disease or disorder are also provided, comprising the administration of a non-proliferating modified cell of leukemic origin into a subject who has undergone adoptive cell therapy. Such methods may prolong the duration of the clinical effect of a genetically modified immune cell, and/or function to stabilize subjects following adoptive cell therapy. In certain embodiments, the modified cell of leukemic origin is non-proliferating (e.g., via irradiation). In certain embodiments, the non-proliferating modified cell of leukemic origin is a non-proliferating DCOne derived cell.

It is to be understood that the methods described herein are not limited to particular methods and experimental conditions disclosed herein as such methods and conditions may vary. It is also to be understood that the terminology used herein is for the purpose of describing particular embodiments only, and is not intended to be limiting. The methods described herein use conventional molecular and cellular biological and immunological techniques that are well within the skill of the ordinary artisan. Such techniques are well known to the skilled artisan and are explained in the scientific literature.

A. Definitions

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, e.g., ±5%, ±1%, or ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

The term "antigen" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen.

The term "antigen" or "antigenic," as used in relation to a polypeptide as described herein, refers generally to a biological molecule which contains at least one epitope specifically recognized by a T cell receptor, an antibody, or other elements of specific humoral and/or cellular immunity. The whole molecule may be recognized, or one or more portions of the molecule, for instance following intracellular processing of a polypeptide into an MHC peptide antigen complex and subsequent antigen presentation. The term "antigenic polypeptide" is interchangeable with "polypeptide antigen." This terminology includes antigenic parts of said polypeptides, for instance produced after intracellular processing of a polypeptide and in the context of a MHC peptide antigen complex. The term “antigen” or “antigenic” includes reference to at least one, or more, antigenic epitopes of a polypeptide as described herein. In certain embodiments, a “non-tumor antigen” refers to herein as an antigen that is not derived from a tumor. For example, in certain embodiments, a non-tumor antigen may be a foreign antigen.

A “tumor-independent antigen” refers to herein as an antigen that is not derived from a tumor that a subject is currently suffering from. For example, in certain embodiments, a tumor-independent antigen may be a foreign antigen. A tumor-independent antigen may be human or non-human. In certain embodiments, in the context of marking a tumor of a human subject with a tumor-independent antigen, the tumor-independent antigen may be of a non-human origin. In certain embodiments, in the context of marking a tumor of a host subject with a tumor-independent antigen, the tumor-independent antigen may be of a non-host origin. In certain embodiments, a tumor-independent antigen may be an antigen that is not expressed by a tumor that the subject is currently suffering from. For example, if a subject is currently suffering from pancreatic cancer, a tumor-independent antigen is a pancreatic-cancer independent antigen. In such an example, a pancreatic-cancer independent antigen can be an antigen derived from a non-pancreatic cancer that is not expressed by the pancreatic cancer, e.g., an ovarian cancer antigen that is not expressed by the pancreatic cancer. Similarly, when a certain antigen is associated with a strong immune response within a certain tumor type, such antigen could be introduced in tumors of the same type which do not express such antigen. This could, e.g., be the case for testis-associated antigens like NY-ESO-1 in ovarian cancer.

The tumor-independent antigen can be a recall antigen. The term “recall antigen,” as used herein, refers to an antigen (e.g., an antigenic polypeptide) which has previously (e.g., prior to the occurrence of a tumor in the subject or prior to a tumor-marking step) been encountered by a subject. Recall antigens are those which have previously been encountered by the subject and for which there exists pre-existing memory lymphocytes in the subject (e.g., memory T cells and/or memory B cells). In certain embodiments, a recall antigen refers to an antigen (e.g., antigenic polypeptide) for which pre-existing memory lymphocytes exist in the subject, e.g., as a result of prior infections or vaccinations. In certain embodiments, a recall antigen refers to an antigenic polypeptide which has previously been encountered by a subject via vaccination. In certain embodiments, the recall antigen is an antigenic polypeptide for which there is pre-existing immunity in said subject.

Furthermore, antigens can be derived from recombinant or genomic DNA. A skilled artisan will understand that any DNA, which comprises a nucleotide sequences or a partial nucleotide sequence encoding a protein that elicits an immune response therefore encodes an “antigen” as that term is used herein. Furthermore, one skilled in the art will understand that an antigen need not be encoded solely by a full length nucleotide sequence of a gene. It is readily apparent that the present disclosure includes, but is not limited to, the use of partial nucleotide sequences of more than one gene and that these nucleotide sequences are arranged in various combinations to elicit the desired immune response. Moreover, a skilled artisan will understand that an antigen need not be encoded by a “gene” at all. It is readily apparent that an antigen can be generated synthesized or can be derived from a biological sample. Such a biological sample can include, but is not limited to a tissue sample, a tumor sample, a cell or a biological fluid.

As used herein, the term “autologous” is meant to refer to any material derived from the same individual to which it is later to be re-introduced into the individual.

A “co-stimulatory ligand” refers to a molecule on an antigen presenting cell that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LTGHT, NKG2C, B7-H3, and a ligand that specifically binds with CD83.

A “co-stimulatory molecule” refers to the cognate binding partner on a T cell that specifically binds with a co-stimulatory ligand, thereby mediating a co-stimulatory response by the cell, such as, but not limited to proliferation. Co-stimulatory molecules include, but are not limited to, an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, and the like.

A “co-stimulatory signal,” as used herein, refers to a signal, which in combination with a primary signal, such as TCR/CD3 ligation, leads to T cell proliferation and/or upregulation or downregulation of key molecules. In certain exemplary embodiments, the co-stimulatory signal is CD70.

A “disease” is a state of health of an animal wherein the animal cannot maintain homeostasis, and wherein if the disease is not ameliorated then the animal’s health continues to deteriorate. In contrast, a “disorder” in an animal is a state of health in which the animal is able to maintain homeostasis, but in which the animal’s state of health is less favorable than it would be in the absence of the disorder. Left untreated, a disorder does not necessarily cause a further decrease in the animal’s state of health.

“Effective amount” or “therapeutically effective amount” are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the disclosure. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

An "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

The term "immune response," as used herein, includes T cell mediated and/or B cell mediated immune responses. Exemplary immune functions of T cells include, e.g., cytokine production and induction of cytotoxicity in other cells. B cell functions include antibody production. In addition, the term includes immune responses that are indirectly affected by T cell activation, e.g., antibody production and activation of cytokine responsive cells, e.g., macrophages. Immune cells involved in the immune response include lymphocytes, such as B cells and T cells ($CD4^+$ and $CD8^+$ cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes. In certain embodiments, the term refers to a T cell mediated immune response. The immune response may in some embodiments be a T cell-dependent immune response. The skilled person understands that the phrase "immune response against a tumor" also includes immune responses against a non-human antigenic polypeptide that is introduced into the tumor micro-environment by intratumoral administration, such as intratumoral administration of (i) dendritic cells, including autologous or allogeneic dendritic cells, loaded with said polypeptide or (ii) viruses comprising a nucleic acid encoding said polypeptide.

The term "T cell dependent immune response," as used herein, refers to an immune response wherein either T cells, B cells or both T cell and B cell populations are activated, and wherein T cells further assist T and B cells and other immune cells in executing their function.

The term "immunosuppressive" is used herein to refer to reducing overall immune response.

"Insertion/deletion," commonly abbreviated "indel," is a type of genetic polymorphism in which a specific nucleotide sequence is present (insertion) or absent (deletion) in a genome.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells. They can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the disclosure. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, e.g., a human.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Parenteral" administration of an immunogenic composition includes, e.g., subcutaneous (s.c.), intravenous (i.v.), intramuscular (i.m.), intradermal, intraperitoneal, or intrasternal injection, or infusion techniques.

The term "polynucleotide," as used herein, is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species. For example, an antibody recognizes and binds to a specific protein structure rather than to proteins generally. If an antibody is specific for epitope "A," the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject," as used herein, refers to the recipient of a method as described herein, i.e., a recipient that can mount a cellular immune response, and is a mammal. In certain embodiments, the subject is a human. In certain embodiments, the subject is a domesticated animal, e.g., a horse, a cow, a pig, a sheep, a dog, a cat, etc. The terms "patient" and "subject" may be used interchangeably. In certain embodiments, the subject is a human suffering from a tumor (e.g., a solid tumor). In certain embodiments, the subject is a domesticated animal suffering from a tumor (e.g., a solid tumor).

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (α) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The term "tumor," as used herein, includes reference to cellular material, e.g., a tissue, proliferating at an abnormally high rate. A growth comprising neoplastic cells is a neoplasm, also known as a "tumor," and generally forms a distinct tissue mass in a body of a subject. A tumor may show partial or total lack of structural organization and functional coordination with the normal tissue. As used herein, a tumor is intended to encompass hematopoietic tumors as well as solid tumors. In certain embodiments, the tumor is a solid tumor. The term "tumor," as used herein, includes reference to the tumor micro-environment or tumor site, i.e., the area within the tumor and the area directly outside the tumorous tissue. In certain embodiments, the tumor micro-environment or tumor site includes an area within the boundaries of the tumor tissue. In certain embodiments, the tumor micro-environment or tumor site includes the tumor interstitial compartment of a tumor, which is defined herein as all that is interposed between the plasma membrane of neoplastic cells and the vascular wall of the newly formed neovessels. As used herein, the terms "tumor micro-environment" or "tumor site" refers to a location within a subject in which a tumor resides, including the area immediately surrounding the tumor.

A tumor may be benign (e.g., a benign tumor) or malignant (e.g., a malignant tumor or cancer). Malignant tumors can be broadly classified into three major types: those arising from epithelial structures are called carcinomas, those that originate from connective tissues such as muscle, cartilage, fat or bone are called sarcomas, and those affecting hematopoietic structures (structures pertaining to the formation of blood cells) including components of the immune system, are called leukemias and lymphomas. Other tumors include, but are not limited to, neurofibromatosis. In certain exemplary embodiments, the tumor is a glioblastoma. In certain exemplary embodiments, the tumor is an ovarian cancer (e.g., an epithelial ovarian cancer, which can be further subtyped into a serous, a clear cell, an endometrioid, a mucinous, or a mixed epithelial ovarian cancer).

Solid tumors are abnormal masses of tissue that can be benign or malignant. In certain embodiments, solid tumors are named for the type of cells that form them (such as sarcomas, carcinomas, and lymphomas). Examples of solid tumors, such as sarcomas and carcinomas, include, but are not limited to, liposarcoma, fibrosarcoma, chondrosarcoma, osteosarcoma, myxosarcoma, and other sarcomas, mesothelioma, synovioma, leiomyosarcoma, Ewing's tumor, colon carcinoma, rhabdomyosarcoma, pancreatic cancer, lymphoid malignancy, lung cancers, breast cancer, prostate cancer, ovarian cancer, hepatocellular carcinoma, adenocarcinoma, basal cell carcinoma, sweat gland carcinoma, squamous cell carcinoma, medullary thyroid carcinoma, pheochromocytomas sebaceous gland carcinoma, papillary thyroid carcinoma, papillary adenocarcinomas, papillary carcinoma, medullary carcinoma, bronchogenic carcinoma, hepatoma, renal cell carcinoma, bile duct carcinoma, Wilms' tumor, choriocarcinoma, cervical cancer, seminoma, testicular tumor, bladder carcinoma, melanoma, CNS tumors (e.g., a glioma, e.g., brainstem glioma and mixed gliomas, glioblastoma (e.g., glioblastoma multiforme), germinoma, astrocytoma, craniopharyngioma, medulloblastoma, ependymoma, Schwannoma, CNS lymphoma, acoustic neuroma, pinealoma, hemangioblastoma, meningioma, oligodendroglioma, retinoblastoma, neuroblastoma, and brain metastases), and the like.

Carcinomas that can be amenable to therapy by a method disclosed herein include, but are not limited to, squamous cell carcinoma (various tissues), basal cell carcinoma (a form of skin cancer), esophageal carcinoma, bladder carcinoma, including transitional cell carcinoma (a malignant neoplasm of the bladder), hepatocellular carcinoma, colorectal carcinoma, bronchogenic carcinoma, lung carcinoma, including small cell carcinoma and non-small cell carcinoma of the lung, colon carcinoma, thyroid carcinoma, gastric carcinoma, breast carcinoma, ovarian carcinoma, adrenocortical carcinoma, pancreatic carcinoma, sweat gland carcinoma, prostate carcinoma, papillary carcinoma, adenocarcinoma, sebaceous gland carcinoma, medullary carcinoma, papillary adenocarcinoma, ductal carcinoma in situ or bile duct carcinoma, cystadenocarcinoma, renal cell carcinoma, choriocarcinoma, Wilm's tumor, seminoma, embryonal carcinoma, cervical carcinoma, testicular carcinoma, nasopharyngeal carcinoma, osteogenic carcinoma, epithelial carcinoma, uterine carcinoma, and the like.

Sarcomas that can be amenable to therapy by a method disclosed herein include, but are not limited to, myxosarcoma, chondrosarcoma, chordoma, osteogenic sarcoma, liposarcoma, fibrosarcoma, angiosarcoma, lymphangiosarcoma, endotheliosarcoma, osteosarcoma, mesothelioma, Ewing's sarcoma, leiomyosarcoma, rhabdomyosarcoma, lymphangioendotheliosarcoma, synovioma, and other soft tissue sarcomas.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

The term "immunogenic composition," as used herein, refers to a substance which induces a specific immune response against an immunogen in a subject who is in need of an immune response against said immunogen. The composition may include an adjuvant and optionally one or more pharmaceutically-acceptable carriers, excipients and/or diluents. The immunogenic composition can be employed in prime-boost vaccination, such as at least 2, 3, 4 or at least 5 immunizations separated in time. The immunogenic composition can be an (allogeneic) dendritic cell comprising said immunogen.

The term "immunogen," as used herein, refers to a compound such as a polypeptide capable of eliciting an immune response that is specifically directed against an antigenic polypeptide as described herein. An immunogen is also an antigen, i.e., an antigenic polypeptide. In contrast, an antigen is not necessarily an immunogen. In certain embodiments, the immunogen is used for vaccination (in an immunogenic composition such as a vaccine composition), and the antigenic polypeptide prepared for intratumoral delivery is instead used for marking a tumor as a target for an immune response to be elicited, or as a target for an immune response that is already elicited, in a subject. The term "immunogen" is also used to refer to a nucleic acid which encodes the non-human antigenic polypeptide as described herein. In addition, embodiments that describe the antigenic polypeptide, also apply to an immunogen as described herein.

The term "non-human," as used herein in the context of an antigenic polypeptide, includes polypeptides that are not of human origin, including a bacterial polypeptide, a polypeptide of an organism of the Archaea domain, a fungal polypeptide and a viral polypeptide. Also included are plant polypeptides and non-human mammalian polypeptides such as polypeptides of non-human primates, rodents (e.g., mice and rats), rabbits, pigs, sheep, goats, cows, pigs, horses and donkeys, and birds (e.g., chickens, turkeys, ducks, geese and the like). Also included are polypeptides of snails or other mollusks, including *Megathura crenulata*. The term "non-human" also encompasses synthetic polypeptides, i.e., polypeptides that have an artificial sequence designed by man and that do not occur in nature or are not yet identified in nature. In addition, the term comprises human polypeptides comprising an amino acid alteration from the native sequence, the alteration providing for immunogenicity in a human subject.

The term "intratumoral," as used herein, refers to delivery or transport of the antigenic polypeptide, or the nucleic acid encoding said polypeptide, into a tumor. One example of intratumoral delivery, or transport, of an antigenic polypeptide as described herein is by intratumoral administration, a route of administration generally known in the art. As an alternative route for intratumoral administration, the antigen may be delivered to the tumor via a tumor-specific carrier, such as an oncolytic virus or a gene therapy vector, which have been broadly developed to deliver gene sequences to tumors. The use of such vehicles allows for multiple routes of administration, in addition to intratumoral administration, such by as intravenous or intraperitoneal administration, subsequently resulting in the delivery of the nucleic acid encoding said polypeptide, into the tumor (Lundstrom, *Diseases,* 6(2):42 (2018); Alemany, *Biomedicines,* 2, p. 36-49 (2014); Twumasi-Boateng et al., *Nature Reviews Cancer* 18, p. 419-432 (2018).

The phrase "prepared for intratumoral delivery," as used herein, refers to an antigenic polypeptide as described herein, or a nucleic acid encoding said polypeptide as described herein, that is adapted for intratumoral delivery and/or is in a formulation that allows for intratumoral delivery. The preparation used for intratumoral delivery may be composed such that it has a beneficial effect on the interaction between the immune system and the tumor. For instance, dendritic cells, such as autologous or allogeneic dendritic cells, can be loaded with said polypeptide and upon intratumoral administration may provide for additional immune stimulation via direct interaction with T cells entering the tumor and/or indirectly by recruiting bystander antigen-presenting cells (Laurel) et al., *Journal for Immunotherapy of Cancer,* 5:52 (2017); Wallgren et al., *Scandinavian Journal of Immunology,* 62, p. 234-242 (2005). Another example of such preparation is that the polypeptide or nucleic acid as described herein can be comprised in a tumor-delivery vehicle such as a tumor-targeted vehicle including a tumor-specific virus such as an oncolytic virus (or any other virus that selectively replicates in tumor cells) that infects a tumor cell and which allows for (i) expression of said nucleic acid in a tumor cell, and (ii) (subsequently) intracellular processing and antigen presentation (MHC) of said (expressed) polypeptide by said tumor cell. The skilled person is well aware of other methods and means for preparing a polypeptide, or a nucleic acid encoding said polypeptide, for intratumoral delivery. For instance, the skilled person can apply other tumor-targeted delivery vehicles such as a tumor-specific nanoparticle or he can apply intratumoral administration through intratumoral injection in order to deliver said polypeptide or nucleic acid into a tumor. In certain embodiments, the polypeptide or nucleic acid prepared for intratumoral delivery as described herein, is comprised in a tumor-targeted vehicle.

As used herein, the term "extratumoral" refers to a location, e.g., in the body of a subject, that is away (e.g., distal) from a tumor and immediately surrounding tissue (e.g., that may make up the tumor micro-environment).

The compositions for use as described herein, elicit an immune response specifically directed against a tumor in a subject. The skilled person understands that "specifically directed" refers to an immune response that is specific for a tumor. The specificity is introduced by a step of marking a tumor with a non-human antigenic polypeptide as a target for an immune response, and by eliciting an immune response against an antigenic part of said non-human antigenic polypeptide (i.e., the target). Thus, in certain embodiments, the compositions for use as described herein, is for use in eliciting an immune response against a tumor marked as a target for said immune response. In certain embodiments, the compositions for use as described herein, is for use in eliciting an immune response against a tumor that is marked as a target for said immune response; wherein said target is a non-human antigenic polypeptide as described herein.

In certain embodiments, the non-human antigenic polypeptide, or a nucleic acid encoding said polypeptide, prepared for intratumoral delivery as described herein, serves the purpose of marking the tumor as a target for an immune response (polypeptide/nucleic acid for marking a tumor). Thus, in certain embodiments, said polypeptide or said nucleic acid prepared for intratumoral delivery marks the tumor as a target for an immune response following intratumoral delivery.

As used herein, the term "vaccination step" refers to a step in a method (vaccination strategy) as described herein, wherein a composition comprising an antigenic polypeptide (e.g., a non-tumor antigen) or a nucleic acid encoding an antigenic polypeptide is administered to a subject at a site distal to a tumor site. In certain embodiments, in a vaccination step of a method as described herein, the composition is administered at a site that is not the site in which the tumor resides (e.g., not the tumor site). In certain embodiments, in a vaccination step of a method as described herein, the composition is administered at an extratumoral site. As used herein, the term "booster step" refers to a step in a method (vaccination strategy) as described herein, wherein a booster composition comprising an antigenic polypeptide (e.g., a non-tumor antigen) or a nucleic acid encoding the antigenic polypeptide is administered to a subject at a site distal to a tumor site. In certain embodiments, a booster step is performed after a vaccination step, wherein the vaccination step results in an immune response against the antigen, and the booster step enhances the immune response against the antigen. In certain embodiments, a booster step results in an enhanced immune response in a subject having pre-existing immunity against, e.g., an antigenic polypeptide (e.g., a non-tumor antigen). In certain embodiments, the vaccination step in a method as described herein is a booster stem, e.g., when the subject has pre-existing immunity against, e.g., a non-tumor recall antigen.

The term "marking," "mark" or "marked," as used herein, refers to active manipulation of the antigenic state of a tumor by intratumoral delivery of an antigenic polypeptide, or a nucleic acid encoding said polypeptide, as described herein. This provides for direct labelling of a tumor cell through intracellular delivery and subsequent processing and presentation of said polypeptide by said tumor cell, or provides for indirect labelling of a tumor via: (i) intracellular delivery and subsequent processing and presentation of said polypeptide by a non-tumor cell in said tumor; or (ii) extracellular delivery of said antigenic polypeptide to said tumor (i.e., extracellular to the cells present in said tumor before marking), for instance by using a dendritic cell that comprises a nucleic acid encoding said polypeptide or that is loaded with said antigenic polypeptide. As used herein, the term "tumor-marking step" refers to a step in a method (e.g., a vaccination strategy) as described herein, wherein a composition comprising an antigenic polypeptide (e.g., a non-tumor antigen) or a nucleic acid encoding an antigenic polypeptide is administered to a subject at a tumor site.

The term "modified cell of leukemic origin," as used herein, refers to a cell that can take up an antigen such as an antigenic polypeptide into its cell, and presents the antigen, or an immunogenic part thereof together with an MHC class I complex or MHC class II complex. In certain embodiments, the modified cell of leukemic origin is a cell derived from cell line DCOne as deposited under the conditions of the Budapest treaty with the DSMZ under accession number DSMZ ACC3189 on 15 Nov. 2012. The process of obtaining mature cells from the deposited DCOne cell line is, for instance, described in EP2931878B1.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

B. Modified Cell of Leukemic Origin

Provided herein are methods comprising the use of a modified cell of leukemic origin to stimulate and expand immune cells, generate antigen-specific immune cells, and for methods of treatment. As used herein, the term "modified cell of leukemic origin" refers to a cell capable of taking up an antigen such as an antigenic polypeptide, and capable of presenting the antigen, or an immunogenic part thereof, together with an MHC class I complex or MHC class II complex. A modified cell of leukemic origin provided herein comprises a mature dendritic cell phenotype. The term "dendritic cell," as used herein, refers to a professional antigen presenting cell (APC) that can take up an antigen such as an antigenic polypeptide into its cell, and presents the antigen, or an immunogenic part thereof together with an MHC class I complex or MHC class II complex. Having a mature dendritic cell phenotype means that the modified cell of leukemic origin is capable of performing similar functions to those of a mature dendritic cell. The term includes both immature dendritic cells ("imDC") and mature dendritic cells ("mDC"), depending on maturity.

In certain embodiments, the modified cell of leukemic origin is derived from leukemia cells. In certain embodiments, the modified cell of leukemic origin is derived from a patient having leukemia. In certain embodiments, the modified cell of leukemic origin is derived from the peripheral blood of a patient having leukemia. In certain embodiments, the modified cell of leukemic origin is derived from the peripheral blood of a patient having acute myeloid leukemia. The skilled artisan will recognize that a modified cell of leukemic origin can be derived from any patient obtained peripheral blood, wherein the patient has any type of leukemia, given that the modified cell of leukemic origin thus derived comprises the characteristics disclosed herein.

In certain embodiments, the modified cell of leukemic origin is CD34-positive, CD1a-positive, and CD83-positive. In certain embodiments, the modified cell of leukemic origin comprises a cell surface marker selected from the group consisting of CD14, DC-SIGN, Langerin, CD40, CD70, CD80, CD83, CD86, and any combination thereof. In certain embodiments, the modified cell of leukemic origin comprises an MHC class I molecule. In certain embodiments, the modified cell of leukemic origin comprises an MHC class II molecule. In certain embodiments, the modified cell of leukemic origin is CD34-positive, CD1a-positive, CD83-positive, and CD14-negative. In certain embodiments, the modified cell of leukemic origin is CD40-positive, CD80-positive, and CD86-positive. In certain embodiments, the modified cell of leukemic origin is CD34-positive, CD1a-positive, CD83-positive, CD40-positive, CD80-positive, CD86-positive, and CD14-negative.

In certain embodiments, the modified cell of leukemic origin comprises a genetic aberration between chromosome 11p15.5 to 11p12. In certain embodiments, the genetic aberration encompasses about 16 Mb of genomic regions (e.g., from about 20.7 Mb to about 36.6 Mb). In certain embodiments, the genetic aberration contains a loss of about 60 known and unknown genes.

In certain embodiments, the modified cell of leukemic origin comprises a co-stimulatory molecule. In certain embodiments, the co-stimulatory molecule includes, without limitation, an MHC class I molecule, BTLA and Toll ligand receptor. Examples of co-stimulatory molecules include CD70, CD80, CD86, 4-1BBL (CD137-ligand), OX40L, CD30L, CD40, PD-L1, ICOSL, ICAM-1, lymphocyte function-associated antigen 3 (LFA3 (CD58)), K12/SECTM1, LIGHT, HLA-E, B7-H3 and CD83.

In certain embodiments, the modified cell of leukemic origin comprises at least one endogenous antigen. Depending on the leukemic origin of the modified cell, the modified cell of leukemic origin may comprise at least one known endogenous antigen that is specific to the leukemic origin. In certain embodiments, the endogenous antigen is a tumor-associated antigen. In certain embodiments, an endogenous tumor-associated antigen may be selected from the group consisting of WT-1, RHAMM, PRAME, p53, Survivin, and MUC-1.

In certain embodiments, the modified cell of leukemic origin comprises an exogenous antigen or peptide fragments thereof. Such an exogenous antigen may be provided to the modified cell of leukemic origin via various antigen loading strategies. For example, strategies for loading a modified cell of leukemic origin may include, without limitation, the use of synthetic long peptides, mRNA loading, peptide-pulsing, protein-loading, tumor lysate-loading, coculturing with a tumor cell, RNA/DNA transfection or viral transduction. Other strategies for loading a modified cell of leukemic origin are known to those of skill in the art and may be used to load a modified cell of leukemic origin with an exogenous antigen. In general, the modified cell of leukemic origin will process the exogenous antigen via particular molecules, e.g., via MHC I or MHC II. As such, an exogenous antigen comprised by the modified cell of leukemic origin may be an MHC class I antigen or an MHC class II antigen. In certain embodiments, the exogenous antigen is a tumor-associated antigen. For example, in certain embodiments, the modified cell of leukemic origin is loaded with NY-ESO-1 peptide and/or WT-1 peptide, or a tumor-independent antigen such as CMVpp65. In certain embodiments, the exogenous antigen is associated with a disease or disorder, e.g., a non-cancer-associated disease or disorder. It will be appreciated by those of ordinary skill in the art that any tumor-associated antigen or antigen associated with a disease or disorder can be provided to the modified cell of leukemic origin described herein. As such, in certain embodiments, a modified cell of leukemic origin comprises any tumor-associated antigen or antigen associated with a disease or disorder contemplated by those skilled in the art.

In certain embodiments, the exogenous antigen is a non-tumor-associated antigen (i.e., a tumor-independent antigen). In certain embodiments, the modified cell of leukemic origin is loaded with a tumor-independent antigen, i.e. an antigen not associated with a tumor. For example, suitable tumor-independent antigens include, without limitation, proteins of viral, bacterial, fungal origin; allergens, toxins and venoms, or model antigens of various sources such as chicken egg ovalbumin and keyhole limpet hemocyanin from the giant keyhole limpet, *Megathura crenulata*. In certain embodiments, a suitable tumor-independent antigen is of bacterial origin. In certain embodiments, a suitable tumor-independent antigen is a diphtheria toxin. In certain embodiments, a suitable tumor-independent antigen is a non-toxic variant of diphtheria toxin. For example, in certain embodiments, a suitable tumor-independent antigen is CRM197 or a variant thereof. In certain embodiments, a modified cell of leukemic origin comprises CRM197 or a variant thereof. In certain embodiments, a suitable tumor-independent antigen is of viral origin. In certain embodiments, a suitable tumor-independent antigen is a peptide derived from cytomegalovirus (CMV), e.g., a peptide derived from CMV internal matrix protein pp65. In certain embodiments, a modified cell of leukemic origin comprises a pp65 peptide. It will be appreciated by those of ordinary skill in the art that any tumor-independent antigen can be provided to the modified cell of leukemic origin described herein. As such, in certain embodiments, a modified cell of leukemic origin comprises any tumor-independent antigen contemplated by those skilled in the art.

In certain embodiments, loading a modified cell of leukemic origin with an exogenous antigen or peptide fragments thereof, includes use of a photochemical processes (e.g., photochemical internalization). In certain embodiments, loading a modified cell of leukemic origin with an exogenous antigen or peptide fragments thereof is achieved with the use of photochemical internalization. In certain embodiments, photochemical internalization may be used to enhance the delivery of an antigen or peptide fragments thereof (e.g., an antigenic polypeptide (e.g., a non-tumor antigen), or a nucleic acid encoding the antigenic polypeptide) into the modified cell of leukemic origin.

Photochemical internalization refers to a delivery method which involves the use of light and a photosensitizing agent for introducing otherwise membrane-impermeable molecules into the cytosol of a target cell, but which does not necessarily result in destruction or death of the target cell. In this method, the molecule to be internalized or transferred is applied to the cells in combination with a photosensitizing agent. Exposure of the cells to light of a suitable wavelength activates the photosensitizing agent which in turn leads to disruption of the intracellular compartment membranes and the subsequent release of the molecule into the cytosol. In photochemical internalization, the interaction between the photosensitizing agent and light is used to affect the cell such that intracellular uptake of the molecule is improved. Photochemical internalization as well as various photosensitizing agents are described in PCT Publication Nos. WO 96/07432, WO 00/54708, WO 01/18636, WO 02/44396, WO 02/44395, and WO 03/020309, U.S. Pat. Nos. 6,680,301, 5,876,989, the disclosures of which are incorporated by reference herein in their entireties. In certain embodiments, photochemical internalization is used to deliver an antigen into the cytosol of a tumor cell. In certain embodiments, photochemical internalization is used to enhance the delivery of an antigen into the cytosol of a tumor cell.

Loading of the modified cell of leukemic origin with an exogenous antigen or peptide fragments thereof may be performed at any time. The skilled person will be able to determine and carry out the specific timing of loading of the modified cell of leukemic origin to best suit their needs. For example, in certain embodiments, the modified cell of leukemic origin is loaded with an exogenous antigen or peptide fragments thereof prior to its exhibiting a mature dendritic cell phenotype. In certain embodiments, the modified cell of leukemic origin is loaded with the exogenous antigen or peptide fragments thereof during transition of the modified cell of leukemic origin to a mature dendritic cell phenotype. In certain embodiments, the modified cell of leukemic origin is loaded with the exogenous antigen or peptide fragments thereof after the modified cell of leukemic origin exhibits a mature dendritic cell phenotype.

In certain embodiments, the modified cell of leukemic origin is a cell of cell line DCOne as described in PCT Publication Nos. WO 2014/006058 and WO 2014/090795, the disclosures of which are incorporated by reference herein in their entireties. In certain embodiments, modified cell of leukemic origin is a cell of cell line DCOne and comprises a mature dendritic cell phenotype that is CD34-positive, CD1a-positive, and CD83-positive. In certain embodiments, modified cell of leukemic origin is a cell of cell line DCOne and is CD34-positive, CD1a-positive, and CD83-positive. In certain embodiments, modified cell of leukemic origin is a cell of cell line DCOne and comprises a cell surface marker selected from the group consisting of CD14, DC-SIGN, Langerin, CD80, CD86, CD40, CD70, and any combination thereof. In certain embodiments, modified cell of leukemic origin is a cell of cell line DCOne and comprises MHC class I. In certain embodiments, modified cell of leukemic origin is a cell of cell line DCOne and comprises MHC class II. In certain embodiments, the modified cell of leukemic origin is a cell of cell line DCOne and is CD34-positive, CD1a-positive, CD83-positive, and CD14-negative. In certain embodiments, the modified cell of leukemic origin is a cell of cell line DCOne and is CD40-positive, CD80-positive, and CD86-positive. In certain embodiments, the modified cell of leukemic origin is a cell of cell line DCOne and is CD34-positive, CD1a-positive, CD83-positive, CD40-positive, CD80-positive, CD86-positive, and CD14-negative. In certain embodiments, modified cell of leukemic origin is a cell of cell line DCOne and comprises a genetic aberration between chromosome 11p15.5 to 11p12. In certain embodiments, modified cell of leukemic origin is a cell of cell line DCOne and comprises a genetic aberration that encompasses about 16 Mb of genomic regions (e.g., from about 20.7 Mb to about 36.6 Mb). In certain embodiments, modified cell of leukemic origin is a cell of cell line DCOne and comprises a genetic aberration that contains a loss of about 60 known and unknown genes.

As provided herein, certain methods are directed to the use of a modified cell of leukemic origin, wherein the modified cell is non-proliferating. In certain embodiments, the modified cell of leukemic origin has been irradiated. In certain embodiments, the modified cell of leukemic origin has been irradiated prior to its use in a method disclosed herein. Irradiation can, for example, be achieved by gamma irradiation at 30-150 Gy, e.g., 100 Gy, for a period of 1 to 3 hours, using a standard irradiation device (Gammacell or equivalent). Irradiation ensures that any remaining progenitor cell in a composition comprising the modified cell of leukemic origin, e.g., a CD34 positive cell, cannot continue dividing. The cells may, for example, be irradiated prior to injection into patients, when used as a vaccine, or immediately after cultivating is stopped. In certain embodiments, the cells are irradiated to inhibit their capacity to proliferate and/or expand, while maintaining their immune stimulatory capacity.

C. Stimulation and Expansion of Immune Cells

Signaling through the T cell receptor (TCR) provides what is commonly referred to as signal-1, and is not sufficient for adequate T cell activation. Costimulatory molecules provide indispensable signals, commonly referred to as signal-2, for proliferation, survival, and differentiation. Both signal-1 and signal-2 is required for full T cell activation, and the strength of these signals influence the size (e.g., number of T cells) in the resulting T cell population. Indeed, naïve T cells that only receive signal 1 without signal 2 are unresponsive and/or die through apoptosis.

Whether prior to or after modification of cells to express an immune receptor (e.g., a T cell receptor or a chimeric antigen receptor), the cells can be activated and expanded in number using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Publication No. 20060121005. Generally, the immune cells (e.g., T cells, memory T cells) of the disclosure may be expanded by integrating the provision of signal-1 and signal-2. In certain embodiments, these signals are provided by contacting immune cells with a surface having attached thereto an agent that stimulates a CD3/TCR complex associated signal (i.e., signal-1) and a ligand that stimulates a costimulatory molecule on the surface of the immune cells (i.e., signal-2). For example, chemicals such as calcium ionophore A23187, phorbol 12-myristate 13-acetate (PMA), or mitogenic lectins like phytohemagglutinin (PHA) can be used to create an activation signal for the immune cell.

Immune cell populations (e.g., T cell populations) may be stimulated in vitro (e.g., ex vivo) such as by contact with an anti-CD3 antibody, or antigen-binding fragment thereof, or an anti-CD28 antibody immobilized on a surface, or by contact with a protein kinase C activator (e.g., bryostatin) in conjunction with a calcium ionophore. For co-stimulation of an accessory molecule on the surface of the immune cells (e.g., T cells), a ligand that binds the accessory molecule may be used. For example, a population of immune cells (e.g., T cells) can be contacted with an anti-CD3 antibody and an anti-CD28 antibody, under conditions appropriate for stimulating proliferation of the immune cells. For example, the agents providing each signal may be in solution or coupled to a surface. As those of ordinary skill in the art can readily appreciate, the ratio of particles to cells may depend on particle size relative to the target cell. In certain embodiments, the immune cells (e.g., T cells), are combined with agent-coated beads (e.g., magnetic beads), the beads and the cells are subsequently separated, and then the cells are cultured. In certain embodiments, prior to culture, the agent-coated beads and cells are not separated but are cultured together.

In certain exemplary embodiments, the foregoing conditions for stimulating and expanding immune cells (e.g., T cells), may be provided by a modified cell of leukemic origin as described herein. Accordingly, provided herein is a method for activating and expanding a population of immune cells (e.g., T cells), comprising: obtaining a population of cells comprising immune cells; contacting the population of cells with a modified cell of leukemic origin; and culturing the population of cells under conditions suitable to stimulate proliferation of the immune cells, thereby activating and expanding the population of immune cells.

Due to the nature of the modified cell of leukemic origin, methods utilizing the modified cell of leukemic origin result in the enhanced generation of certain subsets of immune cells. As known in the art, conventional adaptive T cell subtypes include helper CD4+ T cells, cytotoxic CD8+ T cells, memory T cells, and regulatory T cells. In certain embodiments, provided herein are methods for generating a population of memory immune cells (e.g., memory T cells). Accordingly, provided herein is a method for generating a population of memory immune cells (e.g., memory T cells), comprising: obtaining a population of cells comprising immune cells (e.g., T cells); contacting the population of cells with a modified cell of leukemic origin; and culturing the population of cells under conditions suitable to stimulate proliferation of the immune cells, thereby generating the population of memory immune cells. In certain embodiments, provided herein are methods for generating a population of memory immune cells (e.g., memory T cells). Accordingly, provided herein is a method for generating a population of memory T cells, comprising: obtaining a population of cells comprising immune cells (e.g., T cells); contacting the population of cells with a modified cell of leukemic origin; and culturing the population of cells under conditions suitable to stimulate proliferation of the immune cells, thereby generating the population of memory T cells. As such, the methods provided herein can be used to enrich the memory T cell population from a source, e.g., peripheral blood. Memory T cells are long-lived and can quickly expand to large numbers of effector T cells upon exposure to a cognate antigen. Through these characteristics, memory T cells can provide the immune system with memory function against previously encountered antigens. In general, memory T cells are characterized by the presence of certain cell surface markers, including, CD4+ or CD8+, and CD45RO, optionally lacking expression of CD45RA. Various memory T cell subsets have been identified and are each identified by their own distinguishing set of cell surface markers. Memory T cell subsets include, without limitation, central memory T cells, effector memory T cells, tissue resident memory T cells, virtual memory T cells, and stem memory T cells. Methods for further differentiation of memory T cells into the various memory T cell subsets are known to those of skill in the art, and will be recognized as an additional step in a method provided herein to further refine the population of memory T cells as such obtained.

CD4+ T cells assist other lymphocytes, for example, in the activation of cytotoxic T cells and macrophages. CD4+ T cells are characterized by cell surface expression of CD4 and are activated when naïve T cells interact with MHC class II molecules (e.g., an MHC class I molecule comprised by a modified cell of leukemic origin provided herein). CD4+ T cell subsets are known in the art and include, without limitation, Th1 cells, Th2 cells, Th17 cells, Th9 cells, and Tfh cells, and are characterized largely by the type of cytokines that are produced. For example, Th1 cells produce IFNγ, and Th2 cells produce IL-4. Cytotoxic CD8+ T cells are characterized by cell surface expression of CD8 and function to attack targets that express a cognate antigen. CD8+ T cells include, e.g., Tc cells, cytotoxic T-lymphocytes, T-killer cells, and killer T cells. CD8+ T cells recognize their targets by binding to short peptides associated with MHC class I molecules (e.g., an MHC class I molecule comprised by a modified cell of leukemic origin provided herein). CD8+ T cells are known to produce key cytokines such as IL-2 and IFNγ.

Accordingly, provided herein are methods for the combined stimulation of CD4+ and CD8+ immune cell (e.g., T cell) populations. In certain embodiments, provided herein is a method for generating a population of CD4+ and CD8+ T cells, comprising: obtaining a population of cells comprising immune cells (e.g., T cells); contacting the population of cells with a modified cell of leukemic origin; and culturing the population of cells under conditions suitable to stimulate proliferation of the immune cells, thereby generating the population of CD4+ and CD8+ T cells. In certain embodiments, provided herein is a method for generating a population of CD4+ T cells, comprising: obtaining a population of cells comprising immune cells (e.g., T cells); contacting the population of cells with a modified cell of leukemic origin; and culturing the population of cells under conditions suitable to stimulate proliferation of the immune cells, thereby generating the population of CD4+ T cells. In certain embodiments, provided herein is a method for generating a population of CD8+ T cells, comprising: obtaining a population of cells comprising immune cells (e.g., T cells); contacting the population of cells with a modified cell of leukemic origin; and culturing the population of cells under conditions suitable to stimulate proliferation of the immune cells, thereby generating the population of CD8+ T cells. Methods for further differentiation of CD4+ and/or CD8+ T cells into various T cell subsets are known to those of skill in the art, and will be recognized as an additional step in a method provided herein to further refine the population of CD4+ and/or CD8+ T cells as such obtained.

In the various methods provided herein for stimulating and expanding immune cells, conditions suitable to stimulate proliferation of the immune cells comprises providing signal-1 and signal-2 to the immune cells. In certain embodiments, signal-1 comprises activation of a TCR/CD3 complex. In certain embodiments, signal-2 comprises activation of a costimulatory molecule. It is believed that a modified cell of leukemic origin as described herein is capable of providing both signal-1 and signal-2 to the immune cells, and thus providing the conditions suitable for the immune cells to stimulate and expand.

In certain embodiments, the various methods provided utilize a modified cell of leukemic origin that comprises a mature dendritic cell phenotype. In certain exemplary embodiments, the modified cell of leukemic origin is non-proliferating (e.g., via irradiation).

The immune cells (e.g., T cells) are maintained under conditions necessary to support growth, for example, an appropriate temperature (e.g., 37° C.) and atmosphere (e.g., air plus 5% $CO_2$). Immune cells (e.g., T cells) that have been exposed to varied stimulation times may exhibit different characteristics.

The population of immune cells (e.g., T cells, memory T cells, CD4+/CD8+ T cells) generated by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the immune cells expand in the range of about 20 fold to about 50 fold.

Following culturing, the immune cells (e.g., T cells) can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. In certain exemplary embodiments, the level of confluence is 70% or greater before passing the cells to another culture apparatus. In certain exemplary embodiments, the level of confluence is 90% or greater. A period of time can be any time suitable for the culture of cells in vitro. The cell medium may be replaced during the culture of the immune cells at any time. In certain exemplary embodiments, the cell medium is replaced about every 2 to 3 days.

The immune cells are then harvested from the culture apparatus whereupon the immune cells can be used immediately or cryopreserved to be stored for use at a later time. In certain embodiments, methods provided herein further include cryopreserving the resulting immune cell population. In embodiments where the stimulated and expanded immune cells are for use in downstream modification, fresh or cryopreserved immune cells are prepared for the introduction of genetic material into the immune cells (e.g., nucleic acids encoding an immune receptor, e.g., TCR or CAR). In certain embodiments, cryopreserved immune cells are thawed prior to the introduction of genetic material. In certain embodiments, fresh or cryopreserved immune cells are prepared for electroporation with RNA encoding an immune receptor (e.g., TCR or CAR).

Another procedure for ex vivo expansion of immune cells is described in U.S. Pat. No. 5,199,942, the disclosure of which is incorporated by reference herein in its entirety. Methods for expanding and activating immune cells can also be found in U.S. Pat. Nos. 7,754,482, 8,722,400, and 9,555,105, the disclosures of which are incorporated herein in their entirety. Such art recognized expansion and activation methods can be an alternative or in addition to the methods described herein.

The culturing step (e.g., contact with a modified cell of leukemic origin as described herein) can be short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step (e.g., contact with a modified cell of leukemic origin as described herein) can be longer, for example 1, 2, 3, 4, 5, 6, 7, 8, 9, 10, 11, 12, 13, 14, or more days.

In certain embodiments, the cells may be cultured for several hours (about 3 hours) to about 14 days or any hourly integer value in between. Conditions appropriate for immune cell (e.g., T cell) culture include an appropriate media (e.g., Minimal Essential Media or RPMI Media 1640 or, X-vivo 15, (Lonza)) that may contain factors necessary for proliferation and viability, including serum (e.g., fetal bovine or human serum), insulin, IFNγ, interleukin-2 (IL-2), IL-4, IL-7, IL-10, IL-15, GM-CSF, TGFβ, and TNF-α, or any other additives for the growth of cells known to the skilled artisan. For example, other additives may include, without limitation, surfactant, plasmanate, and reducing agents such as N-acetyl-cysteine and 2-mercaptoethanol. Media can include RPMI 1640, AIM-V, DMEM, MEM, a-MEM, F-12, X-Vivo 10, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of immune cells. Antibiotics, e.g., penicillin and streptomycin, are included only in experimental cultures, not in cultures of cells that are to be infused into a subject.

D. Antigen-Specific Immune Cells

Also provided herein are methods for generating antigen-specific immune cells. Such methods utilize modified cells of leukemic origin as described herein. Accordingly, provided herein is a method for generating an antigen-specific immune cell, comprising inducing generation of the antigen-specific immune cell by contacting an immune cell with a modified cell of leukemic origin.

Antigen specificity of the immune cells generated by a method described herein may be directed to an antigen that is endogenous to the modified cell of leukemic origin. In certain embodiments, the modified cell of leukemic origin comprises an endogenous antigen selected from the group consisting of WT-1, RHAMM, PRAME, MUC-1, p53, Survivin, and any combination thereof. In certain embodiments, antigen specificity of the immune cells generated by a method described herein may be directed to an antigen that is exogenous to the modified cell of leukemic origin. An antigen exogenous to the modified cell of leukemic origin may be a tumor-associated antigen (TAA) or a non-tumor-associated antigen. In such embodiments, the method for generating an antigen-specific immune cell may comprise inducing generation of the antigen-specific immune cell by contacting an immune cell with a modified cell of leukemic origin comprising an exogenous antigen or peptide fragment thereof. In certain embodiments, the method for generating an antigen-specific immune cell comprises inducing generation of the antigen-specific immune cell by contacting an immune cell with a modified cell of leukemic origin, wherein the modified cell of leukemic origin has been loaded with an exogenous antigen or peptide fragment thereof. In certain embodiments, the antigen exogenous to the modified cell of leukemic origin is a non-tumor-associated antigen (e.g., a tumor-independent antigen). Tumor-independent antigens such as recall antigens are further described herein, and are also described in, e.g., U.S. Provisional Patent Application Ser. No. 63/110,046, filed Nov. 5, 2020, the disclosure of which is incorporated by reference herein in its entirety.

In certain embodiments, the specificity of antigen-specific immune cells may at least be in part the result of an antigen-specific immune receptor. The antigen-specific immune receptor may be endogenous (e.g., an antigen-specific T cell receptor derived from an endogenous T cell receptor repertoire), or exogenous (e.g., a chimeric antigen receptor specific for an antigen), and is specific to an antigen comprised by a modified cell of leukemic origin described herein. Various methods of modifying immune cells to comprise, e.g., an immune receptor, are known to those in the art. In certain embodiments, modification of an immune cell to comprise an immune receptor is mediated by a transposon or a viral vector. Transposon-based methods are described in, e.g., U.S. Pat. No. 10,513,686; US Patent Publication No. US20180002397A1; and PCT Publication Nos. WO2020014366A1; WO2019046815A1; and WO2019173636A1, the disclosures of which are herein incorporated by reference in their entireties.

In certain embodiments, the antigen can be introduced into a tumor cell, e.g., via a tumor-marking step as described herein.

E. T Cell Receptors

Provided herein are compositions and methods for modified immune cells or precursors thereof (e.g., modified T cells) comprising an immune receptor, wherein the immune receptor is a T cell receptor (TCR), e.g., an exogenous TCR. Thus, in some embodiments, the cell has been altered to contain specific T cell receptor (TCR) genes (e.g., a nucleic acid encoding an alpha/beta TCR). TCRs or antigen-binding portions thereof include those that recognize a peptide epitope or T cell epitope of a target polypeptide, such as an antigen of a tumor, viral or autoimmune protein. In certain embodiments, the TCR has binding specificity for a non-tumor-associated antigen. In certain embodiments, the TCR has binding specificity for a tumor-associated antigen (TAA). In certain embodiments, the antigen that the TCR is specific for, or is matched to, an antigen comprised by a tumor cell.

A TCR is a disulfide-linked heterodimeric protein comprised of six different membrane bound chains that participate in the activation of immune cells (e.g., T cells) in response to an antigen. Alpha/beta TCRs and gamma/delta TCRs are known. An alpha/beta TCR comprises a TCR alpha chain and a TCR beta chain. T cells expressing a TCR comprising a TCR alpha chain and a TCR beta chain are commonly referred to as alpha/beta T cells. Gamma/delta TCRs comprise a TCR gamma chain and a TCR delta chain. T cells expressing a TCR comprising a TCR gamma chain and a TCR delta chain are commonly referred to as gamma/delta T cells.

The TCR alpha chain and the TCR beta chain are each comprised of two extracellular domains, a variable region and a constant region. The TCR alpha chain variable region and the TCR beta chain variable region are required for the affinity of a TCR to a target antigen (e.g., a TAA, or non-tumor-associated antigen). Each variable region comprises three hypervariable or complementarity-determining regions (CDRs) which provide for binding to a target antigen. The constant region of the TCR alpha chain and the constant region of the TCR beta chain are proximal to the cell membrane. A TCR further comprises a transmembrane region and a short cytoplasmic tail. CD3 molecules are assembled together with the TCR heterodimer. CD3 molecules comprise a characteristic sequence motif for tyrosine phosphorylation, known as immunoreceptor tyrosine-based activation motifs (ITAMs). Proximal signaling events are mediated through the CD3 molecules, and accordingly, TCR-CD3 complex interaction plays an important role in mediating cell recognition events.

Stimulation of TCR is triggered by major histocompatibility complex molecules (MHCs) on antigen presenting cells that present antigen peptides to T cells and interact with TCRs to induce a series of intracellular signaling cascades. Engagement of the TCR initiates both positive and negative signaling cascades that result in cellular proliferation, cytokine production, and/or activation-induced cell death.

A TCR can be a wild-type TCR, a high affinity TCR, and/or a chimeric TCR. A high affinity TCR may be the result of modifications to a wild-type TCR that confers a higher affinity for a target antigen compared to the wild-type TCR. A high affinity TCR may be an affinity-matured TCR. In certain embodiments, it may be desired to obtain a TCR of lower affinity as compared to the wild-type TCR. Such lower affinity TCRs may also be referred to as affinity-tuned TCRs. Methods for modifying TCRs and/or the affinity-maturation/affinity-tuning of TCRs are known to those of skill in the art. Techniques for engineering and expressing TCRs include, but are not limited to, the production of TCR heterodimers which include the native disulfide bridge which connects the respective subunits (Garboczi, et al., (1996), Nature 384(6605): 134-41; Garboczi, et al., (1996), J Immunol 157(12): 5403-10; Chang et al., (1994), PNAS USA 91: 11408-11412; Davodeau et al., (1993), J. Biol. Chem. 268(21): 15455-15460; Golden et al., (1997), J. Imm. Meth. 206: 163-169; U.S. Pat. No. 6,080,840).

In certain embodiments, the exogenous TCR is a full TCR or an antigen-binding fragment thereof. In certain embodiments, the TCR is an intact or full-length TCR, including TCRs in the αβ form or γδ form. In certain embodiments, the TCR is an antigen-binding portion that is less than a full-length TCR but that binds to a specific peptide bound in an MHC molecule, such as binds to an MHC-peptide complex. In certain embodiments, an antigen-binding portion or fragment of a TCR can contain only a portion of the structural domains of a full-length or intact TCR, but yet is able to bind the peptide epitope, such as an MHC-peptide complex, to which the full TCR binds. In certain embodiments, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions (CDRs) involved in recognition of the peptide, MHC and/or MHC-peptide complex.

In certain embodiments, the variable domains of the TCR contain hypervariable loops, or CDRs, which generally are the primary contributors to antigen recognition and binding capabilities and specificity. In certain embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al, Proc. Nat'l Acad. Sci. U.S.A. 87:9138, 1990; Chothia et al., EMBO J. 7:3745, 1988; see also Lefranc et al., Dev. Comp. Immunol. 27:55, 2003). In certain embodiments, CDR3 is the main CDR responsible for antigen binding or specificity, or is the most important among the three CDRs on a given TCR variable region for antigen recognition, and/or for interaction with the processed peptide portion of the peptide-MHC complex. In certain embodiments, the CDR1 of the alpha chain can interact with the N-terminal part of certain antigenic peptides. In certain embodiments, CDR1 of the beta chain can interact with the C-terminal part of the peptide. In certain embodiments, CDR2 contributes most strongly to or is the primary CDR responsible for the interaction with or recognition of the MHC portion of the MHC-peptide complex. In certain embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In certain embodiments, a TCR contains a variable alpha domain ($V_\alpha$) and/or a variable beta domain ($V_\beta$) or antigen-binding fragments thereof. In certain embodiments, the α-chain and/or β-chain of a TCR also can contain a constant domain, a transmembrane domain and/or a short cytoplasmic tail (see, e.g., Janeway et al., Immunobiology: The Immune System in Health and Disease, 3 Ed., Current Biology Publications, p. 4:33, 1997). In certain embodiments, the α chain constant domain is encoded by the TRAC gene (IMGT nomenclature) or is a variant thereof. In certain embodiments, the β chain constant region is encoded by TRBC1 or TRBC2 genes (IMGT nomenclature) or is a variant thereof. In certain embodiments, the constant domain is adjacent to the cell membrane. For example, in certain embodiments, the extracellular portion of the TCR formed by the two chains contains two membrane-proximal constant domains, and two membrane-distal variable domains, which variable domains each contain CDRs.

It is within the level of a skilled artisan to determine or identify the various domains or regions of a TCR. In certain embodiments, residues of a TCR are known or can be identified according to the International Immunogenetics Information System (IMGT) numbering system (see e.g. www.imgt.org; see also, Lefranc et al. (2003) Developmental and Comparative Immunology, 2&; 55-77; and The T Cell Factsbook 2nd Edition, Lefranc and LeFranc Academic Press 2001). The IMGT numbering system should not be construed as limiting in any way, as there are other numbering systems known to those of skill in the art, and it is within the level of the skilled artisan to use any of the numbering systems available to identify the various domains or regions of a TCR.

In certain embodiments, the TCR may be a heterodimer of two chains α and β (or optionally γ and δ) that are linked, such as by a disulfide bond or disulfide bonds. In certain embodiments, the constant domain of the TCR may contain short connecting sequences in which a cysteine residue forms a disulfide bond, thereby linking the two chains of the TCR. In certain embodiments, a TCR may have an additional cysteine residue in each of the α and β chains, such that the TCR contains two disulfide bonds in the constant domains. In certain embodiments, each of the constant and variable domains contain disulfide bonds formed by cysteine residues.

In certain embodiments, the TCR is one generated from a known TCR sequence(s), such as sequences of Vα,β chains, for which a substantially full-length coding sequence is readily available. Methods for obtaining full-length TCR sequences, including V chain sequences, from cell sources are well known. In certain embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences. In certain embodiments, the TCR is obtained from a biological source, such as from cells such as from a T cell (e.g. cytotoxic T cell), T cell hybridomas or other publicly available source. In certain embodiments, the T cells can be obtained from in vivo isolated cells. In certain embodiments, the T cells can be obtained from a cultured T cell hybridoma or clone. In certain embodiments, the TCR or antigen-binding portion thereof can be synthetically generated from knowledge of the sequence of the TCR. In certain embodiments, a high-affinity T cell clone for a target antigen (e.g., a cancer antigen) is identified, isolated from a patient, and introduced into the cells. In certain embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15: 169-180 and Cohen et al. (2005) J Immunol. 175:5799-5808). In certain embodiments, phage display is used to isolate TCRs against a target antigen (see, e.g., Varela-Rohena et al. (2008) Nat Med. 14: 1390-1395 and Li (2005) Nat Biotechnol. 23:349-354).

In certain embodiments, the TCR or antigen-binding portion thereof is one that has been modified or engineered. In certain embodiments, directed evolution methods are used to generate TCRs with altered properties, such as with higher affinity for a specific MHC-peptide complex. In certain embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In certain embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In certain embodiments, the TCR can contain an introduced disulfide bond or bonds. In certain embodiments, the native disulfide bonds are not present. In certain embodiments, the one or more of the native cysteines (e.g. in the constant domain of the α chain and β chain) that form a native interchain disulfide bond are substituted with another residue, such as with a serine or alanine. In certain embodiments, an introduced disulfide bond can be formed by mutating non-cysteine residues on the alpha and beta chains, such as in the constant domain of the α chain and β chain, to cysteine. Exemplary non-native disulfide bonds of a TCR are described in PCT Publication Nos. WO2006/000830 and WO2006/037960, the disclosures of which are incorporated herein by reference in their entirety. In certain embodiments, cysteines can be introduced at residue Thr48 of the α chain and Ser57 of the β chain, at residue Thr45 of the α chain and Ser77 of the β chain, at residue Tyr10 of the α chain and Ser17 of the β chain, at residue Thr45 of the α chain and Asp59 of the β chain and/or at residue Ser15 of the α chain and GluI5 of the β chain. In certain embodiments, the presence of non-native cysteine residues (e.g. resulting in one or more non-native disulfide bonds) in a recombinant TCR can favor production of the desired recombinant TCR in a cell in which it is introduced over expression of a mismatched TCR pair containing a native TCR chain.

In certain embodiments, the TCR chains contain a transmembrane domain. In some embodiments, the transmembrane domain is positively charged. In certain embodiments, the TCR chain contains a cytoplasmic tail. In certain embodiments, each chain (e.g. alpha or beta) of the TCR can possess one N-terminal immunoglobulin variable domain, one immunoglobulin constant domain, a transmembrane region, and a short cytoplasmic tail at the C-terminal end. In certain embodiments, a TCR, for example via the cytoplasmic tail, is associated with invariant proteins of the CD3 complex involved in mediating signal transduction. In certain embodiments, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3y, CD35, CD3s and CD3ζ chains) contain one or more immunoreceptor tyrosine-based activation motif or ITAM that are involved in the signaling capacity of the TCR complex.

In certain embodiments, the TCR is a full-length TCR. In certain embodiments, the TCR is an antigen-binding portion. In certain embodiments, the TCR is a dimeric TCR (dTCR). In certain embodiments, the TCR is a single-chain TCR (sc-TCR). A TCR may be cell-bound or in soluble form. In certain embodiments, the TCR is in cell-bound form expressed on the surface of a cell. In certain embodiments, a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In certain embodiments, the bond can correspond to the native interchain disulfide bond present in native dimeric αβ TCRs. In certain embodiments, the interchain disulfide bonds are not present in a native TCR. For example, in certain embodiments, one or more cysteines can be incorporated into the constant region extracellular sequences of dTCR polypeptide pair. In certain embodiments, both a native and a non-native disulfide bond may be desirable. In certain embodiments, the TCR contains a transmembrane sequence to anchor to the membrane. In certain embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In certain embodiments, the TCR is an scTCR, which is a single amino acid strand containing an α chain and a β chain that is able to bind to MHC-peptide complexes. Typically, an scTCR can be generated using methods known to those of skill in the art, see, e.g., PCT Publication Nos. WO 96/13593, WO 96/18105, WO 99/18129, WO 04/033685, WO 2006/037960, WO 2011/044186; U.S. Pat. No. 7,569,664; and Schlueter, C. J. et al. J. Mol. Biol. 256, 859 (1996). In certain embodiments, an scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment. In certain embodiments, an scTCR contains a first segment constituted by an amino acid sequence corresponding to a TCR β chain variable region, a second segment constituted by an amino acid sequence corresponding to a TCR α chain variable region sequence fused to the N terminus of an amino acid sequence corresponding to a TCR α chain constant domain extracellular sequence, and a linker sequence linking the C terminus of the first segment to the N terminus of the second segment. In certain embodiments, an scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment. In certain embodiments, an scTCR contains a first segment constituted by a TCR β chain variable region sequence fused to the N terminus of a β chain extracellular constant domain sequence, and a second segment constituted by an α chain variable region sequence fused to the N terminus of a sequence comprising an α chain extracellular constant domain sequence and transmembrane sequence, and, optionally, a linker sequence linking the C terminus of the first segment to the N terminus of the second segment. In certain embodiments, for the scTCR to bind an MHC-peptide complex, the a and β chains must be paired so that the variable region sequences thereof are orientated for such binding. Various methods of promoting pairing of an α and β in an scTCR are well known in the art. In certain embodiments, a linker sequence is included that links the α and β chains to form the single polypeptide strand. In certain embodiments, the linker should have sufficient length to span the distance between the C terminus of the α chain and the N terminus of the β chain, or vice versa, while also ensuring that the linker length is not so long so that it blocks or reduces bonding of the scTCR to the target peptide-MHC complex. In certain embodiments, the linker of an scTCR that links the first and second TCR segments can be any linker capable of forming a single polypeptide strand, while retaining TCR binding specificity. In certain embodiments, the linker sequence may, for example, have the formula -P-AA-P-, wherein P is proline and AA represents an amino acid sequence wherein the amino acids are glycine and serine. In certain embodiments, the first and second segments are paired so that the variable region sequences thereof are orientated for such binding. In certain embodiments, the linker can contain from or from about 10 to 45 amino acids, such as 10 to 30 amino acids or 26 to 41 amino acids residues, for example 29, 30, 31 or 32 amino acids. In certain embodiments, an scTCR contains a disulfide bond between residues of the single amino acid strand, which, in some cases, can promote stability of the pairing between the α and β regions of the single chain molecule (see e.g. U.S. Pat. No. 7,569,664). In certain embodiments, the scTCR contains a covalent disulfide bond linking a residue of the immunoglobulin region of the constant domain of the α chain to a residue of the immunoglobulin region of the constant domain of the β chain of the single chain molecule. In certain embodiments, the disulfide bond corresponds to the native disulfide bond present in a native dTCR. In certain embodiments, the disulfide bond in a native TCR is not present. In certain embodiments, the disulfide bond is an introduced non-native disulfide bond, for example, by incorporating one or more cysteines into the constant region extracellular sequences of the first and second chain regions of the scTCR polypeptide. Exemplary cysteine mutations include any as described above. In some cases, both a native and a non-native disulfide bond may be present.

In certain embodiments, any of the TCRs, including a dTCR or an scTCR, can be linked to signaling domains that yield an active TCR on the surface of a T cell. In certain embodiments, the TCR is expressed on the surface of cells. In certain embodiments, the TCR contains a sequence corresponding to a transmembrane sequence. In certain embodiments, the transmembrane domain can be a Ca or CP transmembrane domain. In certain embodiments, the transmembrane domain can be from a non-TCR origin, for example, a transmembrane region from CD3z, CD28 or B7.1. In certain embodiments, the TCR contains a sequence corresponding to cytoplasmic sequences. In certain embodiments, the TCR contains a CD3z signaling domain. In certain embodiments, the TCR is capable of forming a TCR complex with CD3. In certain embodiments, the TCR or antigen binding portion thereof may be a recombinantly produced natural protein or mutated form thereof in which one or more property, such as binding characteristic, has been altered. In certain embodiments, a TCR may be derived from one of various animal species, such as human, mouse, rat, or other mammal.

In certain embodiments, the TCR has affinity to a target antigen on a target cell. The target antigen may include any type of protein, or epitope thereof, associated with the target cell. For example, the TCR may comprise affinity to a target antigen on a target cell that indicates a particular disease state of the target cell. In certain embodiments, the target antigen is processed and presented by MHCs.

In certain embodiments, the immune receptor (e.g., TCR) provides specificity to the immune cell towards a target antigen. In certain embodiments, the TCR (e.g., exogenous TCR) provided target antigen specificity is the same as the target antigen that the immune cell is specific for. In such embodiments, the TCR specificity is said to be matched with the endogenous specificity of the immune cell. In certain embodiments, the TCR (e.g., exogenous TCR) provided target antigen specificity is different to the target antigen that the immune cell is specific for. In such embodiments, the TCR specificity is said to be unmatched with the endogenous specificity of the immune cell. As such, a TCR having unmatched specificity with the endogenous specificity of the immune cell gives rise to a multispecific (e.g., bispecific) immune cell.

F. Chimeric Antigen Receptors

Provided herein are compositions comprising and methods for using modified immune cells or precursors thereof (e.g., modified T cells) comprising an immune receptor, wherein the immune receptor is a chimeric antigen receptor (CAR). Thus, in certain embodiments, the immune cell has been genetically modified to express the CAR. CARs of the present disclosure comprise an antigen binding domain, a transmembrane domain, and an intracellular domain.

The antigen binding domain may be operably linked to another domain of the CAR, such as the transmembrane domain or the intracellular domain, both described elsewhere herein, for expression in the cell. In certain embodiments, a first nucleic acid sequence encoding the antigen binding domain is operably linked to a second nucleic acid encoding a transmembrane domain, and further operably linked to a third a nucleic acid sequence encoding an intracellular domain. The antigen binding domains described herein can be combined with any of the transmembrane domains described herein, any of the intracellular domains or cytoplasmic domains described herein, or any of the other domains described herein that may be included in a CAR. In certain embodiments, a CAR may also include a hinge domain as described herein. In certain embodiments, a CAR may also include a spacer domain as described herein. In certain embodiments, each of the antigen binding domain, transmembrane domain, and intracellular domain is separated by a linker.

Antigen Binding Domain

The antigen binding domain of a CAR is an extracellular region of the CAR for binding to a specific target antigen including proteins, carbohydrates, and glycolipids. In certain embodiments, the CAR has affinity to a target antigen on a target cell. The target antigen may include any type of protein, or epitope thereof, associated with the target cell. For example, the CAR may have affinity to a target antigen on a target cell that indicates a particular disease state of the target cell.

Depending on the desired antigen to be targeted, the CAR can be engineered to include an appropriate antigen binding domain that is specific to the desired antigen target. In certain embodiments, such an antigen can be introduced into a tumor cell, e.g., via a tumor-marking step as described herein. In certain embodiments, the target cell antigen is a tumor-associated antigen (TAA). In certain embodiments, the target cell antigen is a non-tumor-associated antigen (non-TAA, e.g., a tumor independent antigen). A CAR having specificity for any target antigen is suitable for use in a method as provided herein. In certain embodiments, the antigen that the CAR is specific for is matched to an antigen expressed by a tumor cell.

In certain embodiments, the immune receptor (e.g., CAR) provides specificity to the immune cell towards a target antigen. In certain embodiments, the CAR provided target antigen specificity is the same as the target antigen that the immune cell is specific for. In such embodiments, the CAR specificity is said to be matched with the endogenous specificity of the immune cell. In certain embodiments, the CAR-provided target antigen specificity is different than the target antigen for which the immune cell is specific. In such embodiments, the CAR specificity is said to be unmatched with the endogenous specificity of the immune cell. As such, a CAR having unmatched specificity with the endogenous specificity of the immune cell gives rise to a multispecific (e.g., a bispecific) immune cell.

As described herein, a CAR having affinity for a specific target antigen on a target cell may comprise a target-specific binding domain. In certain embodiments, the target-specific binding domain is a murine target-specific binding domain, e.g., the target-specific binding domain is of murine origin. In certain embodiments, the target-specific binding domain is a human target-specific binding domain, e.g., the target-specific binding domain is of human origin.

In certain embodiments, a CAR may have affinity for one or more target antigens on one or more target cells. In certain embodiments, a CAR may have affinity for one or more target antigens on a target cell. In such embodiments, the CAR is a bispecific CAR, or a multispecific CAR. In certain embodiments, the CAR comprises one or more target-specific binding domains that confer affinity for one or more target antigens. In certain embodiments, the CAR comprises one or more target-specific binding domains that confer affinity for the same target antigen. For example, a CAR comprising one or more target-specific binding domains having affinity for the same target antigen could bind distinct epitopes of the target antigen. When a plurality of target-specific binding domains is present in a CAR, the binding domains may be arranged in tandem and may be separated by linker peptides. For example, in a CAR comprising two target-specific binding domains, the binding domains are connected to each other covalently on a single polypeptide chain, through an oligo linker or a polypeptide linker, an Fc hinge region, or a membrane hinge region.

In certain embodiments, the antigen binding domain is selected from the group consisting of an antibody, an antigen binding fragment (Fab), and a single-chain variable fragment (scFv). The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. In some embodiments, the antigen binding domain portion comprises a mammalian antibody or a fragment thereof. The choice of antigen binding domain may depend upon the type and number of antigens that are present on the surface of a target cell.

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker, which connects the N-terminus of the VH with the C-terminus of the VL, or the C-terminus of the VH with the N-terminus of the VL. In certain embodiments, the antigen binding domain (e.g., PSCA binding domain) comprises an scFv having the configuration from N-terminus to C-terminus, VH-linker-VL. In certain embodiments, the antigen binding domain comprises an scFv having the configuration from N-terminus to C-terminus, VL-linker-VH. Those of skill in the art would be able to select the appropriate configuration for use in the present disclosure.

The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. Various linker sequences are known in the art, including, without limitation, glycine serine (GS) linkers. Those of skill in the art would be able to select the appropriate linker sequence for use in the present disclosure. In certain embodiments, an antigen binding domain of the present disclosure comprises a heavy chain variable region (VH) and a light chain variable region (VL), wherein the VH and VL is separated by a GS linker sequence.

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hybridoma (Larchmt) 2008 27(6):455-51; Peter et al., J Cachexia Sarcopenia Muscle 2012 August 12; Shieh et al., J Immunol 2009 183(4):2277-85; Giomarelli et al., Thromb Haemost 2007 97(6):955-63; Fife et al., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Biol Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "Fab" refers to a fragment of an antibody structure that binds to an antigen but is monovalent and does not have a Fc portion, for example, an antibody digested by the enzyme papain yields two Fab fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

In certain embodiments, the antigen binding domain may be derived from the same species in which the immune cell may be administered to. For example, for use in humans, the antigen binding domain of the CAR may comprise a human antibody or a fragment thereof. In certain embodiments, the antigen binding domain may be derived from a different species in which the immune cell may be administered to. For example, for use in humans, the antigen binding domain of the CAR may comprise a murine antibody or a fragment thereof.

Transmembrane Domain

A CAR may comprise a transmembrane domain that connects the antigen binding domain of the CAR to the intracellular domain of the CAR. The transmembrane domain of a CAR is a region that is capable of spanning the plasma membrane of a cell (e.g., an immune cell or precursor thereof). The transmembrane domain is for insertion into a cell membrane, e.g., a eukaryotic cell membrane. In certain embodiments, the transmembrane domain is interposed between the antigen binding domain and the intracellular domain of a CAR.

In certain embodiments, the transmembrane domain is naturally associated with one or more of the domains in the CAR. In some embodiments, the transmembrane domain can be selected or modified by one or more amino acid substitutions to avoid binding of such domains to the transmembrane domains of the same or different surface membrane proteins, to minimize interactions with other members of the receptor complex.

The transmembrane domain may be derived either from a natural or a synthetic source. Where the source is natural, the domain may be derived from any membrane-bound or transmembrane protein, e.g., a Type I transmembrane protein. Where the source is synthetic, the transmembrane domain may be any artificial sequence that facilitates insertion of the CAR into a cell membrane, e.g., an artificial hydrophobic sequence. Examples of the transmembrane domain of particular use in this disclosure include, without limitation, transmembrane domains derived from (i.e. comprise at least the transmembrane region(s) of) the alpha, beta or zeta chain of the T cell receptor, CD28, CD3 epsilon, CD45, CD4, CD5, CD7, CD8, CD9, CD16, CD22, CD33, CD37, CD64, CD80, CD86, CD134 (OX-40), CD137 (4-1BB), CD154 (CD40L), Toll-like receptor 1 (TLR1), TLR2, TLR3, TLR4, TLR5, TLR6, TLR7, TLR8, and TLR9. In certain embodiments, the transmembrane domain may be synthetic, in which case it will comprise predominantly hydrophobic residues such as leucine and valine. In certain exemplary embodiments, a triplet of phenylalanine, tryptophan and valine will be found at each end of a synthetic transmembrane domain.

The transmembrane domains described herein can be combined with any of the antigen binding domains described herein, any of the intracellular domains described herein, or any of the other domains described herein that may be included in a CAR.

In certain embodiments, the transmembrane domain further comprises a hinge region. In certain embodiments, a CAR may also include a hinge region. The hinge region of the CAR is a hydrophilic region which is located between the antigen binding domain and the transmembrane domain. In certain embodiments, this domain facilitates proper protein folding for the CAR. The hinge region is an optional component for the CAR. The hinge region may include a domain selected from Fc fragments of antibodies, hinge regions of antibodies, CH2 regions of antibodies, CH3 regions of antibodies, artificial hinge sequences or combinations thereof. Examples of hinge regions include, without limitation, a CD8a hinge, artificial hinges made of polypeptides which may be as small as, three glycines (Gly), as well as CH1 and CH3 domains of IgGs (such as human IgG4).

In certain embodiments, a CAR includes a hinge region that connects the antigen binding domain with the transmembrane domain, which, in turn, connects to the intracellular domain. The hinge region is typically capable of supporting the antigen binding domain to recognize and bind to the target antigen on the target cells (see, e.g., Hudecek et al., *Cancer Immunol. Res.* (2015) 3(2): 125-135). In certain embodiments, the hinge region is a flexible domain, thus allowing the antigen binding domain to have a structure to optimally recognize the specific structure and density of the target antigens on a cell such as tumor cell. Id. The flexibility of the hinge region permits the hinge region to adopt many different conformations.

In certain embodiments, the hinge region is an immunoglobulin heavy chain hinge region. In certain embodiments, the hinge region is a hinge region polypeptide derived from a receptor (e.g., a CD8-derived hinge region).

The hinge region can have a length of from about 4 amino acids (aa) to about 50 amino acids (aa), e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa. In some embodiments, the hinge region can have a length of greater than 5 aa, greater than 10 aa, greater than 15 aa, greater than 20 aa, greater than 25 aa, greater than 30 aa, greater than 35 aa, greater than 40 aa, greater than 45 aa, greater than 50 aa, greater than 55 aa, or more.

Suitable hinge regions can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids. Suitable hinge regions can have a length of greater than 20 amino acids (e.g., 30, 40, 50, 60 or more amino acids).

For example, hinge regions include glycine polymers, glycine-serine polymers, glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see, e.g., Scheraga, *Rev. Computational. Chem.* (1992) 2: 73-142).

In certain embodiments, the hinge region is an immunoglobulin heavy chain hinge region. Immunoglobulin hinge region amino acid sequences are known in the art; see, e.g., Tan et al., *Proc. Natl. Acad. Sci. USA* (1990) 87(1):162-166; and Huck et al., *Nucleic Acids Res.* (1986) 14(4): 1779-1789.

The hinge region can comprise an amino acid sequence of a human IgG1, IgG2, IgG3, or IgG4, hinge region. In one embodiment, the hinge region can include one or more amino acid substitutions and/or insertions and/or deletions compared to a wild-type (naturally-occurring) hinge region. See, e.g., Yan et al., *J. Biol. Chem.* (2012) 287: 5891-5897.

Intracellular Signaling Domain

A CAR also includes an intracellular signaling domain. The terms "intracellular signaling domain" and "intracellular domain" are used interchangeably herein. The intracellular signaling domain of the CAR is responsible for activation of at least one of the effector functions of the cell in which the CAR is expressed (e.g., immune cell). The intracellular signaling domain transduces the effector function signal and directs the cell (e.g., immune cell) to perform its specialized function, e.g., harming and/or destroying a target cell.

Examples of an intracellular domain for use in the disclosure include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of the intracellular signaling domain include, without limitation, the ζ chain of the T cell receptor complex or any of its homologs, e.g., η chain, FcsRIγ and β chains, MB 1 (Iga) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.), and other molecules involved in T cell transduction, such as CD2, CD5 and CD28. In certain embodiments, the intracellular signaling domain may be human CD3 zeta chain, FcγRIII, FcsRI, cytoplasmic tails of Fc receptors, an immunoreceptor tyrosine-based activation motif (ITAM) bearing cytoplasmic receptors, and combinations thereof.

In certain embodiments, the intracellular signaling domain of the CAR includes any portion of one or more co-stimulatory molecules, such as at least one signaling domain from CD2, CD3, CD8, CD27, CD28, ICOS, 4-1BB, PD-1, any derivative or variant thereof, any synthetic sequence thereof that has the same functional capability, and any combination thereof.

Other examples of the intracellular domain include a fragment or domain from one or more molecules or receptors including, but not limited to, TCR, CD3 zeta, CD3 gamma, CD3 delta, CD3 epsilon, CD86, common FcR gamma, FcR beta (Fc Epsilon Rib), CD79a, CD79b, FcγRIIa, DAP10, DAP12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, CD49D, ITGA6, VLA-6, CD49f, ITGAD, CD11d, ITGAE, CD103, ITGAL, CD11a, LFA-1, ITGAM, CDlib, ITGAX, CD11c, ITGBI, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

Additional examples of intracellular domains include, without limitation, intracellular signaling domains of several types of various other immune signaling receptors, including, but not limited to, first, second, and third generation T cell signaling proteins including CD3, B7 family costimulatory, and Tumor Necrosis Factor Receptor (TNFR) superfamily receptors (see, e.g., Park and Brentjens, J. Clin. Oncol. (2015) 33(6): 651-653). Additionally, intracellular signaling domains may include signaling domains used by NK and NKT cells (see, e.g., Hermanson and Kaufman, Front. Immunol. (2015) 6: 195) such as signaling domains of NKp30 (B7-H6) (see, e.g., Zhang et al., J. Immunol. (2012) 189(5): 2290-2299), and DAP 12 (see, e.g., Topfer et al., J. Immunol. (2015) 194(7): 3201-3212), NKG2D, NKp44, NKp46, DAP10, and CD3z.

Intracellular signaling domains suitable for use in a subject CAR of the present disclosure include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the CAR (i.e., activated by antigen and dimerizing agent). In certain embodiments, the intracellular signaling domain includes at least one (e.g., one, two, three, four, five, six, etc.) ITAM motifs as described below. In certain embodiments, the intracellular signaling domain includes DAP10/CD28 type signaling chains. In certain embodiments, the intracellular signaling domain is not covalently attached to the membrane bound CAR, but is instead diffused in the cytoplasm.

Intracellular signaling domains suitable for use in a subject CAR of the present disclosure include immunoreceptor tyrosine-based activation motif (ITAM)-containing intracellular signaling polypeptides. In certain embodiments, an ITAM motif is repeated twice in an intracellular signaling domain, where the first and second instances of the ITAM motif are separated from one another by 6 to 8 amino acids. In certain embodiments, the intracellular signaling domain of a subject CAR comprises 3 ITAM motifs.

In certain embodiments, intracellular signaling domains includes the signaling domains of human immunoglobulin receptors that contain immunoreceptor tyrosine based activation motifs (ITAMs) such as, but not limited to, FcγRI, FcγRIIA, FcγRIIC, FcγRIIIA, and FcRL5 (see, e.g., Gillis et al., Front. Immunol. (2014) 5:254).

A suitable intracellular signaling domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12, FCER1G (Fc epsilon receptor I gamma chain), CD3D (CD3 delta), CD3E (CD3 epsilon), CD3G (CD3 gamma), CD3Z (CD3 zeta), and CD79A (antigen receptor complex-associated protein alpha chain).

In certain embodiments, the intracellular signaling domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). In certain embodiments, the intracellular signaling domain is derived from FCER1G (also known as FCRG; Fc epsilon receptor I gamma chain; Fc receptor gamma-chain; fc-epsilon RI-gamma; fcRγ; fceRIγ; high affinity immunoglobulin epsilon receptor subunit gamma; immunoglobulin E receptor, high affinity, gamma chain; etc.). In certain embodiments, the intracellular signaling domain is derived from T cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T cell receptor T3 delta chain; T cell surface glycoprotein CD3 delta chain; etc.). In certain embodiments, the intracellular signaling domain is derived from T cell surface glycoprotein CD3 epsilon chain (also known as CD3e, T cell surface antigen T3/Leu-4 epsilon chain, T cell surface glycoprotein CD3 epsilon chain, AI504783, CD3, CD3epsilon, T3e, etc.). In certain embodiments, the intracellular signaling domain is derived from T cell surface glycoprotein CD3 gamma chain (also known as CD3G, T cell receptor T3 gamma chain, CD3-GAMMA, T3G, gamma polypeptide (TiT3 complex), etc.). In certain embodiments, the intracellular signaling domain is derived from T cell surface glycoprotein CD3 zeta chain (also known as CD3Z, T cell receptor T3 zeta chain, CD247, CD3-ZETA, CD3H, CD3Q, T3Z, TCRZ, etc.). In certain embodiments, the intracellular signaling domain is derived from CD79A (also known as B cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). In certain embodiments, an intracellular signaling domain suitable for use in an FN3 CAR of the present disclosure includes a DAP10/CD28 type signaling chain. In certain embodiments, an intracellular signaling domain suitable for use in an FN3 CAR of the present disclosure includes a ZAP70 polypeptide. In certain embodiments, the intracellular signaling domain includes a cytoplasmic signaling domain of TCR zeta, FcR gamma, FcR beta, CD3 gamma, CD3 delta, CD3 epsilon, CD5, CD22, CD79a, CD79b, or CD66d. In certain embodiments, the intracellular signaling domain in the CAR includes a cytoplasmic signaling domain of human CD3 zeta.

While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The intracellular signaling domain includes any truncated portion of the intracellular signaling domain sufficient to transduce the effector function signal.

The intracellular signaling domains described herein can be combined with any of the antigen binding domains described herein, any of the transmembrane domains described herein, or any of the other domains described herein that may be included in the CAR.

G. Modified Immune Cells and Methods of Producing the Same

Provided herein are methods for expanding modified immune cells or precursors thereof (e.g., a T cell) comprising an immune receptor (e.g., a TCR or a CAR). Accordingly, such modified cells possess the specificity directed by the TCR and/or CAR that is expressed therein, and optionally in addition to the endogenous specificity provided by the immune cell.

Also provided are methods for producing or generating a modified immune cell or precursor thereof (e.g., a T cell). The cells generally are engineered by introducing one or more genetically engineered nucleic acids encoding the immune receptors (e.g., a TCR and/or a CAR).

In certain embodiments, the immune receptor (e.g., TCR and/or CAR) is introduced into a cell by an expression vector. Expression vectors comprising a nucleic acid sequence encoding a TCR and/or CAR are known in the art. Suitable expression vectors include lentivirus vectors, gamma retrovirus vectors, foamy virus vectors, adeno associated virus (AAV) vectors, adenovirus vectors, engineered hybrid viruses, naked DNA, including but not limited to transposon mediated vectors, such as Sleeping Beauty, piggyBac, and Integrases such as Phi31. Some other suitable expression vectors include Herpes simplex virus (HSV) and retrovirus expression vectors.

In certain embodiments, the nucleic acid encoding an immune receptor is introduced into the cell via viral transduction. In certain embodiments, the viral transduction comprises contacting the immune or precursor cell with a viral vector comprising the nucleic acid encoding the immune receptor.

Adenovirus expression vectors are based on adenoviruses, which have a low capacity for integration into genomic DNA but a high efficiency for transfecting host cells. Adenovirus expression vectors contain adenovirus sequences sufficient to: (a) support packaging of the expression vector and (b) to ultimately express the immune receptor in the host cell. In certain embodiments, the adenovirus genome is a 36 kb, linear, double stranded DNA, where a foreign DNA sequence (e.g., a nucleic acid encoding an exogenous TCR and/or CAR) may be inserted to substitute large pieces of adenoviral DNA in order to make the expression vector of the present disclosure (see, e.g., Danthinne and Imperiale, Gene Therapy (2000) 7(20): 1707-1714).

Another expression vector is based on an adeno associated virus (AAV), which takes advantage of the adenovirus coupled systems. This AAV expression vector has a high frequency of integration into the host genome. It can infect nondividing cells, thus making it useful for delivery of genes into mammalian cells, for example, in tissue cultures or in vivo. The AAV vector has a broad host range for infectivity. Details concerning the generation and use of AAV vectors are described in U.S. Pat. Nos. 5,139,941 and 4,797,368.

Retrovirus expression vectors are capable of integrating into the host genome, delivering a large amount of foreign genetic material, infecting a broad spectrum of species and cell types and being packaged in special cell lines. The retroviral vector is constructed by inserting a nucleic acid (e.g., a nucleic acid encoding an exogenous TCR and/or CAR) into the viral genome at certain locations to produce a virus that is replication defective. Though the retroviral vectors are able to infect a broad variety of cell types, integration and stable expression of the TCR and/or CAR requires the division of host cells.

Lentiviral vectors are derived from lentiviruses, which are complex retroviruses that, in addition to the common retroviral genes gag, pol, and env, contain other genes with regulatory or structural function (see, e.g., U.S. Pat. Nos. 6,013,516 and 5,994,136). Some examples of lentiviruses include the human immunodeficiency viruses (e.g., HIV-1, HIV-2) and the simian immunodeficiency virus (SIV). Lentiviral vectors have been generated by multiply attenuating the HIV virulence genes, for example, the genes env, vif, vpr, vpu and nef are deleted making the vector biologically safe. Lentiviral vectors are capable of infecting non-dividing cells and can be used for both in vivo and ex vivo gene transfer and expression, e.g., of a nucleic acid encoding a TCR and/or CAR (see, e.g., U.S. Pat. No. 5,994,136).

Expression vectors can be introduced into a host cell by any means known to persons skilled in the art. The expression vectors may include viral sequences for transfection, if desired. Alternatively, the expression vectors may be introduced by fusion, electroporation, biolistics, transfection, lipofection, or the like. The host cell may be grown and expanded in culture before introduction of the expression vectors, followed by the appropriate treatment for introduction and integration of the vectors. The host cells are then expanded and may be screened by virtue of a marker present in the vectors. Various markers that may be used are known in the art, and may include hprt, neomycin resistance, thymidine kinase, hygromycin resistance, etc. As used herein, the terms "cell," "cell line," and "cell culture" may be used interchangeably. In some embodiments, the host cell is an immune cell or precursor thereof, e.g., a T cell, an NK cell, or an NKT cell.

In certain embodiments, the modified immune cells are genetically engineered T lymphocytes (T cells), naive T cells, memory T cells (for example, central memory T cells (TCM), effector memory cells (TEM)), memory B cells, natural killer cells (NK cells), and macrophages capable of giving rise to therapeutically relevant progeny. In certain embodiments, the genetically engineered cells are autologous cells.

Modified immune cells (e.g., comprising a TCR and/or CAR) may be produced by stably transfecting host cells with an expression vector including a nucleic acid of the present disclosure. Additional methods for generating a modified cell of the present disclosure include, without limitation, chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). Transfected cells expressing an immune receptor may be expanded ex vivo.

Physical methods for introducing an expression vector into host cells include calcium phosphate precipitation, lipofection, particle bombardment, microinjection, electroporation, and the like. Methods for producing cells including vectors and/or exogenous nucleic acids are well-known in the art. See, e.g., Sambrook et al. (2001), Molecular Cloning: A Laboratory Manual, Cold Spring Harbor Laboratory, New York. Chemical methods for introducing an expression vector into a host cell include colloidal dispersion systems, such as macromolecule complexes, nanocapsules, microspheres, beads, and lipid-based systems including oil-in-water emulsions, micelles, mixed micelles, and liposomes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform may be used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). Compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the nucleic acids in the host cell, a variety of assays may be performed. Such assays include, for example, molecular biology assays well known to those of skill in the art, such as Southern and Northern blotting, RT-PCR and PCR; biochemistry assays, such as detecting the presence or absence of a particular peptide, e.g., by immunological means (ELISAs and Western blots) or by assays described herein to identify agents falling within the scope of the disclosure.

In one embodiment, the nucleic acids introduced into the host cell are RNA. In another embodiment, the RNA is mRNA that comprises in vitro transcribed RNA or synthetic RNA. The RNA may be produced by in vitro transcription using a polymerase chain reaction (PCR)-generated template. DNA of interest from any source can be directly converted by PCR into a template for in vitro mRNA synthesis using appropriate primers and RNA polymerase. The source of the DNA may be, for example, genomic DNA, plasmid DNA, phage DNA, cDNA, synthetic DNA sequence or any other appropriate source of DNA.

PCR may be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers may also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA typically has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

In certain embodiments, RNA is electroporated into the cells, such as in vitro transcribed RNA. Any solutes suitable for cell electroporation, which can contain factors facilitating cellular permeability and viability such as sugars, peptides, lipids, proteins, antioxidants, and surfactants can be included.

In some embodiments, a nucleic acid encoding an immune receptor is RNA, e.g., in vitro synthesized RNA. Methods for in vitro synthesis of RNA are known in the art; any known method can be used to synthesize RNA comprising a sequence encoding an immune receptor (e.g., TCR and/or CAR). Methods for introducing RNA into a host cell are known in the art. See, e.g., Zhao et al. Cancer Res. (2010) 15: 9053. Introducing RNA comprising a nucleotide sequence encoding a TCR and/or CAR into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding a TCR and/or CAR.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the disclosure is that RNA transfection is essentially transient and a vector-free. An RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this non-physiological overhang affects the amount of protein produced intracellularly from such a construct.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

In certain embodiments, the immune cells (e.g., T cells) can be incubated or cultivated prior to, during and/or subsequent to introducing the nucleic acid molecule encoding the immune receptor (e.g., the TCR and/or CAR). The cells (e.g., T cells) can be incubated or cultivated prior to, during or subsequent to the introduction of the nucleic acid molecule encoding the immune receptor, such as prior to, during or subsequent to the transduction of the cells with a viral vector (e.g. lentiviral vector) encoding the immune receptor. In certain embodiments, the method includes activating or stimulating cells with a stimulating or activating agent (e.g. a modified cell of leukemic origin) prior to introducing the nucleic acid molecule encoding the immune receptor. In certain embodiments, the method includes activating or stimulating cells with a stimulating or activating agent (e.g. a modified cell of leukemic origin) after introducing the nucleic acid molecule encoding the immune receptor.

H. Methods of Treatment

In certain embodiments, immune cells obtained according to the methods of the disclosure may be subsequently employed in an adoptive cell therapy. Adoptive cell therapy is an immunotherapy in which immune cells (e.g., T cells) are given to a subject to fight diseases, such as cancer. In general, T cells can be obtained from the subject's own peripheral blood or tumor tissue, stimulated and expanded ex vivo according to the methods of the disclosure, and then administered back to the subject (i.e., autologous adaptive cell therapy). In other embodiments, T cells can be obtained from a first subject (e.g., from peripheral blood or tumor tissue of the first subject), stimulated and expanded ex vivo according to the methods of the disclosure, and then administered to a second subject (i.e., allogeneic adaptive cell therapy).

In certain embodiments, the T cells can be further modified ex vivo (e.g., genetically modified) to express an immune receptor (e.g., a TCR and/or a CAR). The term "adoptive cell therapy" refers to both T cell therapy without genetic modification, and T cell therapy with genetic modification to, e.g., express an immune receptor.

As such, in certain embodiments, provided herein is a method for treating a disease or disorder in a subject in need thereof, comprising administering a composition comprising a modified immune cell of the disclosure, wherein the modified immune cell comprises an immune receptor. In certain embodiments, the immune receptor is a TCR and/or CAR as described elsewhere herein.

In certain embodiments, the disease or disorder is a cancer. In certain embodiments, the cancer is a tumor. In certain embodiments, the cancer is a liquid tumor, or a solid tumor.

In other aspects, provided herein is a method for treating a tumor in a subject in need thereof, comprising administering to the subject a modified immune cell produced by any one of the methods described herein.

In certain embodiments, the modified cell of leukemic origin comprising an exogenous antigen directs the specificity of the modified immune cell towards the exogenous antigen. In certain embodiments, this is achieved by redirecting the specificity of an immune receptor (e.g., an engineered immune receptor) comprised by the modified immune cell. In certain embodiments, the immune receptor may be an exogenous receptor, e.g., a chimeric antigen receptor comprising an antigen binding domain specific for the exogenous antigen, or an exogenous T cell receptor (TCR) directed to the exogenous antigen. In certain embodiments, the immune receptor may be an endogenous receptor, e.g., a natural receptor, e.g., a T cell receptor derived from a natural and/or endogenous TCR repertoire.

In certain embodiments, methods for treating a tumor provided herein further comprise a tumor-marking step. In certain embodiments, the tumor-marking step serves to mark the tumor with the exogenous antigen in order to redirect (e.g., recruit) the modified immune cells to the site of the tumor. In certain embodiments, the tumor-marking step comprises administering a composition comprising the exogenous antigen at the tumor site. In certain embodiments, administering the composition at the tumor site comprises intratumoral or peritumoral administration. In certain embodiments, administering the composition at the tumor site comprises administration into the tumor or proximal to the tumor. Various methods of marking a tumor are known to those of skill in the art. In addition to intratumoral delivery, the exogenous antigen may be delivered to the tumor via a tumor-specific carrier, such as an oncolytic virus or a gene therapy vector, which have been broadly developed to deliver gene sequences to tumors. The use of such vehicles allows for multiple routes of administration, in addition to intratumoral administration, such by as intravenous or intraperitoneal administration, subsequently resulting in the delivery of the nucleic acid encoding said polypeptide, into the tumor. Methods of tumor-marking are also described in PCT Application No. PCT/IB2020/053898 and PCT/NL19/50451, the disclosures of which are herein incorporated by reference in their entireties.

In certain embodiments, the tumor-marking step is performed before the modified immune cell is administered. Accordingly, provided herein is a method for treating a tumor in a subject in need thereof, comprising the following sequential steps: (1) administering to the subject a modified immune cell produced by any one of the methods described herein; and (2) a tumor-marking step comprising administering a composition to the subject at the tumor site, wherein the composition comprises an exogenous antigen or peptide fragments thereof.

In certain embodiments, the tumor-marking step is performed after the modified immune cell is administered. Accordingly, provided herein is a method for treating a tumor in a subject in need thereof, comprising the following sequential steps: (1) a tumor-marking step comprising administering a composition to the subject at the tumor site, wherein the composition comprises an exogenous antigen or peptide fragments thereof; and (2) administering to the subject a modified immune cell produced by any one of the methods described herein In certain embodiments, the composition administered in the tumor-marking step comprises the modified cell of leukemic origin used to direct the specificity of the modified immune cell. For example, the tumor-marking step comprises administering a composition to the subject at the tumor site, wherein the composition comprises a modified cell of leukemic origin, wherein the modified cell is non-proliferating, and wherein the modified cell comprises an exogenous antigen or peptide fragments thereof.

In certain embodiments, the modified cell of leukemic origin is a cell of cell line DCOne as described in PCT Publication Nos. WO 2014/006058 and WO 2014/090795, the disclosures of which are incorporated by reference herein in their entireties. In certain embodiments, modified cell of leukemic origin is a cell of cell line DCOne and comprises a mature dendritic cell phenotype (a DCOne mDC).

FIG. 1A shows that DCOne mDCs could be added at two different steps in a CAR T manufacturing process to: 1) Improve the enrichment and activation status of T cells (memory phenotype); 2) Induce additional tumor targeting specificity in the adoptive T cell pool (based on endogenous or exogenous antigens); and/or 3) Improve the expansion of CAR expressing T cells (phenotype, viability and CAR expression levels).

Figure 1B:
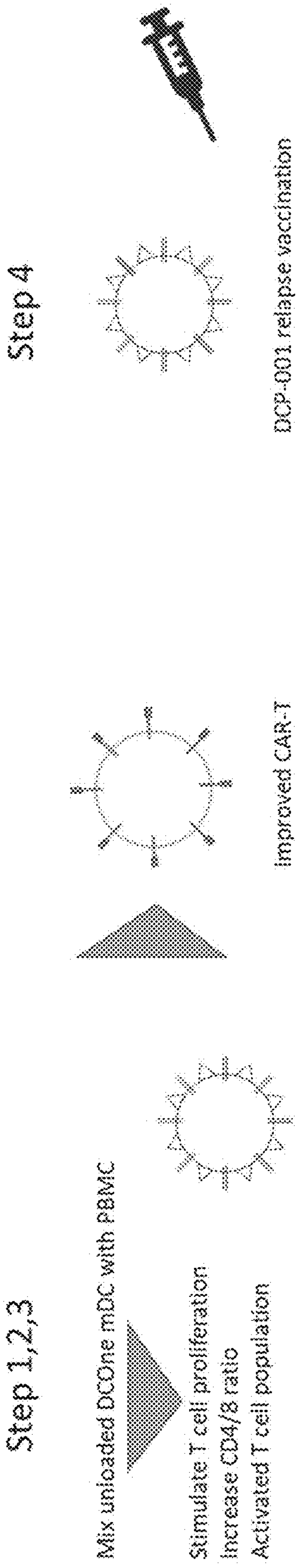
FIG. 1B is a schematic depicting the use of DCOne mDCs according to an embodiment of the disclosure.

As illustrated in FIG. 1B, in certain embodiments, a modified cell of leukemic origin (e.g., a DCOne mDC) is co-cultured with an immune cell (e.g., a T cell). The immune cell may be comprised within a population of peripheral blood mononuclear cells (PBMCs). In certain embodiments, a modified cell of leukemic origin (e.g., a DCOne mDC) is co-cultured with a T cell. In certain embodiments, co-culturing the modified cell of leukemic origin with the immune cell stimulates immune cell proliferation (e.g., T cell proliferation). In certain embodiments, co-culturing the modified cell of leukemic origin with the T cell stimulates T cell proliferation. Co-culturing the modified cell of leukemic origin with the immune cell results in an immune cell with improved properties. In certain embodiments, co-culturing the modified cell of leukemic origin with the T cell results in a T cell with improved properties. For example, in certain embodiments, co-culturing the modified cell of leukemic origin with the T cell increases the ratio of CD4+ to CD8+ T cells. In certain embodiments, co-culturing the modified cell of leukemic origin with the immune cell activates the immune cell. In certain embodiments, co-culturing the modified cell of leukemic origin with the T cell activates the T cell. Introducing an immune receptor (e.g., a CAR and/or TCR) into such an immune cell with improved properties, results in an improved modified immune cell (e.g., an improved CAR-T or an improved TCR-T cell). Such improved modified immune cells find use in adoptive cell therapies, resulting in improved adoptive cell therapies. In certain embodiments, a DCOne based vaccine (e.g., DCP-001 relapse vaccine) can be administered to a subject receiving an improved adoptive cell therapy as described herein. DCP-001 can further improve CAR-T function and survival, for example, by building immunological memory or boosting broader immune control over any residual disease.

In certain embodiments, a method of treating a disease or disorder (e.g., cancer) comprises the steps illustrated in FIG. 1B. For example, a method of treating a cancer (e.g., a solid tumor) comprises isolating PBMCs comprising T cells from a patient, co-culturing the isolated PBMCs with a modified cell of leukemic origin (e.g., a DCOne mDC) resulting in at least: 1) a stimulated T cell proliferation; 2) an increase in CD4+ to CD8+ T cell ratio; and/or 3) an activated T cell population, introducing an immune receptor (e.g., a CAR or a TCR) into the T cells to generate improved CAR-T or TCR-T cells, administering the improved CAR-T or TCR-T cells to the patient, and simultaneously or subsequently administering to the patient a DCOne based vaccine (e.g., a DCP-001 relapse vaccination) that provides improved adoptive cell therapy efficacy by improving CAR-T or TCR-T function and survival, improved immunological memory, and/or improved immune control over residual disease.

Figure 1C:
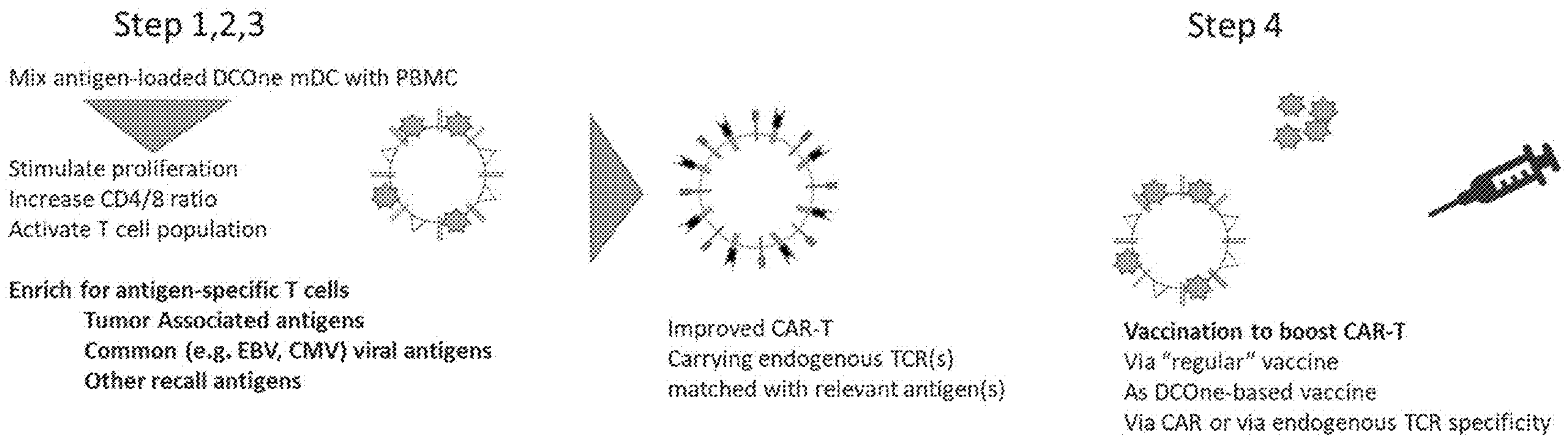
FIG. 1C is a schematic depicting the use of DCOne mDCs according to an embodiment of the disclosure.

FIG. 1C illustrates another embodiment of the disclosure. As shown, in certain embodiments, an antigen-loaded modified cell of leukemic origin (e.g., a DCOne mDC) is co-cultured with an immune cell (e.g., a T cell). The immune cell may be comprised within a population of peripheral blood mononuclear cells (PBMCs). In certain embodiments, an antigen-loaded modified cell of leukemic origin (e.g., a DCOne mDC) is co-cultured with a T cell. In certain embodiments, co-culturing the antigen-loaded modified cell of leukemic origin with the immune cell stimulates immune cell proliferation (e.g., T cell proliferation). In certain embodiments, co-culturing the antigen-loaded modified cell of leukemic origin with the T cell stimulates T cell proliferation.

Co-culturing the antigen-loaded modified cell of leukemic origin with the immune cell results in an immune cell with improved properties. In certain embodiments, co-culturing the antigen-loaded modified cell of leukemic origin with the T cell results in a T cell with improved properties. For example, in certain embodiments, co-culturing the antigen-loaded modified cell of leukemic origin with the T cell increases the ratio of CD4+ to CD8+ T cells. In certain embodiments, co-culturing the antigen-loaded modified cell of leukemic origin with the immune cell activates the immune cell. In certain embodiments, co-culturing the antigen-loaded modified cell of leukemic origin with the T cell activates the T cell. Use of an antigen-loaded modified cell of leukemic origin (e.g., an antigen-loaded DCOne mDC) provides additional improved qualities to the immune cell when co-cultured with the immune cell. For example, in certain embodiments, co-culturing immune cells with an antigen-loaded modified cell of leukemic origin enriches for antigen-specific immune cells. In certain embodiments, co-culturing T cells with an antigen-loaded modified cell of leukemic origin enriches for antigen-specific T cells.

It is readily appreciated by those of skill in the art that the antigen-loaded modified cell of leukemic origin can comprise any antigen. For example, an antigen-loaded modified cell of leukemic origin for use in the methods described herein can comprise, without limitation, a tumor-associated antigen, a non-tumor-associated antigen, a common viral antigen (e.g., an antigen derived from Epstein-Barr virus (EBV) or an antigen derived from cytomegalovirus (CMV)), or other recall antigens (e.g., CRM197). In certain embodiments, an antigen-loaded modified cell of leukemic origin for use in the methods described herein comprises an EBV derived antigen. In certain embodiments, an antigen-loaded modified cell of leukemic origin for use in the methods described herein comprises a CMV derived antigen. In certain embodiments, an antigen-loaded modified cell of leukemic origin for use in the methods described herein comprises a CRM197. In certain embodiments, an antigen-loaded modified cell of leukemic origin for use in the methods described herein comprises a recall antigen. Recall antigens are those which have previously been encountered by a host subject and for which there exists pre-existing memory lymphocytes (e.g., memory T cells and/or memory B cells) in the host. In certain embodiments, a recall antigen refers to a tumor-independent antigen for which pre-existing memory lymphocytes exist in the host. Pre-existing immune responses to recall antigens can exist as a result of prior infections or vaccinations. In certain embodiments, pre-existing immunity to a tumor-independent recall antigen is developed as a result of a prior infection, e.g., a viral infection. For example, cytomegalovirus (CMV) is commonly contracted without the subject knowing, as it rarely causes problems in healthy people. Subjects having had a prior CMV infection develop a strong immune response against CMV, resulting in having an immune system trained against CMV. As such, a tumor-independent antigen derived from CMV can be a recall antigen if used in a method to treat a subject having had a prior CMV infection. In certain embodiments, pre-existing immunity to a tumor-independent recall antigen is developed as a result of a vaccination. For example, CRM197 is widely used as an immunogenic adjuvant in conjugate vaccines. Subjects having had prior vaccination where CRM197 is used as an immunogenic adjuvant will have developed an immune response against CRM197, resulting in having an immune system trained against CRM197. Further, subjects having had prior vaccination where CRM197 is used in itself as a vaccine, e.g., against diphtheria, will have developed an immune response against CRM197, resulting in having an immune system trained against CRM197. Other recall antigens are known to those of skill in the art, for example, without limitation, carrier proteins, immunogenic adjuvants, and immunogens known in the vaccine arts, and viral, bacterial, and fungal infections that are encountered. As used herein, the term "carrier" refers to an immunogenic adjuvant and/or a carrier vehicle. For example, in the context of a conjugate vaccine, a carrier refers to a carrier protein onto which antigens are covalently conjugated thereto. In this context, the carrier is an immunogenic adjuvant acting to potentiate and/or modulate an immune response to an antigen. A carrier may also refer to a vehicle by which an antigen is delivered. For example, in certain embodiments described herein, an antigen is delivered via a tumor-specific carrier, such as an oncolytic virus or a gene therapy vector.

In certain embodiments, the antigen-loaded modified cell of leukemic origin redirects the specificity of the immune cell to the antigen. In certain embodiments, redirection of the specificity of the immune cell is accomplished by inducing the production of or enriching immune cells having endogenous TCRs directed to the antigen. As such, in certain embodiments, co-culturing an antigen-loaded modified cell of leukemic origin with an immune cell results in an immune cell comprising an endogenous TCR having specificity for the antigen.

In certain embodiments, introducing an immune receptor (e.g., a CAR and/or a TCR) into an immune cell that has been co-cultured with an antigen-loaded modified cell of leukemic origin, results in an improved modified immune cell (e.g., an improved CAR-T or an improved TCR-T cell). Such improved modified immune cells may comprise both the endogenous TCR that has been produced in response to the antigen-loaded modified cell of leukemic origin, and the immune receptor that has been introduced to the immune cell. In such cases, the improved modified immune cell may have specificity for one or more antigens. For example, the improved modified immune cell may have a first specificity as directed by the endogenous TCR (produced in response to the antigen-loaded modified cell of leukemic origin) and a second specificity as directed by the immune receptor (that has been introduced into the immune cell, e.g., a CAR and or a TCR). In certain embodiments, use of an antigen-loaded modified cell of leukemic origin in methods of treatment disclosed herein may result in recall antigen-specific memory T cells. In certain embodiments, use of an antigen-loaded modified cell of leukemic origin in methods of treatment disclosed herein may result in recall antigen-specific memory B cells. In certain embodiments, use of an antigen-loaded modified cell of leukemic origin in methods of treatment disclosed herein may result in virus-specific memory T cells. Use of virus-specific memory T cells for tumor immunotherapy has been described, see, e.g., Rosato et al., *Nature Communications* (2019) 10:567. In certain embodiments, use of an antigen-loaded modified cell of leukemic origin in methods of treatment disclosed herein may result in virus-specific memory B cells.

Such embodiments provide an adoptive cell therapy with improved efficacy. In certain embodiments, a vaccination (e.g., a DCOne based vaccine, e.g., a DCP-001 relapse vaccine) can be administered to a subject receiving an improved adoptive cell therapy as described herein, to boost the efficacy of the improved modified immune cells. Boosting of the efficacy of the improved modified immune cells can be achieved in at least the following manners: 1) a vaccination that provides an immunogen matched to the antigen that the endogenous TCR is directed to can stimulate the improved modified immune cell via the endogenous TCR; 2) a vaccination that provides an immunogen matched to the antigen that the immune receptor (e.g., CAR) is directed to can stimulate the improved modified immune cell via the immune receptor; and 3) a vaccination (e.g., a DCOne based vaccine) can further improve the function of the improved modified immune cell, for example, by building immunological memory or boosting broader immune control over any residual disease.

In certain embodiments, the improved modified immune cell comprises a "stronger" immune receptor, and a "weaker" immune receptor. The use of the terms stronger and weaker are not intended to qualify the actual strength of the immune receptors, but merely to illustrate the following concept. The "stronger" immune receptor, e.g., a CAR, when activated (i.e., when in contact with its cognate antigen), may result in a strong T cell response, e.g., a strong proliferative response, a strong cytotoxic response, etc. Due to this, the T cell that comprises the CAR may result in rapid T cell exhaustion (progressive loss of T cell functions) and can ultimately result in the destruction of the T cell via shifts in the balance between apoptotic and homeostatic regulatory factors. On the other hand, the "weaker" immune receptor, in certain embodiments, is activated by a recall antigen (e.g., a CMV derived antigen or an EBV derived antigen in a patient that has previously encountered CMV or EBV via infection or vaccination). As such, methods of the disclosure using a recall antigen-loaded modified cell of leukemic origin enriches for certain T cell populations that are able to respond to the recall antigen, e.g., certain T cell populations comprising endogenous TCRs that have been developed in response to the recall antigen. Such T cell populations are trained T cell populations as they have previously been developed due to the presence of the recall antigen, and comprise optimal immunity profiles, and are naturally viable populations. In certain embodiments, such T cell populations are naturally sustained, e.g., by chronic infections. In certain embodiments, use of improved modified immune cells that have been co-cultured with an antigen-loaded modified cell of leukemic origin (e.g., a recall antigen-loaded modified cell of leukemic origin) provides a stronger anti-tumor effect when compared to use of modified immune cells that have not been co-cultured with an antigen-loaded modified cell of leukemic origin.

In certain embodiments, a method of treating a disease or disorder (e.g., cancer) comprises the steps illustrated in FIG. 1C. For example, a method of treating a cancer (e.g., a solid tumor) comprises isolating PBMCs comprising T cells from a patient, co-culturing the isolated PBMCs with an antigen-loaded modified cell of leukemic origin (e.g., an antigen-loaded DCOne mDC, a recall antigen-loaded DCOne mDC) resulting in at least: 1) a stimulated T cell proliferation; 2) an increase in CD4+ to CD8+ T cell ratio; 3) an activated T cell population; and/or 4) enrichment for antigen-specific T cells (e.g., recall antigen-specific T cells), introducing an immune receptor (e.g., a CAR or a TCR) into the T cells to generate improved CAR-T or TCR-T cells, administering the improved CAR-T or TCR-T cells to the patient, and simultaneously or subsequently administering to the patient a vaccination (e.g., a DCOne based vaccine, a DCP-001 relapse vaccination) that provides improved adoptive cell therapy efficacy by improving CAR-T or TCR-T function and survival, improved immunological memory, and/or improved immune control over residual disease.

In certain embodiments, use of an antigen-loaded modified cell of leukemic origin (e.g., a tumor-independent antigen-loaded DCOne mDC) is in conjunction with any of the various methods described herein (e.g., tumor-marking methods).

In certain embodiments, a tumor-independent antigen-specific immune cell is generated by introducing into an immune cell a tumor-independent antigen or fragment thereof via the use of a photochemical processes (e.g., photochemical internalization). In certain embodiments, introducing into an immune cell a tumor-independent antigen or fragment thereof is achieved with the use of photochemical internalization. In certain embodiments, photochemical internalization may be used to enhance the delivery of an antigen or peptide fragments thereof (e.g., an antigenic polypeptide (e.g., a non-tumor antigen), or a nucleic acid encoding the antigenic polypeptide) into the modified cell of leukemic origin.

Photochemical internalization refers to a delivery method which involves the use of light and a photosensitizing agent for introducing otherwise membrane-impermeable molecules into the cytosol of a target cell, but which does not necessarily result in destruction or death of the target cell. In this method, the molecule to be internalized or transferred is applied to the cells in combination with a photosensitizing agent. Exposure of the cells to light of a suitable wavelength activates the photosensitizing agent which in turn leads to disruption of the intracellular compartment membranes and the subsequent release of the molecule into the cytosol. In photochemical internalization, the interaction between the photosensitizing agent and light is used to affect the cell such that intracellular uptake of the molecule is improved. Photochemical internalization as well as various photosensitizing agents are described in PCT Publication Nos. WO 96/07432, WO 00/54708, WO 01/18636, WO 02/44396, WO 02/44395, and WO 03/020309, U.S. Pat. Nos. 6,680, 301, 5,876,989, the disclosures of which are incorporated by reference herein in their entireties. In certain embodiments, photochemical internalization is used to deliver a tumor-independent antigen into the cytosol of a tumor cell. In certain embodiments, photochemical internalization is used to enhance the delivery of a tumor-independent antigen into the cytosol of a tumor cell.

Methods for administration of immune cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338. In certain embodiments, the cell therapy, e.g., adoptive T cell therapy is carried out by autologous transfer, in which the cells are isolated and/or otherwise prepared from the subject who is to receive the cell therapy, or from a sample derived from such a subject. Thus, in certain embodiments, the cells are derived from a subject, e.g., patient, in need of a treatment and the cells, following isolation and processing are administered to the same subject.

In certain embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In certain embodiments, the first and second subjects are genetically identical. In certain embodiments, the first and second subjects are genetically similar. In certain embodiments, the second subject expresses the same HLA class or supertype as the first subject.

In certain embodiments, the subject has been treated with a therapeutic agent targeting the disease or condition, e.g. the tumor, prior to administration of the cells or composition containing the cells. In certain embodiments, the subject is refractory or non-responsive to the other therapeutic agent. In certain embodiments, the subject has persistent or relapsed disease, e.g., following treatment with another therapeutic intervention, including chemotherapy, radiation, and/or hematopoietic stem cell transplantation (HSCT), e.g., allogenic HSCT. In certain embodiments, the administration effectively treats the subject despite the subject having become resistant to another therapy.

In certain embodiments, the subject is responsive to the other therapeutic agent, and treatment with the therapeutic agent reduces disease burden. In certain embodiments, the subject is initially responsive to the therapeutic agent, but exhibits a relapse of the disease or condition over time. In certain embodiments, the subject has not relapsed. In such embodiments, the subject is determined to be at risk for relapse, such as at a high risk of relapse, and thus the cells are administered prophylactically, e.g., to reduce the likelihood of or prevent relapse. In certain embodiments, the subject has not received prior treatment with another therapeutic agent.

In certain embodiments, the subject has persistent or relapsed disease, e.g., following treatment with another therapeutic intervention, including chemotherapy, radiation, and/or hematopoietic stem cell transplantation (HSCT), e.g., allogenic HSCT. In certain embodiments, the administration effectively treats the subject despite the subject having become resistant to another therapy.

The modified cell of leukemic origin and/or modified immune cells comprising an immune receptor can be administered to an animal, e.g., a mammal, e.g., a human, to treat a disease or disorder, e.g., a cancer. In addition, the cells of the present disclosure can be used for the treatment of any condition related to a cancer, especially a cell-mediated immune response against a tumor cell(s), where it is desirable to treat or alleviate the disease. The types of cancers to be treated using a method disclosed herein may be non-solid tumors (such as hematological tumors) or solid tumors. Adult tumors/cancers and pediatric tumors/cancers are also included. In certain embodiments, the cancer is a solid tumor or a hematological tumor. In certain embodiments, the cancer is a carcinoma. In certain embodiments, the cancer is a sarcoma. In certain embodiments, the cancer is a leukemia. In certain embodiments, the cancer is a solid tumor.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas).

The administration of the cells (e.g., a modified cell of leukemic origin, and/or a modified immune cell comprising an immune receptor) may be carried out in any convenient manner known to those of skill in the art. The cells may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In certain embodiments, the cells of the disclosure are injected directly into a site of inflammation in the subject, a local disease site in the subject, a lymph node, an organ, a tumor, and the like.

In certain embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio for immune cell administration. In certain embodiments, the dosage of cells is based on a desired total number (or number per kg of body weight) of cells in the individual populations or of individual cell types. In certain embodiments, the dosage is based on a combination of such features, such as a desired number of total cells, desired ratio, and desired total number of cells in the individual populations.

In certain embodiments, for the administration of immune cells, the populations or sub-types of cells, such as CD8+ and CD4+ T cells, are administered at or within a tolerated difference of a desired dose of total cells, such as a desired dose of T cells.

In certain embodiments, the desired dose is a desired number of cells or a desired number of cells per unit of body weight of the subject to whom the cells are administered, e.g., cells/kg. In certain embodiments, the desired dose is at or above a minimum number of cells or minimum number of cells per unit of body weight. In certain embodiments, among the total cells, administered at the desired dose, the individual populations or sub-types are present at or near a desired output ratio (such as CD4+ to CD8+ ratio), e.g., within a certain tolerated difference or error of such a ratio.

In certain embodiments, the cells are administered at or within a tolerated difference of a desired dose of one or more of the individual populations or sub-types of cells, such as a desired dose of CD4+ cells and/or a desired dose of CD8+ cells. In certain embodiments, the desired dose is a desired number of cells of the sub-type or population, or a desired number of such cells per unit of body weight of the subject to whom the cells are administered, e.g., cells/kg. In certain embodiments, the desired dose is at or above a minimum number of cells of the population or subtype, or minimum number of cells of the population or sub-type per unit of body weight. Thus, in certain embodiments, the dosage is based on a desired fixed dose of total cells and a desired ratio, and/or based on a desired fixed dose of one or more, e.g., each, of the individual sub-types or sub-populations. Thus, in certain embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In certain embodiments, the cells (e.g., modified cells of leukemic origin, and/or immune cells comprising an immune receptor), or individual populations of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, about 50 million cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In certain embodiments, the dose of total cells (e.g., modified cells of leukemic origin, and/or immune cells comprising an immune receptor) and/or dose of individual sub-populations of cells is within a range of between at or about $1\times10^5$ cells/kg to about $1\times10^{11}$ cells/kg $10^4$ and at or about $10^{11}$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight. For example, in certain embodiments, the cells are administered at, or within a certain range of error of, between at or about $10^4$ and at or about $10^9$ T cells/kilograms (kg) body weight, such as between $10^5$ and $10^6$ T cells/kg body weight, for example, at or about $1\times10^5$ T cells/kg, $1.5\times10^5$ T cells/kg, $2\times10^5$ T cells/kg, or $1\times10^6$ T cells/kg body weight. In certain embodiments, a suitable dosage range of cells for use in a method provided herein includes, without limitation, from about $1\times10^5$ cells/kg to about $1\times10^6$ cells/kg, from about $1\times10^6$ cells/kg to about $1\times10^7$ cells/kg, from about $1\times10^7$ cells/kg about $1\times10^8$ cells/kg, from about $1\times10^8$ cells/kg about $1\times10^9$ cells/kg, from about $1\times10^9$ cells/kg about $1\times10^{10}$ cells/kg, from about $1\times10^{10}$ cells/kg about $1\times10^{11}$ cells/kg.

In certain embodiments, the cells (e.g., immune cells comprising an immune receptor) are administered at or within a certain range of error of between at or about $10^4$ and at or about $10^9$ $CD4^+$ and/or $CD8^+$ cells/kilograms (kg) body weight, such as between $10^5$ and $10^6$ $CD4^+$ and/or $CD8^+$ cells/kg body weight, for example, at or about $1\times10^5$ $CD4^+$ and/or $CD8^+$ cells/kg, $1.5\times10^5$ $CD4^+$ and/or $CD8^+$ cells/kg, $2\times10^5$ $CD4^+$ and/or $CD8^+$ cells/kg, or $1\times10^6$ $CD4^+$ and/or $CD8^+$ cells/kg body weight. In certain embodiments, the cells are administered at or within a certain range of error of, greater than, and/or at least about $1\times10^6$, about $2.5\times10^6$, about $5\times10^6$, about $7.5\times10^6$, or about $9\times10^6$ $CD4^+$ cells, and/or at least about $1\times10^6$, about $2.5\times10^6$, about $5\times10^6$, about $7.5\times10^6$, or about $9\times10^6$ $CD8^+$ cells, and/or at least about $1\times10^6$, about $2.5\times10^6$, about $5\times10^6$, about $7.5\times10^6$, or about $9\times10^6$ T cells. In certain embodiments, the cells are administered at or within a certain range of error of between about $10^8$ and $10^{12}$ or between about $10^{10}$ and $10^{11}$ T cells, between about $10^8$ and $10^{12}$ or between about $10^{10}$ and $10^{11}$ $CD4^+$ cells, and/or between about $10^8$ and $10^{12}$ or between about $10^{10}$ and $10^{11}$ $CD8^+$ cells.

In certain embodiments, for the administration of immune cells (e.g., immune cells comprising an immune receptor), the cells are administered at or within a tolerated range of a desired output ratio of multiple cell populations or sub-types, such as CD4+ and CD8+ cells or sub-types. In certain embodiments, the desired ratio can be a specific ratio or can be a range of ratios, for example, in some embodiments, the desired ratio (e.g., ratio of CD4+ to CD8+ cells) is between at or about 1:5 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In certain embodiments, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In certain embodiments, a dose of immune cells is administered to a subject in need thereof, in a single dose or multiple doses. In certain embodiments, a dose of cells is administered in multiple doses, e.g., once a week or every 7 days, once every 2 weeks or every 14 days, once every 3 weeks or every 21 days, once every 4 weeks or every 28 days.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In certain embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in certain embodiments are co-administered with one or more additional therapeutic agents or in connection with another therapeutic intervention, either simultaneously or sequentially in any order. In certain embodiments, the cells are co-administered with another therapy sufficiently close in time such that the cell populations enhance the effect of one or more additional therapeutic agents, or vice versa. In certain embodiments, the cells are administered prior to the one or more additional therapeutic agents. In certain embodiments, the cells are administered after the one or more additional therapeutic agents. In certain embodiments, the one or more additional agents includes a cytokine, such as IL-2, for example, to enhance persistence. In certain embodiments, the methods comprise administration of a chemotherapeutic agent.

Following administration of the cells, the biological activity of the engineered cell populations in some embodiments is measured, e.g., by any of a number of known methods. Parameters to assess include specific binding of an modified or natural T cell or other immune cell to antigen, in vivo, e.g., by imaging, or ex vivo, e.g., by ELISA or flow cytometry. In certain embodiments, the ability of the modified immune cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNγ, IL-2, and TNF. In certain embodiments the biological activity is measured by assessing clinical outcome, such as reduction in tumor burden or load, or reduction in the occurrence of relapse.

In certain embodiments, the subject is provided a secondary treatment. Secondary treatments include but are not limited to chemotherapy, radiation, surgery, and medications.

In certain embodiments, the subject can be administered conditioning therapy prior to adoptive cell therapy. In certain embodiments, the conditioning therapy comprises administering an effective amount of cyclophosphamide to the subject. In certain embodiments, the conditioning therapy comprises administering an effective amount of fludarabine to the subject. In certain embodiments, the conditioning therapy comprises administering an effective amount of a combination of cyclophosphamide and fludarabine to the subject. Administration of a conditioning therapy prior to adoptive cell therapy may increase the efficacy of the adoptive cell therapy. Methods of conditioning patients for adoptive cell therapy are described in U.S. Pat. No. 9,855,298, which is incorporated herein by reference in its entirety.

Cells of the disclosure can be administered in dosages and routes and at times to be determined in appropriate preclinical and clinical experimentation and trials. Cell compositions may be administered multiple times at dosages within these ranges. Administration of the cells of the disclosure may be combined with other methods useful to treat the desired disease or condition as determined by those of skill in the art.

It is known in the art that one of the adverse effects following infusion of CAR T cells is the onset of immune activation, known as cytokine release syndrome (CRS). CRS is immune activation resulting in elevated inflammatory cytokines. CRS is a known on-target toxicity, development of which likely correlates with efficacy. Clinical and laboratory measures range from mild CRS (constitutional symptoms and/or grade-2 organ toxicity) to severe CRS (sCRS; grade organ toxicity, aggressive clinical intervention, and/or potentially life threatening). Clinical features include: high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T cell infusion. One CRS signature is elevation of cytokines including IL-6 (severe elevation), IFN-gamma, TNF-alpha (moderate), and IL-2 (mild). Elevations in clinically available markers of inflammation including ferritin and C-reactive protein (CRP) have also been observed to correlate with the CRS syndrome. The presence of CRS generally correlates with expansion and progressive immune activation of adoptively transferred cells. It has been demonstrated that the degree of CRS severity is dictated by disease burden at the time of infusion as patients with high tumor burden experience a more sCRS.

Accordingly, the present disclosure provides for, following the diagnosis of CRS, appropriate CRS management strategies to mitigate the physiological symptoms of uncontrolled inflammation without dampening the antitumor efficacy of the engineered cells (e.g., CART cells). CRS management strategies are known in the art. For example, systemic corticosteroids may be administered to rapidly reverse symptoms of sCRS (e.g., grade 3 CRS) without compromising initial antitumor response.

In some embodiments, an anti-IL-6R antibody may be administered. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administration of tocilizumab has demonstrated near-immediate reversal of CRS.

CRS is generally managed based on the severity of the observed syndrome and interventions are tailored as such. CRS management decisions may be based upon clinical signs and symptoms and response to interventions, not solely on laboratory values alone.

Mild to moderate cases generally are treated with symptom management with fluid therapy, non-steroidal anti-inflammatory drug (NSAID) and antihistamines as needed for adequate symptom relief. More severe cases include patients with any degree of hemodynamic instability. With any hemodynamic instability, the administration of tocilizumab is typically recommended. The first-line management of CRS may be tocilizumab, in some embodiments, at the labeled dose of 8 mg/kg IV over 60 minutes (not to exceed 800 mg/dose). Tocilizumab treatment can be repeated Q8 hours. If a suboptimal response is achieved after the first dose of tocilizumab, additional doses of tocilizumab may be considered. Tocilizumab can be administered alone or in combination with corticosteroid therapy. Patients with continued or progressive CRS symptoms, inadequate clinical improvement in 12-18 hours, or poor response to tocilizumab, may be treated with high-dose corticosteroid therapy, generally hydrocortisone 100 mg IV or methylprednisolone 1-2 mg/kg. In patients with more severe hemodynamic instability or more severe respiratory symptoms, patients may be administered high-dose corticosteroid therapy early in the course of the CRS. CRS management guidance may be based on published standards (Lee et al. (2019) *Biol Blood Marrow Transplant*, doi.org/10.1016/j.bbmt.2018.12.758; Neelapu et al. (2018) *Nat Rev Clin Oncology,* 15:47; Teachey et al. (2016) *Cancer Discov,* 6(6):664-679).

Features consistent with macrophage activation syndrome (MAS) or hemophagocytic lymphohistiocytosis (HLH) have been observed in patients treated with CAR-T therapy (Henter, 2007), coincident with clinical manifestations of the CRS. MAS appears to be a reaction to immune activation that occurs from the CRS, and should therefore be considered a manifestation of CRS. MAS is similar to HLH (also a reaction to immune stimulation). The clinical syndrome of MAS is characterized by high grade non-remitting fever, cytopenias affecting at least two of three lineages, and hepatosplenomegaly. It is associated with high serum ferritin, soluble interleukin-2 receptor, and triglycerides, and a decrease of circulating natural killer (NK) activity.

I. Sources of Immune Cells

Prior to expansion, a source of immune cells is obtained from a subject for ex vivo manipulation. Sources of target cells for ex vivo manipulation may also include, e.g., autologous or heterologous donor blood, cord blood, or bone marrow. For example, the source of immune cells may be from the subject to be treated with the modified immune cells of the disclosure, e.g., the subject's blood, the subject's cord blood, or the subject's bone marrow. Non-limiting examples of subjects include humans, dogs, cats, mice, rats, and transgenic species thereof. In certain exemplary embodiments, the subject is a human.

Immune cells can be obtained from a number of sources, including blood, peripheral blood mononuclear cells, bone marrow, lymph node tissue, spleen tissue, umbilical cord, lymph, or lymphoid organs. Immune cells are cells of the immune system, such as cells of the innate or adaptive immunity, e.g., myeloid or lymphoid cells, including lymphocytes, typically T cells and/or NK cells. Other exemplary cells include stem cells, such as multi potent and pluripotent stem cells, including induced pluripotent stem cells (iPSCs). In certain embodiments, the cells are human cells. With reference to the subject to be treated, the cells may be allogeneic and/or autologous. The cells typically are primary cells, such as those isolated directly from a subject and/or isolated from a subject and frozen.

In certain embodiments, the immune cell is a T cell, e.g., a CD8+ T cell (e.g., a CD8+ naive T cell, central memory T cell, or effector memory T cell), a CD4+ T cell, a natural killer T cell (NKT cells), a regulatory T cell (Treg), a stem cell memory T cell, a lymphoid progenitor cell a hematopoietic stem cell, a natural killer cell (NK cell) or a dendritic cell. In certain embodiments, the cells are monocytes or granulocytes, e.g., myeloid cells, macrophages, neutrophils, dendritic cells, mast cells, eosinophils, and/or basophils. In certain embodiments, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a CD8+ T cell (e.g., a CD8+ naive T cell, central memory T cell, or effector memory T cell), a CD4+ T cell, a stem cell memory T cell, a lymphoid progenitor cell or a hematopoietic stem cell.

In certain embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen specificity, type of antigen receptor, presence in a particular organ or compartment, marker or cytokine secretion profile, and/or degree of differentiation. Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as Th1 cells, Th2 cells, Th3 cells, Th17 cells, Th9 cells, Th22 cells, follicular helper T cells, alpha/beta T cells, and delta/gamma T cells. In certain embodiments, any number of T cell lines available in the art, may be used.

In certain embodiments, the methods include isolating immune cells from the subject, preparing, processing, culturing, and/or engineering them. In certain embodiments, preparation of the engineered cells includes one or more culture and/or preparation steps. The cells for engineering as described may be isolated from a sample, such as a biological sample, e.g., one obtained from or derived from a subject. In certain embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In certain embodiments, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In certain embodiments, the cells are derived from cell lines, e.g., T cell lines. The cells in certain embodiments are obtained from a xenogeneic source, for example, from mouse, rat, non-human primate, and pig. In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In certain embodiments, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets. In certain embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In certain embodiments, a washing step is accomplished by tangential flow filtration (TFF) according to the manufacturer's instructions. In certain embodiments, the cells are resuspended in a variety of biocompatible buffers after washing. In certain embodiments, components of a blood cell sample are removed and the cells directly resuspended in culture media. In certain embodiments, the methods include density-based cell separation methods, such as the preparation of white blood cells from peripheral blood by lysing the red blood cells and centrifugation through a Percoll or Ficoll gradient.

In certain embodiments, immune cells are obtained cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In certain embodiments, the isolation methods include the separation of different cell types based on the expression or presence in the cell of one or more specific molecules, such as surface markers, e.g., surface proteins, intracellular markers, or nucleic acid. In certain embodiments, any known method for separation based on such markers may be used. In certain embodiments, the separation is affinity- or immunoaffinity-based separation. For example, the isolation in certain embodiments includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In certain embodiments, both fractions are retained for further use. In certain embodiments, negative selection can be particularly useful where no antibody is available that specifically identifies a cell type in a heterogeneous population, such that separation is best carried out based on markers expressed by cells other than the desired population. The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In certain embodiments, multiple rounds of separation steps are carried out, where the positively or negatively selected fraction from one step is subjected to another separation step, such as a subsequent positive or negative selection. In certain embodiments, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In certain embodiments, one or more of the T cell populations is enriched for or depleted of cells that are positive for (marker+) or express high levels ($marker^{high}$) of one or more particular markers, such as surface markers, or that are negative for (marker−) or express relatively low levels ($marker^{low}$) of one or more markers. For example, in certain embodiments, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In certain embodiments, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD 127, and/or CD62L and/or depleted of (e.g., negatively selected for) cells that are positive for or express high surface levels of CD45RA. In certain embodiments, cells are enriched for or depleted of cells positive or expressing high surface levels of CD 122, CD95, CD25, CD27, and/or IL7-Ra (CD 127). In certain embodiments, CD8+ T cells are enriched for cells positive for CD45RO (or negative for CD45RA) and for CD62L. For example, CD3+, CD28+ T cells can be positively selected using CD3/CD28 conjugated magnetic beads (e.g., DYNABEADS® M-450 CD3/CD28 T Cell Expander).

In certain embodiments, T cells are separated from a PBMC sample by negative selection of markers expressed on non-T cells, such as B cells, monocytes, or other white blood cells, such as CD14. In certain embodiments, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations. In certain embodiments, CD8+ cells are further enriched for or depleted of naive, central memory, effector memory, and/or central memory stem cells, such as by positive or negative selection based on surface antigens associated with the respective subpopulation. In certain embodiments, enrichment for central memory T (Tcm) cells is carried out to increase efficacy, such as to improve long-term survival, expansion, and/or engraftment following administration, which in some aspects is particularly robust in such sub-populations. In certain embodiments, combining Tcm-enriched CD8+ T cells and CD4+ T cells further enhances efficacy.

In certain embodiments, memory T cells are present in both CD62L+ and CD62L− subsets of CD8+ peripheral blood lymphocytes. PBMC can be enriched for or depleted of CD62L-CD8+ and/or CD62L+CD8+ fractions, such as using anti-CD8 and anti-CD62L antibodies. In certain embodiments, a CD4+ T cell population and a CD8+ T cell sub-population, e.g., a sub-population enriched for central memory (Tcm) cells. In certain embodiments, the enrichment for central memory T (Tcm) cells is based on positive or high surface expression of CD45RO, CD62L, CCR7, CD28, CD3, and/or CD 127; in some aspects, it is based on negative selection for cells expressing or highly expressing CD45RA and/or granzyme B. In certain embodiments, isolation of a CD8+ population enriched for TCM cells is carried out by depletion of cells expressing CD4, CD14, CD45RA, and positive selection or enrichment for cells expressing CD62L. In certain embodiments, enrichment for central memory T (Tcm) cells is carried out starting with a negative fraction of cells selected based on CD4 expression, which is subjected to a negative selection based on expression of CD14 and CD45RA, and a positive selection based on CD62L. Such selections in certain embodiments are carried out simultaneously and in other aspects are carried out sequentially, in either order. In certain embodiments, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

CD4+ T helper cells are sorted into naive, central memory, and effector cells by identifying cell populations that have cell surface antigens. CD4+ lymphocytes can be obtained by standard methods. In certain embodiments, naive CD4+ T lymphocytes are CD45RO−, CD45RA+, CD62L+, CD4+ T cells. In certain embodiments, central memory CD4+ cells are CD62L+ and CD45RO+. In certain embodiments, effector CD4+ cells are CD62L− and CD45RO. In one example, to enrich for CD4+ cells by negative selection, a monoclonal antibody cocktail typically includes antibodies to CD14, CD20, CD11b, CD16, HLA-DR, and CD8. In certain embodiments, the antibody or binding partner is bound to a solid support or matrix, such as a magnetic bead or paramagnetic bead, to allow for separation of cells for positive and/or negative selection.

In certain embodiments, the cells are incubated and/or cultured prior to or in connection with genetic engineering. The incubation steps can include culture, cultivation, stimulation, activation, and/or propagation. In certain embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In certain embodiments, the stimulating agents include IL-2, IL-7, IL-15 and/or IL-21, for example, an IL-2 concentration of at least about 10 units/mL.

In certain embodiments, T cells are isolated from peripheral blood by lysing the red blood cells and depleting the monocytes, for example, by centrifugation through a PERCOLL™ gradient. Alternatively, T cells can be isolated from an umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19, and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in certain embodiments, a concentration of 2 billion cells/mi is used. In one embodiment, a concentration of 1 billion cells/mi is used. In a further embodiment, greater than 100 million cells/mi is used. In a further embodiment, a concentration of cells of 10, 15, 20, 25, 30, 35, 40, 45, or 50 million cells/mi is used. In yet another embodiment, a concentration of cells from 75, 80, 85, 90, 95, or 100 million cells/mi is used. In further embodiments, concentrations of 125 or 150 million cells/mi can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In certain embodiments, the population of immune cells (e.g., T cells) is comprised within cells such as peripheral blood mononuclear cells, cord blood cells, a purified population of T cells, and a T cell line. In certain embodiments, peripheral blood mononuclear cells comprise the population of T cells. In yet another embodiment, purified T cells comprise the population of T cells.

In certain embodiments, T regulatory cells (Tregs) can be isolated from a sample. The sample can include, but is not limited to, umbilical cord blood or peripheral blood. In certain embodiments, the Tregs are isolated by flow-cytometry sorting. The sample can be enriched for Tregs prior to isolation by any means known in the art. The isolated Tregs can be cryopreserved, and/or expanded prior to use. Methods for isolating Tregs are described in U.S. Pat. Nos. 7,754,482, 8,722,400, and 9,555,105, and U.S. patent application Ser. No. 13/639,927, contents of which are incorporated herein in their entirety.

J. Pharmaceutical Compositions and Formulations

Also provided are compositions including the cells for administration, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In certain embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In certain embodiments, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In certain embodiments, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

Buffering agents in certain embodiments are included in the compositions. Suitable buffering agents include, for example, citric acid, sodium citrate, phosphoric acid, potassium phosphate, and various other acids and salts. In certain embodiments, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, e.g., those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

Formulations include those for oral, intravenous, intraperitoneal, subcutaneous, pulmonary, transdermal, intramuscular, intranasal, buccal, sublingual, or suppository administration. In certain embodiments, the cell populations are administered parenterally. The term "parenteral," as used herein, includes intravenous, intramuscular, subcutaneous, rectal, vaginal, and intraperitoneal administration. In certain embodiments, the cells are administered to the subject using peripheral systemic delivery by intravenous, intraperitoneal, or subcutaneous injection. Compositions in certain embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present disclosure has been described with reference to the specific embodiments thereof, it should be understood by those skilled in the art that various changes may be made and equivalents may be substituted without departing from the true spirit and scope of the disclosure. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present disclosure. All such modifications are intended to be within the scope of the claims appended hereto. Having now described certain embodiments in detail, the same will be more clearly understood by reference to the following examples, which are included for purposes of illustration only and are not intended to be limiting.

K. Additional Embodiments

The present disclosure is also described by the following embodiments.

Embodiment 1. A method for activating, stimulating and and/or expanding a population of immune cells, comprising: obtaining a population of cells comprising immune cells; contacting the population of cells with a modified cell of leukemic origin, wherein the modified cell comprises a mature dendritic cell phenotype and is non-proliferating; and culturing the population of cells under conditions suitable to stimulate proliferation of the immune cells, thereby activating and expanding the population of immune cells.

Embodiment 2. A method for generating a population of memory T cells, comprising: obtaining a population of cells comprising immune cells; contacting the population of cells with a modified cell of leukemic origin, wherein the modified cell comprises a mature dendritic cell phenotype and is non-proliferating; and culturing the population of cells under conditions suitable to stimulate proliferation of the immune cells, thereby generating the population of memory T cells.

Embodiment 3. A method for enhanced the activation status of a population of autologous T cells, comprising: obtaining a population of autologous T cells from a patient suffering from cancer; modifying the population of autologous T cells to express an engineered immune receptor selected from a chimeric antigen receptor (CAR) or a T cell receptor (TCR) which binds a tumor antigen in the patient; contacting the population of modified autologous T cells with a modified cell of leukemic origin, wherein the modified cell comprises a mature dendritic cell phenotype and is non-proliferating; and co-culturing the population of modified immune cells and modified cells of leukemic origin under conditions suitable to stimulate proliferation of the immune cells, thereby generating the population of autologous cells with enhanced activation status.

Embodiment 4. A method for expanding the anti-tumor specificity of population of autologous T cells, comprising: obtaining a population of autologous T cells from a patient suffering from cancer; modifying the population of autologous T cells to express an engineered immune receptor selected from a chimeric antigen receptor (CAR) or a T cell receptor (TCR) which binds a tumor antigen on a tumor cell in the patient; contacting the population of modified autologous T cells with a modified cell of leukemic origin, wherein the modified cell comprises a mature dendritic cell phenotype and is non-proliferating; and co-culturing the population of modified immune cells and modified cells of leukemic origin under conditions suitable to expand the anti-tumor antigen specificity of the modified immune cells, thereby generating the population of autologous cells capable of reacting with tumor cells of the patient that do not express the tumor antigen to which the engineered receptor binds.

Embodiment 5. The methods of any of the previous Embodiments, further comprising administering the population of autologous cells with enhanced activation status to the patient suffering from cancer.

Embodiment 6. The method of any preceding Embodiment, wherein the modified cell comprises at least one tumor antigen selected from the group consisting of WT-1, RHAMM, PRAME, MUC-1, p53, and Survivin.

Embodiment 7. The method of any preceding, wherein the immune cells are activated following exposure to the endogenous cells expressed by the modified cell of leukemic origin.

Embodiment 8. The method of any one of the preceding Embodiments, wherein the modified cell is CD34-positive, CD1a-positive, and CD83-positive.

Embodiment 9. The method of any one of the preceding Embodiments, wherein the modified cell comprises a cell surface marker selected from the group consisting of CD14, DC-SIGN, Langerin, CD40, CD70, CD80, CD83, CD86, and any combination thereof.

Embodiment 10. The method of any one of the preceding Embodiments, wherein the modified cell comprises a costimulatory molecule.

Embodiment 11. The method of Embodiment 10, wherein the costimulatory molecule is CD70.

Embodiment 12. The method of any one of the preceding Embodiments, wherein the modified cell comprises an MHC class I molecule.

Embodiment 13. The method of any one of the preceding Embodiments, wherein the modified cell comprises an MHC class II molecule.

Embodiment 14. The method of any one of the preceding Embodiments, wherein the modified cell is loaded with an exogenous antigen or peptide fragments thereof.

Embodiment 15. The method of any one of the preceding Embodiments, wherein the exogenous antigen is a tumor-associated antigen (TAA) or non-tumor-associated antigen.

Embodiment 16. The method of any one of the preceding Embodiments, wherein the modified cell is capable of expressing the exogenous antigen.

Embodiment 17. The method of any one of the preceding Embodiments, wherein the modified cell is not capable of expressing the exogenous antigen.

Embodiment 18. The method of any one of the preceding Embodiments, wherein the exogenous antigen is provided in the form of a peptide, a nucleotide sequence, whole protein, or tumor lysate.

Embodiment 19. The method of any one of the preceding Embodiments, wherein the exogenous antigen is matched with the antigen to which the engineered immune receptor binds.

Embodiment 20. The method of any one of the preceding Embodiments, wherein the exogenous antigen is different from the antigen to which the engineered immune receptor binds.

Embodiment 21. The method of any one of the preceding Embodiments, wherein the modified cell of leukemic origin is loaded with the exogenous antigen or peptide fragments thereof prior to its exhibiting a mature dendritic cell phenotype.

Embodiment 22. The method of any one of the preceding Embodiments, wherein the modified cell of leukemic origin is loaded with the exogenous antigen or peptide fragments thereof during transition of the modified cell of leukemic origin to a mature dendritic cell phenotype.

Embodiment 23. The method of any one of the preceding Embodiments, wherein the modified cell of leukemic origin is loaded with the exogenous antigen or peptide fragments thereof prior to, after the modified cell of leukemic origin exhibits a mature dendritic cell phenotype.

Embodiment 24. The method of any one of the preceding Embodiments, wherein the modified cell comprises a genetic aberration between chromosome 11p15.5 to 11p12.

Embodiment 25. The method of Embodiment 24, wherein the genetic aberration encompasses about 16 Mb of genomic regions.

Embodiment 26. The method of any one of the preceding Embodiments, wherein the modified cell has been irradiated.

Embodiment 27. The method of any one of the preceding Embodiments, wherein the conditions suitable to stimulate proliferation of the immune cells comprises providing signal-1 to the immune cells.

Embodiment 28. The method of Embodiment 27, wherein signal-1 is provided by the modified cell.

Embodiment 29. The method of Embodiment 27 or 28, wherein signal-1 comprises activation of a TCR/CD3 complex.

Embodiment 30. The method of any one of the preceding Embodiments, wherein the conditions suitable to stimulate proliferation of the immune cells comprises providing signal-2 to the immune cells.

Embodiment 31. The method of Embodiment 30, wherein signal-2 is provided by the modified cell.

Embodiment 32. The method of Embodiment 29 or 30, wherein signal-2 comprises activation of a costimulatory molecule.

Embodiment 33. The method of Embodiment 32, wherein the costimulatory molecule is CD70.

Embodiment 34. The method of any one of the preceding Embodiments, wherein the population of cells is derived from a human.

Embodiment 35. The method of any one of the preceding Embodiments, wherein the population of cells comprise T cells.

Embodiment 36. The method of any one of the preceding Embodiments, wherein the T cells comprise both CD4+ and CD8+ cells, and wherein the method results in combined stimulation of both the CD4+ and CD8+ cells.

Embodiment 37. The method of any one of the preceding Embodiments, wherein the T cells comprise both CD4+ and CD8+ cells, and wherein the method results in an increased ratio of CD4+ to CD8+ cells.

Embodiment 38. The method of any one of the preceding Embodiments, wherein the population of cells comprise non-stimulated T cells.

Embodiment 39. The method of any one of the previous Embodiments, wherein the modified immune cell is an autologous cell derived from a patient suffering from cancer.

Embodiment 40. The method of any one of the previous Embodiments, wherein the modified immune cells comprise a functional endogenous TCR repertoire.

Embodiment 41. The method of any one of the previous Embodiments, wherein immune cell is engineered to target the exogenous antigen of the modified immune cell of leukemic origin.

Embodiment 42. The method of any one of the previous Embodiments, wherein the immune cells in engineered to target the same tumor-associated antigen (TAA) of the modified cell of leukemic origin.

Embodiment 43. The method of any one of the previous Embodiments, wherein the immune cells are cross-reactive with non-tumor derived antigens displayed by the modified immune cell of leukemic origin.

Embodiment 44. The method of any one of the previous Embodiments, wherein the non-tumor derived antigens are viral or vaccine-derived recall antigens.

Embodiment 45. The method of any one of the previous Embodiments, wherein the engineered immune cells are Epstein Barr Virus (EBV)-specific T cells.

Embodiment 46. The method of any one of the preceding Embodiments, wherein the immune cells comprise an immune receptor.

Embodiment 47. The method of Embodiment 46, wherein the immune receptor is a chimeric antigen receptor (CAR) or a T cell receptor (TCR).

Embodiment 48. The method of Embodiment 47, wherein the CAR comprises an antigen binding domain, a transmembrane domain, and an intracellular domain comprising a costimulatory domain and a primary signaling domain.

Embodiment 49. The method of Embodiment 48, wherein the antigen binding domain comprises a full-length antibody or antigen-binding fragment thereof, a Fab, a single-chain variable fragment (scFv), or a single-domain antibody.

Embodiment 50. The method of Embodiment 48 or 49, wherein the antigen binding domain is specific for a tumor-associated antigen (TAA) or a non-tumor-associated antigen.

Embodiment 51. The method of Embodiment 50, wherein the antigen binding domain is specific for a tumor-associated antigen (TAA) or non-tumor-associated antigen that is distinct from the exogenous antigen.

Embodiment 52. The method of Embodiment 50, wherein the antigen binding domain is specific for a tumor-associated antigen (TAA) or non-tumor-associated antigen that is the same as the exogenous antigen.

Embodiment 53. The method of any one of Embodiments 48-52, wherein the CAR further comprises a hinge region.

Embodiment 54. The method of Embodiment 53, wherein the hinge region is a hinge domain selected from the group consisting of an Fc fragment of an antibody, a hinge region of an antibody, a CH2 region of an antibody, a CH3 region of an antibody, an artificial hinge domain, a hinge comprising an amino acid sequence of CD8, or any combination thereof.

Embodiment 55. The method of any one of Embodiments 48-54, wherein the transmembrane domain is selected from the group consisting of an artificial hydrophobic sequence, a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), ICOS (CD278), or CD154, and a transmembrane domain derived from a killer immunoglobulin-like receptor (KIR).

Embodiment 56. The method of any one of Embodiments 48-55, wherein the intracellular domain comprises a costimulatory signaling domain and an intracellular signaling domain.

Embodiment 57. The method of Embodiment 56, wherein the costimulatory signaling domain comprises one or more of a costimulatory domain of a protein selected from the group consisting of proteins in the TNFR superfamily, CD27, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS (CD278), NKG2C, B7-H3 (CD276), and an intracellular domain derived from a killer immunoglobulin-like receptor (KIR), or a variant thereof.

Embodiment 58. The method of Embodiment 56 or 57, wherein the intracellular signaling domain comprises an intracellular domain selected from the group consisting of cytoplasmic signaling domains of a human CD3 zeta chain (CD3), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof.

Embodiment 59. The method of Embodiment 47, wherein the TCR is endogenous to the immune cells.

Embodiment 60. The method of Embodiment 47, wherein the TCR is exogenous to the immune cells.

Embodiment 61. The method of Embodiment 47, wherein the TCR comprises a TCR alpha chain and a TCR beta chain.

Embodiment 62. The method of Embodiment 47, wherein the TCR is selected from the group consisting of a wildtype TCR, a high affinity TCR, and a chimeric TCR.

Embodiment 63. The method of Embodiment 47, wherein the TCR is selected from the group consisting of a full-length TCR, a dimeric TCR, and a single-chain TCR.

Embodiment 64. The method of any one of Embodiment 47 or 59-63, wherein the TCR is specific for a tumor-associated antigen (TAA) or non-tumor-associated antigen that is distinct from the exogenous antigen.

Embodiment 65. The method of any one of Embodiment 47 or 59-63, wherein the TCR is specific for a tumor-associated antigen (TAA) or non-tumor-associated antigen that is the same as the exogenous antigen.

Embodiment 66. A method for generating an antigen-specific immune cell, comprising inducing generation of the antigen-specific immune cell by contacting an immune cell with a modified cell of leukemic origin, wherein the modified cell comprises a mature dendritic cell phenotype and is non-proliferating.

Embodiment 67. The method of Embodiment 66, wherein the modified cell comprises a target antigen.

Embodiment 68. The method of Embodiment 67, wherein the target antigen is endogenous to the modified cell and selected from the group consisting of WT-1, RHAMM, PRAME, MUC-1, p53, Survivin, and any combination thereof.

Embodiment 69. The method of any one of Embodiments 66-68, wherein the target antigen is exogenous to the modified cell.

Embodiment 70. The method of any one of Embodiments 66-69, wherein the target antigen is a tumor-associated antigen (TAA) or a non-tumor-associated antigen.

Embodiment 71. The method of any one of Embodiments 66-70, wherein the modified cell is CD34-positive, CD1a-positive, and CD83-positive.

Embodiment 72. The method of any one of Embodiments 66-671, wherein the modified cell comprises a cell surface marker selected from the group consisting of CD14, DC-SIGN, Langerin, CD40, CD70, CD80, CD83, CD86, and any combination thereof.

Embodiment 73. The method of any one of Embodiments 66-62, wherein the modified cell comprises a costimulatory molecule.

Embodiment 74. The method of Embodiment 73, wherein the costimulatory molecule is CD70.

Embodiment 75. The method of any one of Embodiments 66-74, wherein the modified cell comprises an MHC class I molecule.

Embodiment 76. The method of any one of Embodiments 66-75, wherein the modified cell comprises an MHC class II molecule.

Embodiment 77. The method of any one of Embodiments 66-76, wherein the modified cell comprises a genetic aberration between chromosome 11p15.5 to 11p12.

Embodiment 78. The method of Embodiment 77, wherein the genetic aberration encompasses about 16 Mb of genomic regions.

Embodiment 79. The method of any one of Embodiments 66-78, wherein the modified cell has been irradiated.

Embodiment 80. A method for expanding a population of modified immune cells, comprising: obtaining a population of modified immune cells, wherein the modified immune cells comprise an immune receptor; contacting the population of cells with a modified cell of leukemic origin, wherein the modified cell comprises a mature dendritic cell phenotype and is non-proliferating; and culturing the population of modified immune cells under conditions suitable to stimulate proliferation of the modified immune cells, thereby expanding the population of modified immune cells.

Embodiment 81. The method of Embodiment 80, wherein the modified cell comprises a target antigen.

Embodiment 82. The method of Embodiment 81, wherein the target antigen is endogenous to the modified cell and selected from the group consisting of WT-1, RHAMM, PRAME, MUC-1, p53, Survivin, and any combination thereof.

Embodiment 83. The method of Embodiment 80, wherein the target antigen is exogenous to the modified cell.

Embodiment 84. The method of Embodiment 80, wherein the target antigen is a tumor-associated antigen (TAA) or a non-tumor-associated antigen.

Embodiment 85. The method of any one of Embodiments 80-84, wherein the modified cell is CD34-positive, CD1a-positive, and CD83-positive.

Embodiment 86. The method of any one of Embodiments 80-85, wherein the modified cell comprises a cell surface marker selected from the group consisting of CD14, DC-SIGN, Langerin, CD40, CD70, CD80, CD83, CD86, and any combination thereof.

Embodiment 87. The method of any one of Embodiments 80-86, wherein the modified cell comprises a costimulatory molecule.

Embodiment 88. The method of Embodiment 87, wherein the costimulatory molecule is CD70.

Embodiment 89. The method of any one of Embodiments 80-88, wherein the modified cell comprises an MHC class I molecule.

Embodiment 90. The method of any one of Embodiments 80-88, wherein the modified cell comprises an MHC class II molecule.

Embodiment 91. The method of any one of Embodiments 80-90, wherein the modified cell comprises a genetic aberration between chromosome 11p15.5 to 11p12.

Embodiment 92. The method of Embodiment 91, wherein the genetic aberration encompasses about 16 Mb of genomic regions.

Embodiment 93. The method of any one of Embodiments 80-92, wherein the modified cell has been irradiated.

Embodiment 94. The method of any one of Embodiments 80-93, wherein the conditions suitable to stimulate proliferation of the immune cells comprises providing signal-1 to the immune cells.

Embodiment 95. The method of Embodiment 94, wherein signal-1 is provided by the modified cell.

Embodiment 96. The method of Embodiment 94 or 95, wherein signal-1 comprises activation of a TCR/CD3 complex.

Embodiment 97. The method of any one of Embodiments 80-97, wherein the conditions suitable to stimulate proliferation of the immune cells comprises providing signal-2 to the immune cells.

Embodiment 98. The method of Embodiment 97, wherein signal-2 is provided by the modified cell.

Embodiment 99. The method of Embodiment 98, wherein signal-2 comprises activation of a costimulatory molecule.

Embodiment 100. The method of Embodiment 99, wherein the costimulatory molecule is CD70.

Embodiment 101. A method for treating a disease or disorder in a subject in need thereof, comprising: administering to the subject a modified immune cell produced by any one of the methods of the preceding Embodiments.

Embodiment 102. The method of Embodiment 101, wherein the disease or disorder is a cancer.

Embodiment 103. The method of Embodiment 102, wherein the cancer is a tumor.

Embodiment 104. The method of Embodiment 103, wherein the tumor is a liquid tumor.

Embodiment 105. The method of Embodiment 103, wherein the tumor is a solid tumor.

Embodiment 106. The method of Embodiment 101, wherein the modified cell is an autologous cell derived from the patient suffering from the cancer.

L. Experimental Examples

The following examples are put forth so as to provide those of ordinary skill in the art with a complete disclosure and description of how to make and use the methods and compositions featured in the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Figure 2:
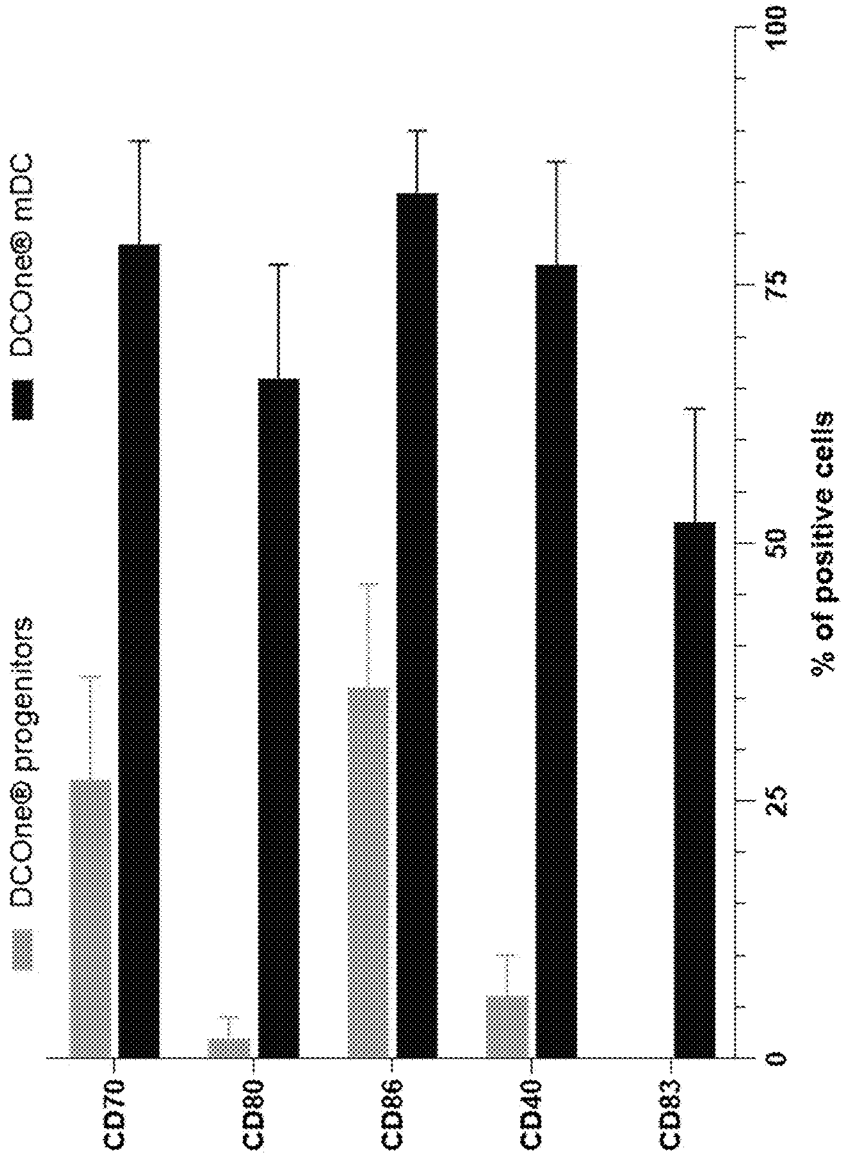
FIG. 2 depicts a plot showing the expression profile of DCOne progenitors and DCOne cells with a mature dendritic cell phenotype (mDCs).

Example 1: DCOne Cells could be Shifted Towards a Mature Dc Phenotype (mDC) and Used as Potent Stimulators of T Cell Proliferation FIG. 2 shows a shift in expression profile upon differentiation of DCOne progenitor cells into cells having a mature dendritic cell (mDC) phenotype. As shown in FIG. 2, upon differentiation into mDCs, the number of mDCs that were CD70+, CD80+, CD86+, CD40+, or CD83+ was significantly higher as compared to DCOne progenitor cells assayed for the same expression profile.

Figure 3:
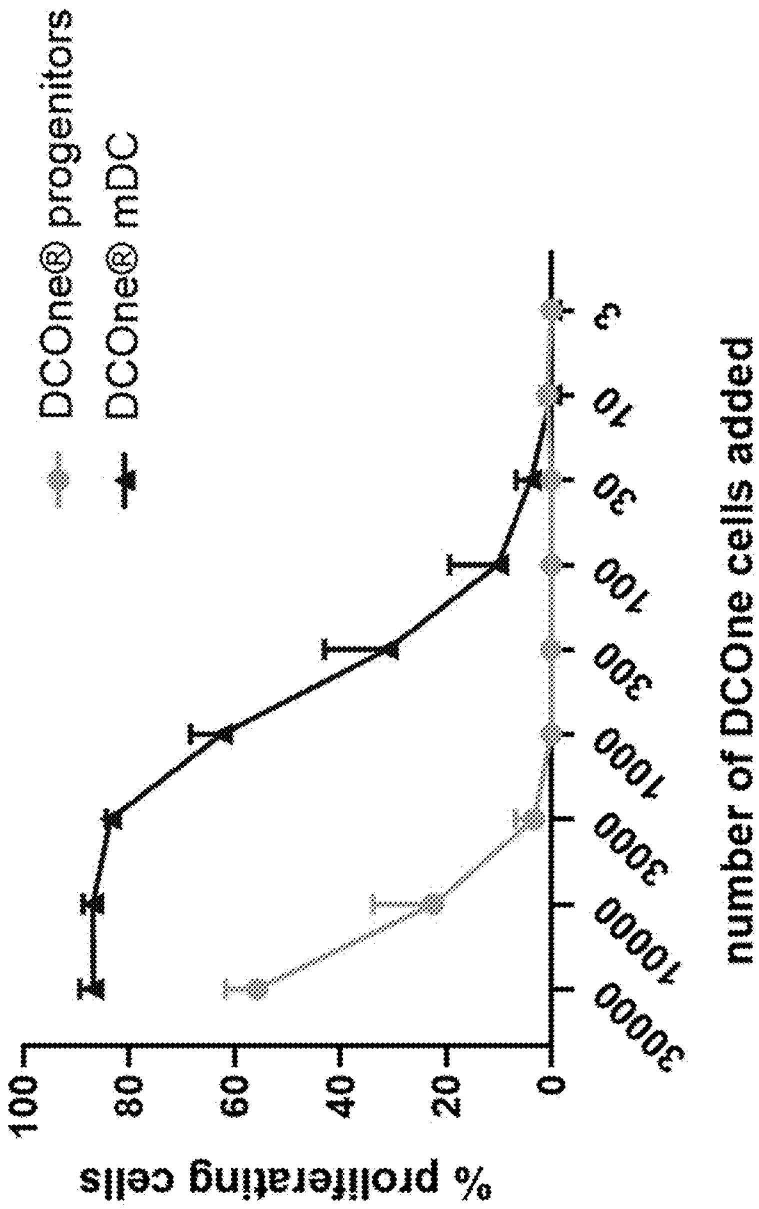
FIG. 3 depicts a graph showing the percentage of proliferating cells resulting from the addition of DCOne progenitors or DCOne mDCs.
Figures 4A, 4B, 4C, 4D, 4E, 4F, 4G:
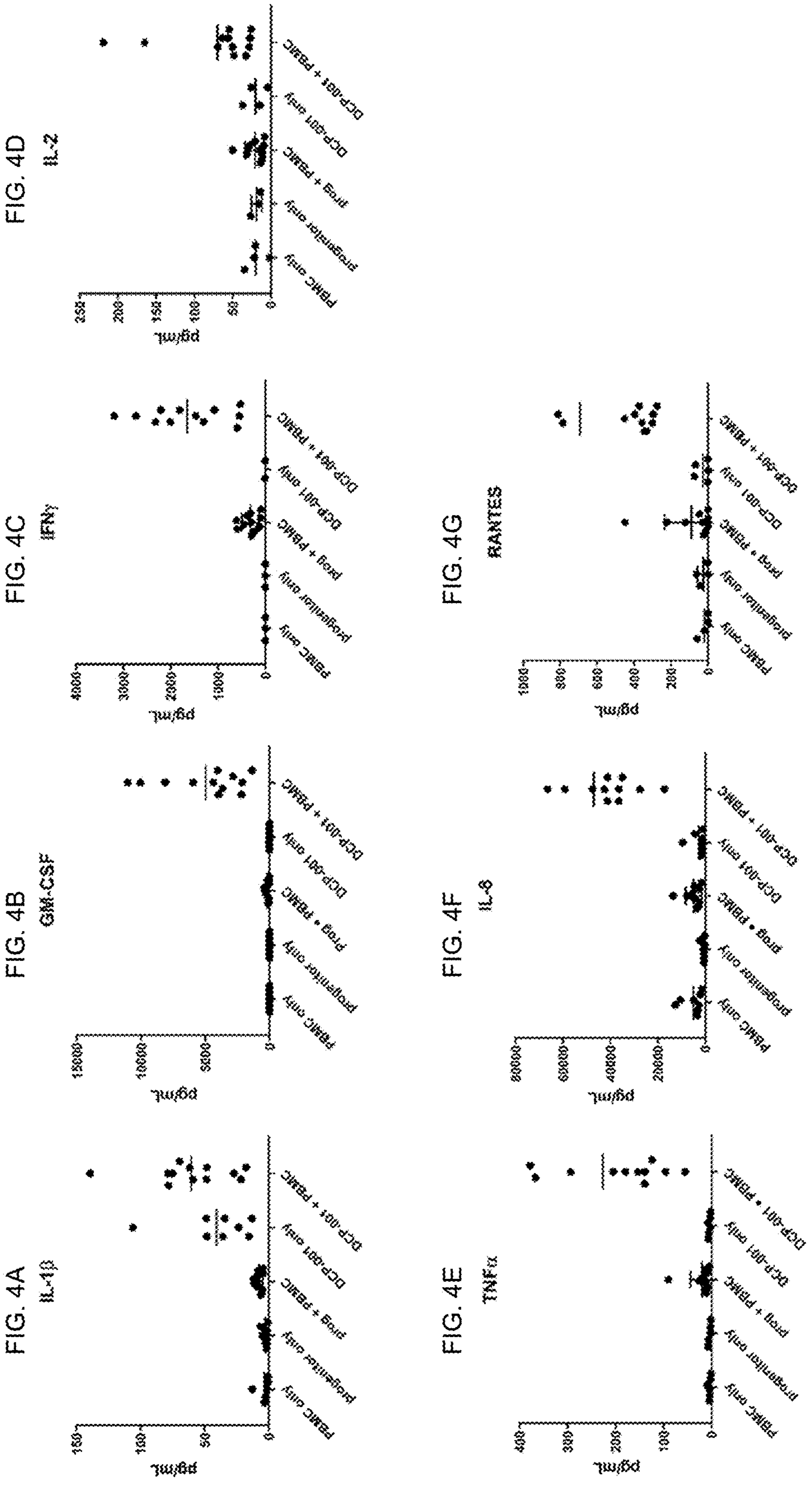
FIGS. 4A-4G depict plots demonstrating the release of inflammatory and effector cytokines in PBMCs stimulated with DCP-001. In particular, the plots depict the release of IL-1β (FIG. 4A), GM-CSF (FIG. 4B), IFNγ (FIG. 4C), IL-2 (FIG. 4D), TNFα (FIG. 4E), IL-8 (FIG. 4F), and RANTES (FIG. 4G).

Irradiated DCOne derived mDCs (DCP001) were found to be potent stimulators of T cell proliferation (FIG. 3). As shown in FIG. 3, mDCs significantly enhanced the number of proliferating cells in a dose-dependent manner, as compared to the capability of DCOne progenitors. Further, DCP001 cells were found to trigger release of inflammatory and effector cytokines in PBMCs (FIGS. 4A-4G). DCP-001 ("DCP-001+PBMC") had a strong immunostimulatory effect on PBMCs whereas DCOne® progenitor cells ("prog+PBMC") lack this immunostimulatory capacity. Furthermore, DCP-001 was found to produce IL-1β (FIG. 4A), an immunostimulatory cytokine involved in DC activation. DCP-001 was found to trigger release of GM-CSF (FIG. 4B), IFNγ (FIG. 4C), IL-2 (FIG. 4D), TNFα (FIG. 4E), IL-8 (FIG. 4F), and RANTES (FIG. 4G).

Figure 5A:
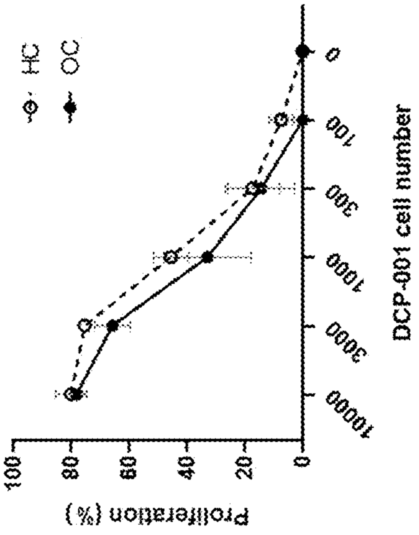
FIGS. 5A-5C depict plots demonstrating that DCP-001 stimulated T cell proliferation of CD3 T cells (FIG. 5A), CD4+ T cells (FIG. 5B) and CD8+ T cells (FIG. 5C) in healthy donor and ovarian cancer patients PBMC.
Figure 5B:
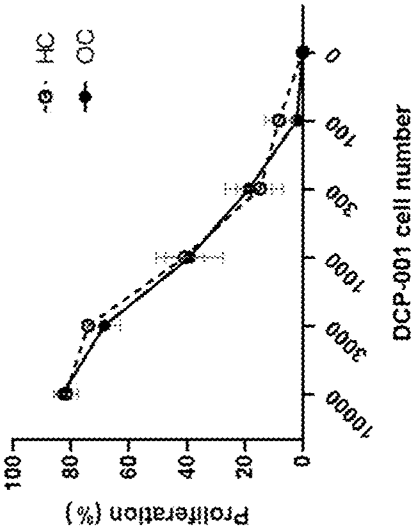
Figure 5C:
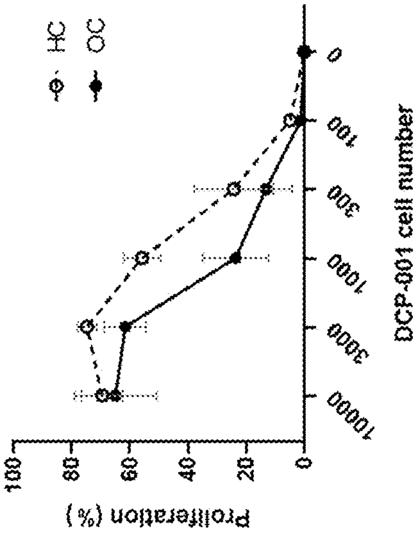

Finally, PBMC from healthy donors and ovarian cancer patients were co-cultured with increasing amounts of DCP-001. T cell proliferation was analysed using a 6-day MLR assay. FIGS. 5A-5C shows plots demonstrating that DCP-001 stimulates T cell proliferation in healthy donor and ovarian cancer patient PBMCs. CD3 T cells (FIG. 5A), CD4+ T cells (FIG. 5B) and CD8+ T cells (FIG. 5C) all proliferated in response to DCP-001. Data depicted represent the mean±SD. HC represents data collected from PBMCs of healthy controls (healthy donors), and OC represents data collected from PBMCs of ovarian cancer patients.

Figure 6B:
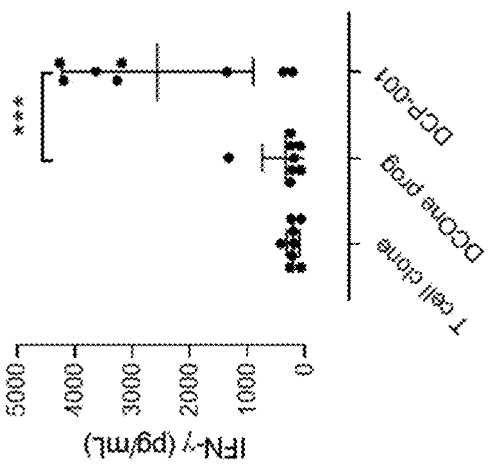
FIGS. 6A-6D depict plots demonstrating the response of antigen specific T cell clones against antigens expressed by DCOne mDCs (DCP-001).
Figure 6D:
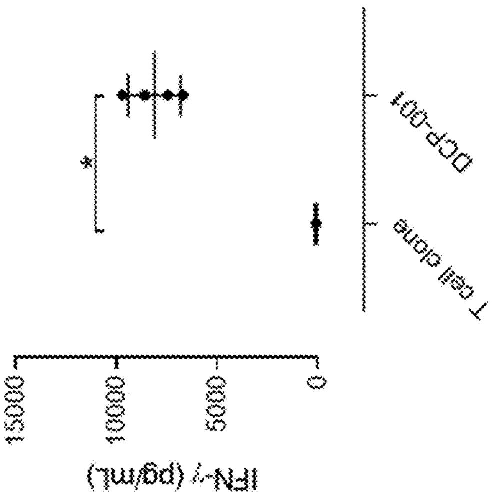
Figure 6A:
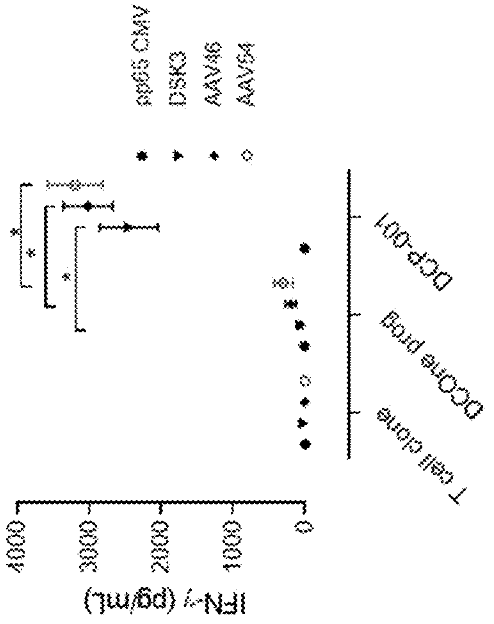
Figure 6C:
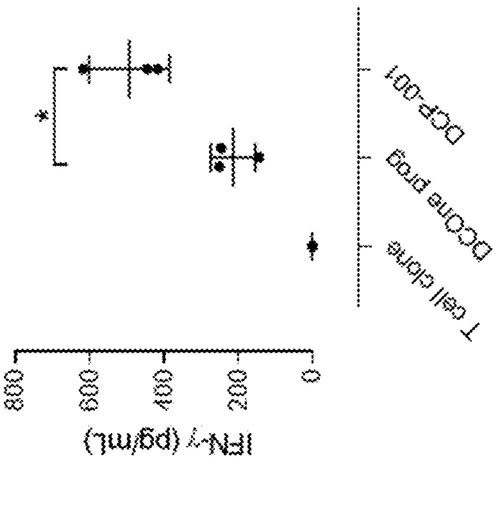

Example 2: DCP-001 (DCOne Derived mDCs) could Stimulate T Cells Directed Against Both Endogenous and Exogenous Antigens Ex Vivo DCOne mDCs were found to stimulate antigen-specific T cell clones directed against endogenous antigens expressed by the DCOne cell line (FIGS. 6A-6D). FIG. 6A shows the response of PRAME T cell clones to DCP-001. As shown in FIG. 6A, DCP-001 was found to stimulate DSK3, AAV46, and AAV54 PRAME T cell clones, but not a control T cell clone that recognizes a pp65 CMV antigen. FIG. 6B shows the response of WT-1 T cell clones to DCP-001; FIG. 6C shows the response of MUC-1 T cell clones to DCP-001, and FIG. 6D shows the response of RHAMM T cell clones to DCP-001.

In FIG. 6A, irradiated DCOne progenitors or DCP-001 were incubated with three PRAME-specific T cell clones and one CMV pp65-specific T cell clone, at a stimulator: responder ratio of 5:1 in round-bottom 96-wells culture plates for 18 hours. IFNγ production was analyzed in culture supernatants employing ELISA. T cell clones only, without DCOne-derived cells, served as negative control. Data shown were from 3 different DCOne-derived cell batches, each performed in duplicate. IFNγ levels (pg/mL) are presented as mean±SD. One-way ANOVA multiple comparison was used to calculate p-values. *=p<0.05

In FIG. 6B, irradiated DCOne progenitor or DCP-001 cells were incubated with HLA-A2 restricted CD8+ T cell clone specific for WT[126-134], at a stimulator:responder ratio of 1:5 in round-bottom 96-wells culture plates for 24 hours. IFNγ production was analyzed in culture supernatants employing ELISA. T cell clone only, without DCOne-derived cells, served as negative control. Horizontal lines indicate mean±SD from n=8 experiments. One-way ANOVA multiple comparison was used to calculate p-values. ***=p<0.0005.

In FIG. 6C, irradiated DCOne progenitor or DCP-001 cells were incubated with a HLA-A2 restricted CD8+ T cell clone specific for MUC-1[950-958], at a stimulator:responder ratio of 1:5 in round-bottom 96-wells culture plates for 24 hours. IFNγ production was analyzed in culture supernatants employing ELISA. T cell clone only, without DCP-001, served as negative control. Data shown were from 4 different DCP-001 batches, each performed in triplicates. One-way ANOVA multiple comparison was used to calculate p-values. *=p<0.05

In FIG. 6D, irradiated DCP-001 cells were incubated with HLA-A2 restricted CD8+ T cell clone specific for RHAMM [165-173], at a stimulator:responder ratio of 1:5 in round-bottom 96-wells culture plates for 24 hrs. IFNγ production was analyzed in culture supernatants employing ELISA. T cell clone only, without DCP-001, served as negative control. Data shown were from 3 different DCP-001 batches, each performed in triplicates. One-way ANOVA multiple comparison was used to calculate p-values. *=p<0.05.

Figure 7B:
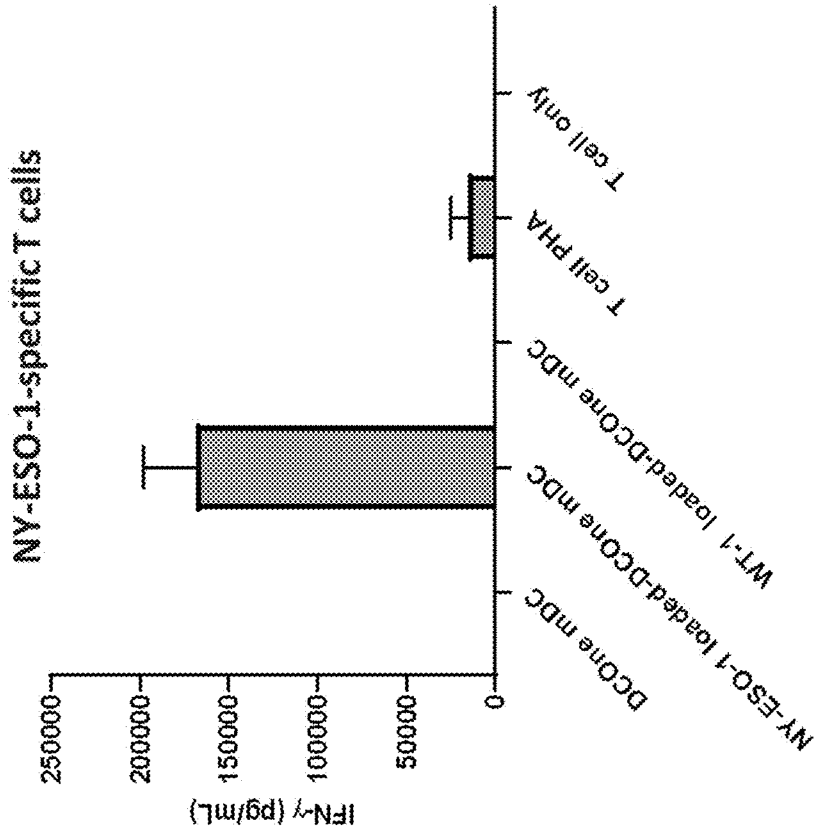
FIGS. 7A-7B depict a graph demonstrating that DCOne mDCs loaded with exogenous antigens were a potent stimulator of antigen-specific T cells in vitro as measured by IFNγ expression.
Figure 7A:
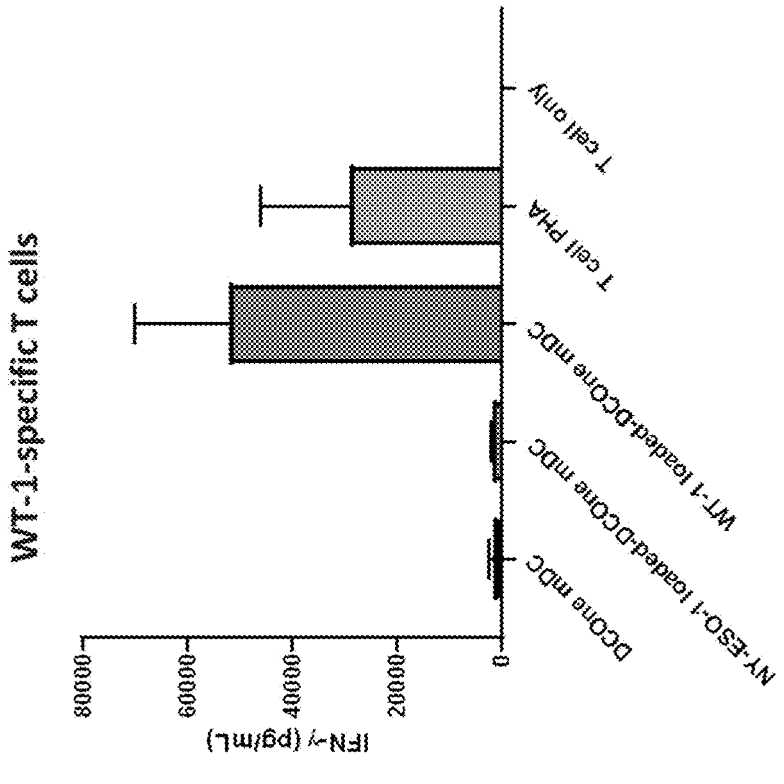

Further, DCOne mDCs were found to stimulate antigen-specific T cell clones directed against exogenous antigens that are not expressed by the DCOne cell line, but are present on tumors targeted by the antigen-specific T cell clones (FIGS. 7A-7B). In particular, DCOne cells did not express the tumor-specific antigens WT-1 or NY-ESO-1. DCOne cells loaded with exogenous WT-1 antigen (FIG. 7A) or NY-ESO-1 peptide (FIG. 7B) were found to be potent and specific stimulators of WT-1-specific (FIG. 7A) or NY-ESO-1-specific (FIG. 7B) T cells derived from ovarian cancer patients.

Figure 8A:
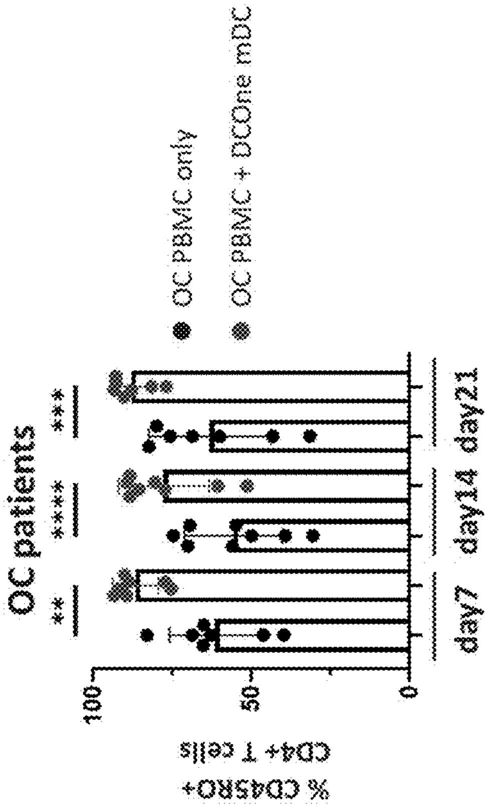
FIGS. 8A-8D depict graphs showing that in vitro stimulation of PBMCs with DCP-001 lead to an increased CD45RO expression in PBMCs from both ovarian cancer patients (OC patients.
Figure 8B:
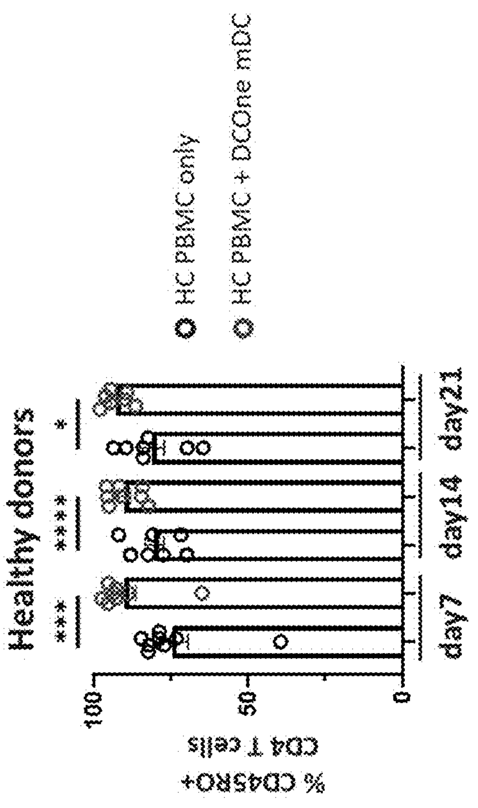
Figure 8C:
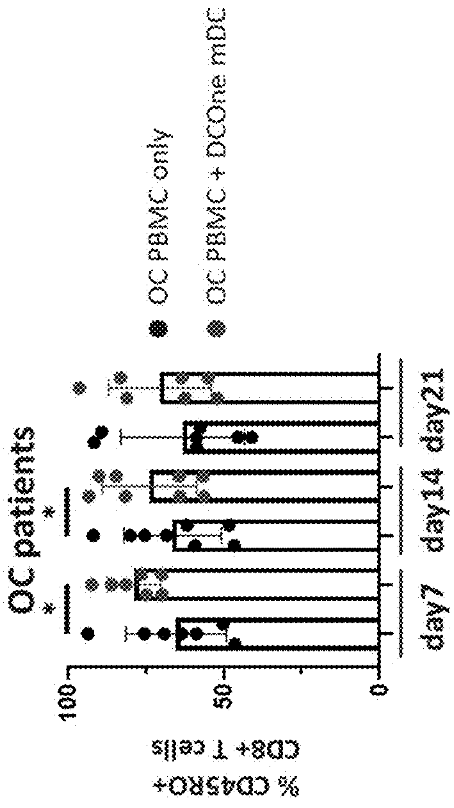
Figure 8D:
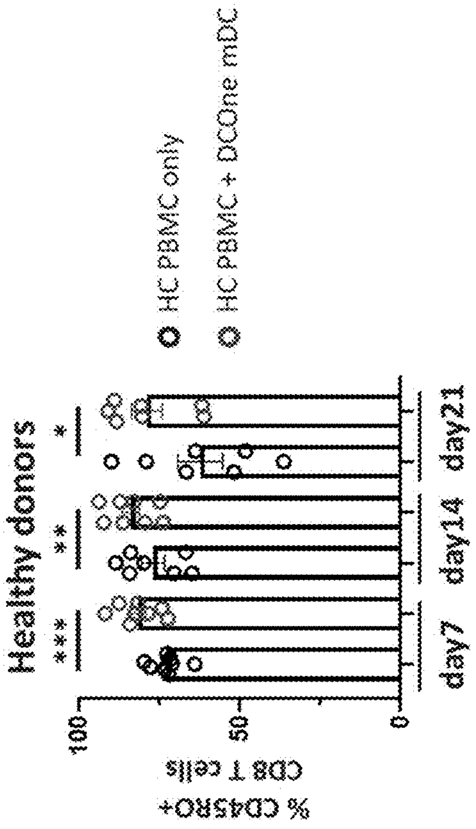

Example 3: DCOne Derived mDCs Stimulated Anti-Tumor Responses to Autologous Cells from Cancer Patients Ex Vivo FIGS. 8A-8D show that in vitro stimulation of PBMC with DCP-001 (DCOne mDC) lead to an increased CD45RO expression, an important marker for T cell activation and memory formation. HC represents healthy controls (healthy donors; FIG. 8B and FIG. 8D), and OC represents ovarian cancer patients (FIG. 8A and FIG. 8C). FIGS. 8A and 8B show the stimulation of CD45RO in CD4+ T cells, in ovarian cancer patients and healthy patients, respectively.

FIGS. 8C and 8D show the stimulation of CD45RO in CD8+ T cells, in ovarian cancer patients and healthy patients, respectively. In FIGS. 8A-8D, * indicates statistical significance as calculated by one-way ANOVA with $p<0.05$; $p<0.005$; *$p<0.001$; and ****$p<0.0001$.

Figure 9A:
FIGS. 9A-9D depict graphs showing that in vitro stimulation of PBMCs with DCP-001 triggered an increased CD4+/CD8+ ratio in PBMCs from both ovarian cancer patients (OC patients.
Figure 9B:
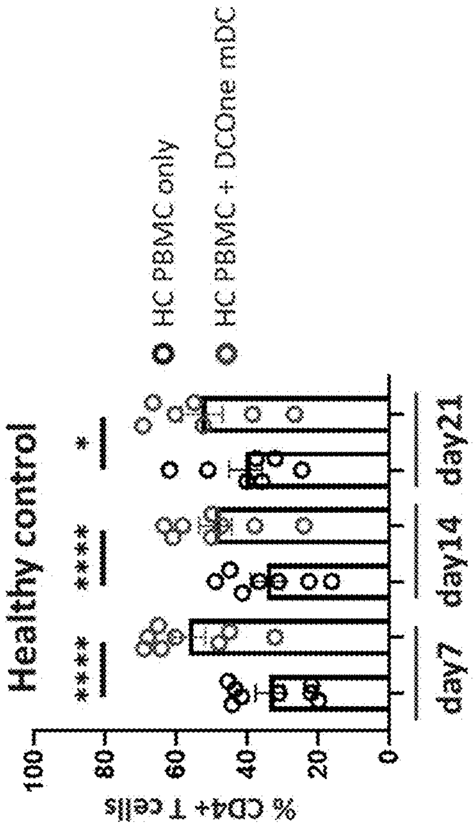
Figure 9C:
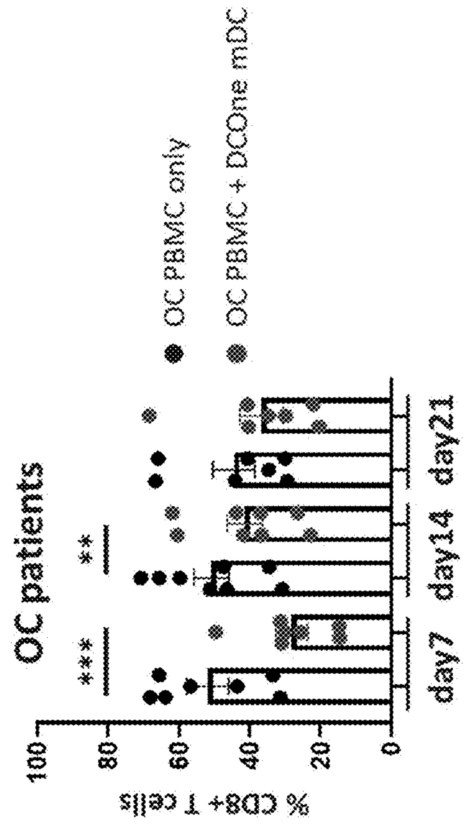
Figure 9D:
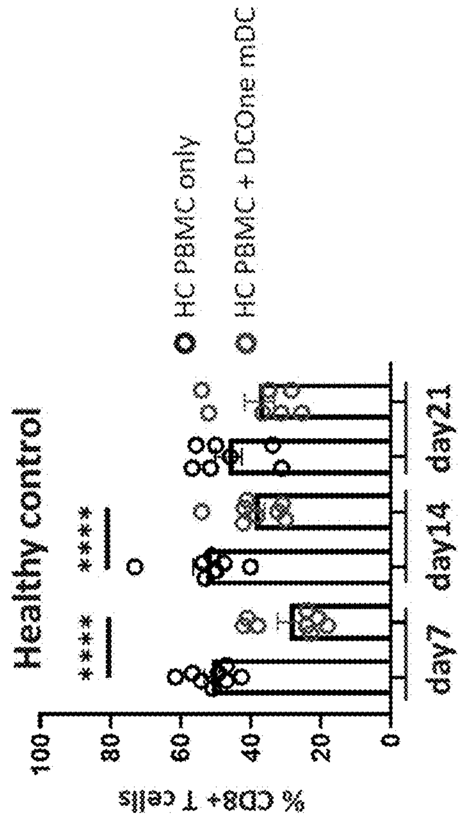

FIGS. 9A-9D show that DCOne triggered CD4+ and CD8+ T cell activation and memory formation in PBMCs from healthy donors and ovarian cancer patients and leads to an increased CD4+/CD8+ ratio. The increased CD4+/CD8+ ratio generally improves the quality of the T cell pool used for CAR-T generation and can improve the efficacy of CAR-T cell therapies in vivo (See e.g. Sommermeyer et al., Leukemia volume 30, 492-500(2016), Garfall et al., Blood Advances Volume 30, number 19 (2019)). HC represents healthy controls (healthy donors; FIGS. 9B and 9D), and OC represents ovarian cancer patients (FIGS. 9A and 9C). FIGS. 9A and 9B show the change in percentage of CD4+ T cells, in ovarian cancer patients and healthy patients, respectively. FIGS. 9C and 9D show the change in percentage of CD8+ T cells, in ovarian cancer patients and healthy patients, respectively. In FIGS. 9A-9D, * indicates statistical significance as calculated by one-way ANOVA with $p<0.05$; $p<0.005$; *$p<0.001$; and ****$p<0.0001$.

Figure 10B:
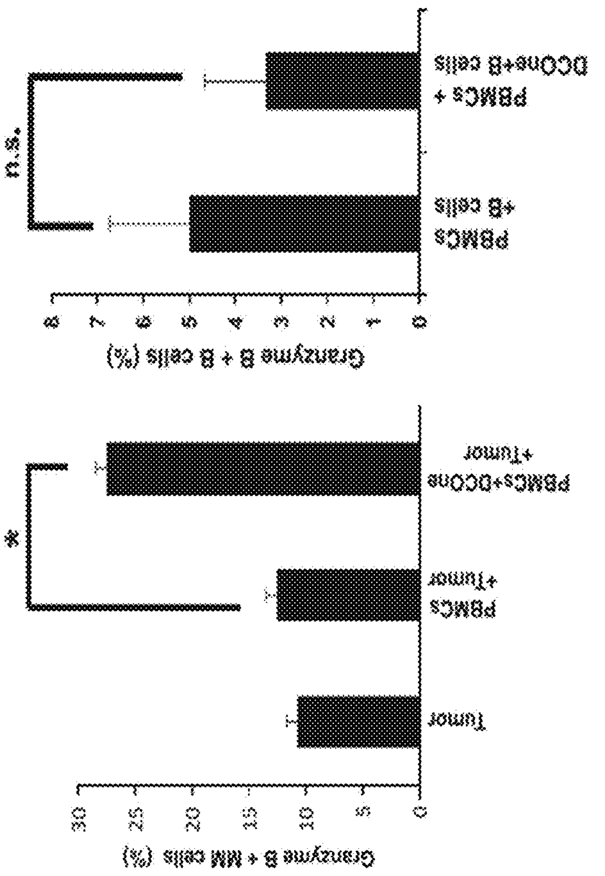
FIGS. 10A-10B depicts a graph showing that DCP001 induced T cell activation and myeloma-specific immunity in PBMCs of multiple myeloma (MM) patients as measured by DCOne RNA uptake (FIG. 10A) and granzyme B killing (FIG. 10B).
Figure 10A:
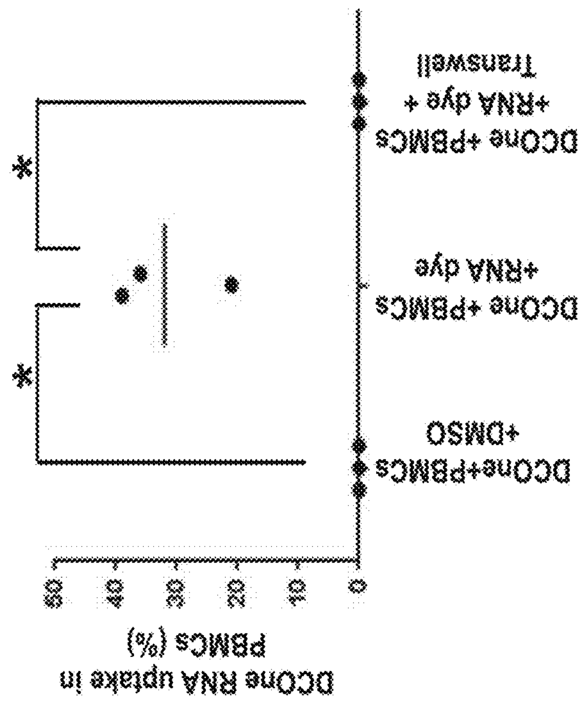

FIGS. 10A-10B show that DCP-001 induced T cell activation and myeloma specific immunity in PBMCs of multiple myeloma (MM) patients. FIG. 10A shows that DCP-001 ingested RNA dye was taken up by PBMCs of MM patients. FIG. 10B shows that DCP-001 activated PBMCs from MM patients could kill autologous MM tumor cells, as indicated by detection of Granzyme B activity, but not healthy B cells (FIG. 10B). In FIG. 10A and FIG. 10B, * indicates statistical significance as calculated by paired-t-test with $p<0.05$.

Figure 11:
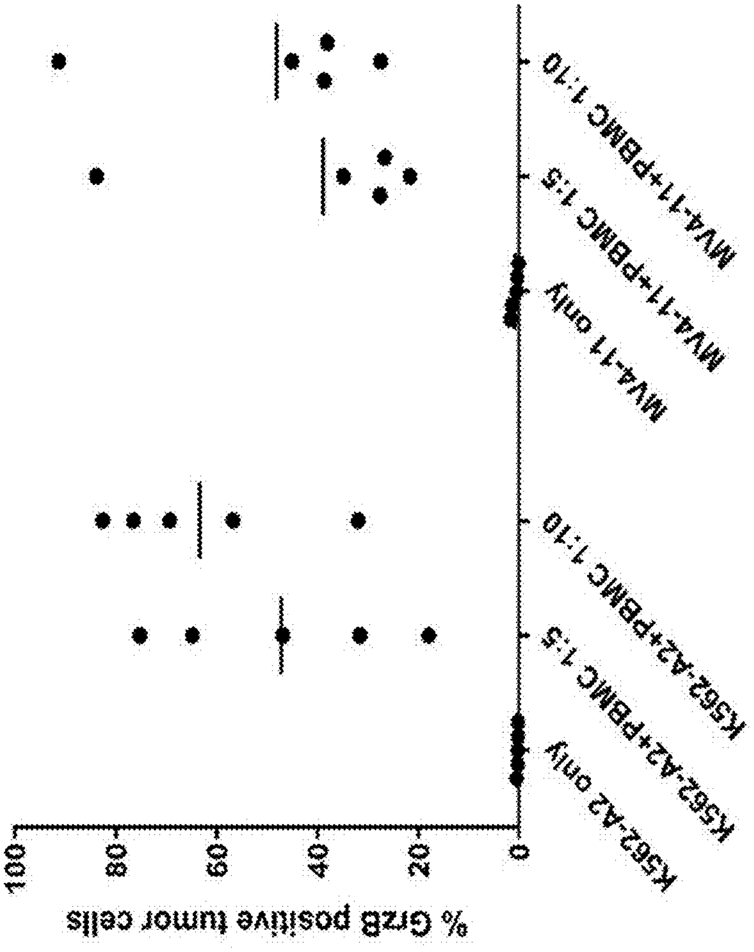
FIG. 11 depicts a graph showing that in vitro stimulation of PBMC with DC One induced cytotoxic T cells responses towards a variety of leukemic cancer cell lines.

FIG. 11 depicts a graph showing that in vitro stimulation of PBMC with DCP-001 induces T cell responses against a variety of leukemic cancer cell lines. The cytotoxic capacity of DCP-001-activated PBMC was determined in co-cultures with tumor target cells K562-A2 (chronic myeloid leukemic tumor cell line) and MV4-11 (acute myeloid leukemic tumor cell line) using the GranToxiLux cell-based fluorogenic cytotoxicity assay, that detect Granzyme B activity. PBMCs were co-cultured with DCOne mDC cells for 6 days and tumor cell cytotoxicity was measured by incubation of the DCOne mDC-stimulated PBMCs (effector cells) for 1 hour with tumor cells (target cells) at a Target:Effector ratio of 1:5 and 1:10. Data from 5 independent experiments are shown; each dot represents the mean of results obtained using PBMC from one individual donor.

Figure 12:
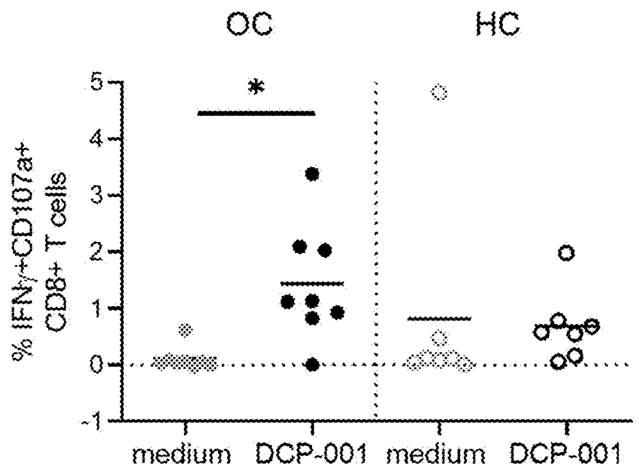
FIG. 12 depicts a graph showing that DCOne mDCs induced cytotoxic T cell responses towards the SKOV ovarian cancer cell line from ovarian cancer patients.

FIG. 12 depicts a graph showing that DCOne mDCs induced cytotoxic T cell responses in PBMCs from ovarian cancer patient towards the SKOV3 ovarian cancer cell line. The cytotoxic capacity of DCP-001-activated PBMC was determined in co-cultures with ovarian cancer target cells SKOV3. PBMCs from ovarian cancer patients (OC; n=8) or heathy controls (HC; n=7) were co-cultured with medium or DCP-001 for 21 days and tumour cell cytotoxicity was measured by incubation of the medium- or DCP-001-stimulated PBMCs (effector cells) for 5 to 6 hours with tumour cells (target cells) at a Target:Effector ratio of 1:10 in the presence of anti-CD107a antibody (marker for cytotoxicity). Cells were then stained for T cell surface markers followed by an intracellular IFNg staining, and measured by flow cytometry. Data from 5 independent experiments are shown; each dot represents the mean of results obtained using PBMC from one individual donor. HC represents healthy controls (healthy donors), and OC represents ovarian cancer patients.

The above examples demonstrate that the induction of T cell responses directed against multiple endogenous antigens and reactive towards different tumor types, as measured by exposing DCOne-stimulated PBMCs to tumor cell lines of different origin, leads to additional anti-tumor activity of the therapy. These findings support reduced risk of antigen escape and increased CAR-T survival/persistence as a result of the broader and continued immunogenic stimulation of the DCOne cells.

These results were especially pronounced in autologous CAR-T cells in which the endogenous T cell receptor repertoire remained intact. In this regard, the DCOne stimulation acted synergistically with the anti-tumor specificity of the recombinant chimeric antigen receptor (CAR) of the CAR-T cell, resulting in improved tumor control, increased functionality and increased viability of the CAR-Ts. Accordingly, the methods of the disclosure address one of the main bottlenecks in CAR-T and other adoptive T cell therapies, namely the limited expansion capacity of T cells, particularly patient derived autologous T cells.

Example 4: DCOne Relapse Vaccination In Vivo has the Potential to Expand the Efficacy of CAR-T Therapies As noted herein, CAR-T therapy has the potency to bring cancer patients into remission. However, clinical responses are limited in duration as a result of the limited life span of CAR-T and other cell therapies. Any residual tumor tissue may therefore lead to relapse.

Figure 13:
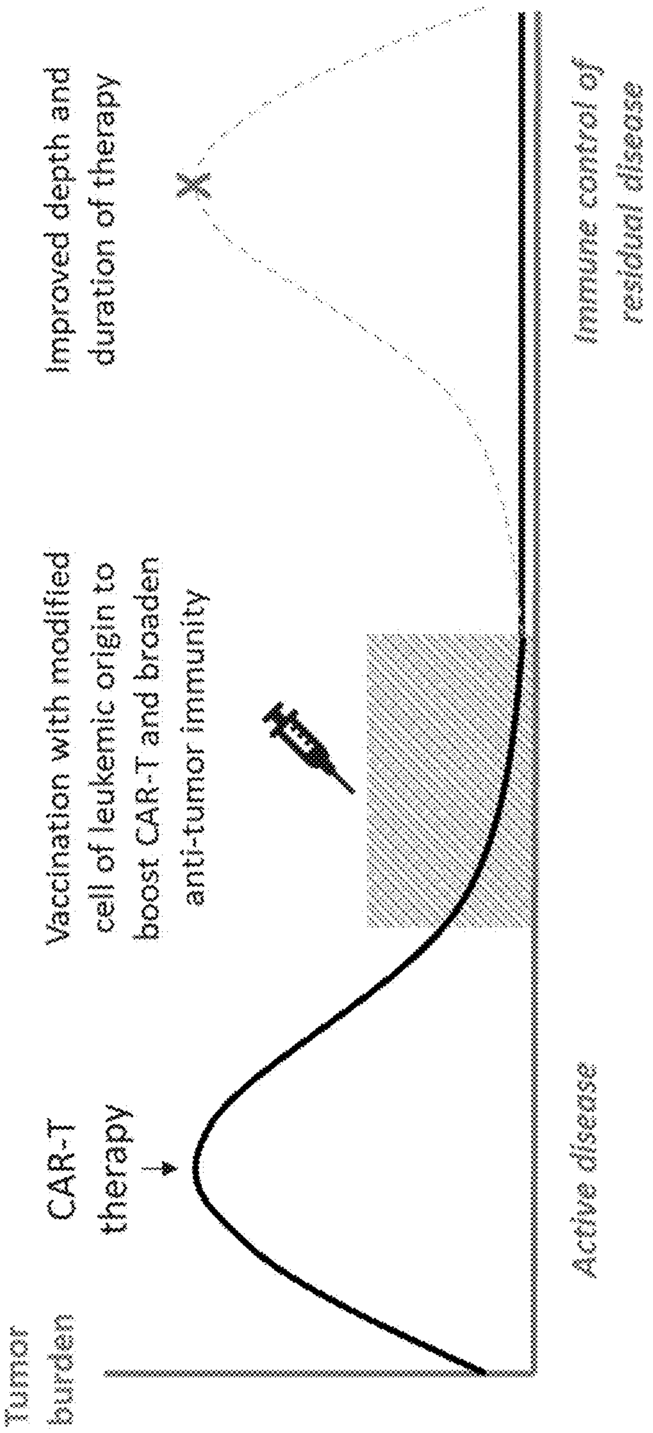
FIG. 13 depicts a graph showing the therapeutic rationale for combining DCP-001 and adoptive cell therapies in vivo.

FIG. 13 is a schematic showing that DCP-001 can also be used as a relapse vaccine in vivo to prolong the clinical response to CAR-T therapies. For example, exposure of CAR-T therapies to DCP-001 can improve CAR-T function and survival, build immunological memory or boost broader immune control over residual disease. In another example, vaccination with a modified cell of leukemic origin (e.g., DCP-001) can deepen and extend clinical responses to CAR-T therapies and broaden anti-tumor immunity. Thus, DCP-001 can be combined with CAR-T therapy to obtain synergistic results.

Example 5: Generation of Foreign Antigen-Specific T Cells to Boost Tumor-Antigen-Independent Anti-Tumor Responses Due to unavailability of research-grade off-the-shelf engineered T cells expressing foreign antigen specific TCR or CAR-T cells with specificity for foreign-antigen, a CMV-specific T cell clone was used as a tool to address the efficacy of foreign-antigen specific T cell to induce effector T cell responses against tumors labelled with foreign antigen.

Materials and Methods

Coupling CRM197 with CMVpp65 495-503 (FITC-NLVPMVATV-GGC):

The CMVpp65 495-503 peptide has a C-terminal GGC, and an N-terminal FITC. Coupling to CRM197-Maleimide occurs via free-cysteine. Different conditions were assessed for optimal coupling, as well as different ratios of CRM197-Maleimide and CMVpp65 peptide. After coupling, size exclusion chromatography using a Sephadex G25M column was performed to separate the coupled CRM197-FITC-NLVPMVATV-GGC from uncoupled FITC-NLVPMVATV. Coupling QC was monitored via Western Blot.

Killing of HLA-A2+ Tumor Cells Marked with CRM197-CMVpp65 Peptide by CMVpp65 T Cell Clone:

Tumor killing was assessed by culturing a CMVpp65 T cell clone with tumor cells at 5:1 E:T ratio.

The killing of tumor cells by activated CMVpp65 specific T cells was evaluated after 60 minutes of incubation time using the GranToxiLux assay (OncoImmunin). This assay visualized the active amount of the cytolytic enzyme Granzyme B (GrzB) inside the tumor cells; the binding of a fluorochrome-labelled substrate (TFL4) to active GrzB in tumor cells was visualized by flow cytometry. Tumor target cells labelled with TFL4 and incubated in the absence of CMVpp65 specific T cells served as negative controls.

Assessment of CD107a expression, marker for CD8 T cell degranulation, a prerequisite for cytolysis, was performed using flow cytometry. Flow cytometric analysis was performed using a BD FACSVerse. Data was analyzed using FlowJo (BD Biosciences).

Experiments

DCOne mDC Mediated Internalization of CMVpp65 Antigen Coupled to CRM197

Figure 14:
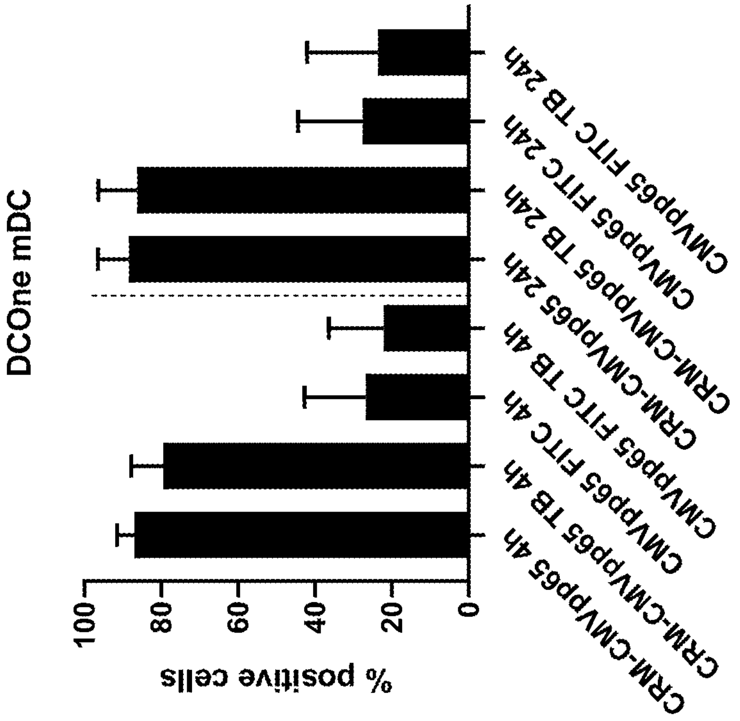
FIG. 14 is a plot showing the percent uptake in DCOne mDC cells of CMVpp65-FITC or CRM197-CMVpp65-FITC peptides.

DCOne mDCs were cultured and loaded with CMVpp65-FITC or CRM197-CMVpp65-FITC peptides for 4 hours and 24 hours. The cells were harvested washed and, assessed by flow cytometry, with or without Trypan blue (TB). Trypan blue quenches the extracellular binding of antigens and allows for the distinguishing between surface-bound and internalized antigens. FIG. 14 is a plot showing the percent uptake in DCOne mDC cells of CMVpp65-FITC or CRM197-CMVpp65-FITC peptides. Without being bound to any theory, the HB-EGF receptor on DCOne mDCs facilitated uptake of CMVpp65 peptides via conjugated CRM197 ligand.

Figure 15:
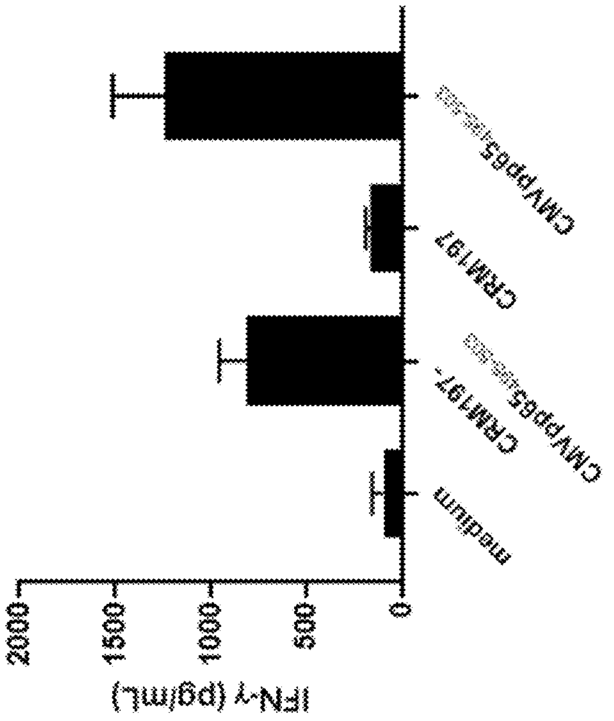
FIG. 15 is a plot showing the level of IFN-γ detected in the media of DCOne mDCs loaded as indicated.

DCOne mDC Mediated Processing and Presentation of CRM197-CMVpp65 to CMVpp65-Specific T Cells Clone:

DCOne mDC was cultured and loaded with CRM197-CMVpp65 conjugate, CRM197, or CMVpp65 short peptide (SP) for 5 hours. After loading, the loaded DCOne mDCs were co-incubated with CMVpp65-T cells for 24 hours and IFN-γ secreted in the medium was assessed by ELISA. FIG. 15 is a plot showing the level of IFN-γ detected in the media of DCOne mDCs loaded as indicated.

Internalization of CMVpp65 Antigen Coupled to CRM197 by Tumor Cell Lines

Figure 16B:
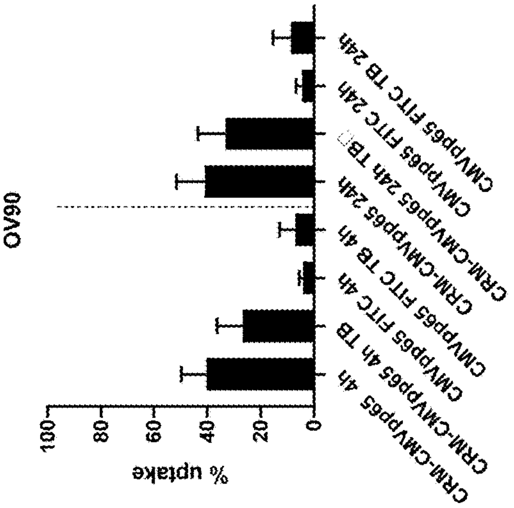
FIGS. 16A-16C are plots showing the percent uptake of CMVpp65-FITC or CRM197-CMVpp65-FITC peptides in OVCAR3 (FIG. 16A), OV90 (FIG. 16B), and U87MG (FIG. 16C) cells.
Figure 16A:
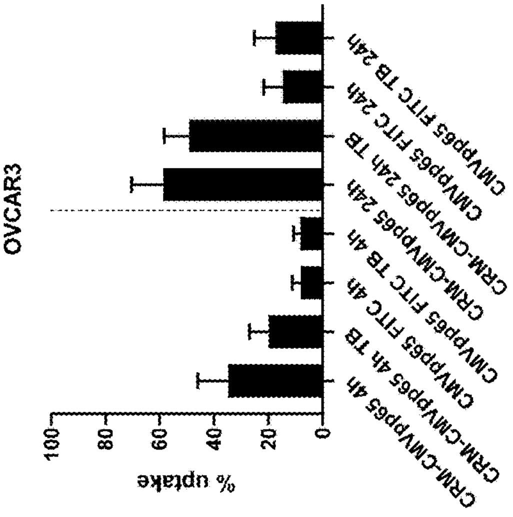
Figure 16C:
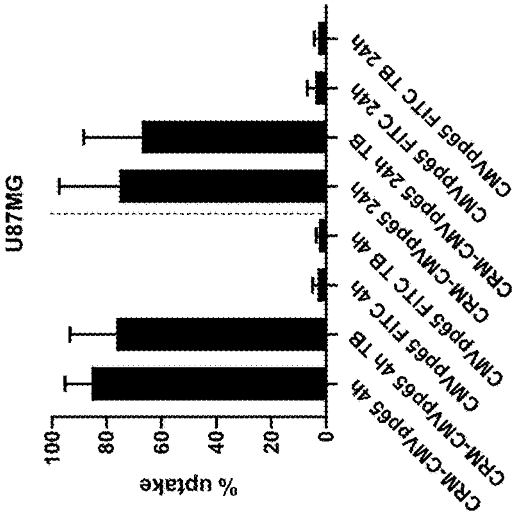

Efficiency in labeling of various tumor cells, including OVCAR3, OV90, and U87MG cells, was assessed by incubating the various tumor cells with CMVpp65-FITC peptides and CRM197-CMVpp65-FITC peptides for 4 hours and 24 hours. The cells were harvested washed and, assessed by flow cytometry, with or without Trypan blue (TB). FIGS. 16A-16C are plots showing the percent uptake of CMVpp65-FITC or CRM197-CMVpp65-FITC peptides in OVCAR3 (FIG. 16A), OV90 (FIG. 16B), and U87MG (FIG. 16C) cells.

Figure 17A:
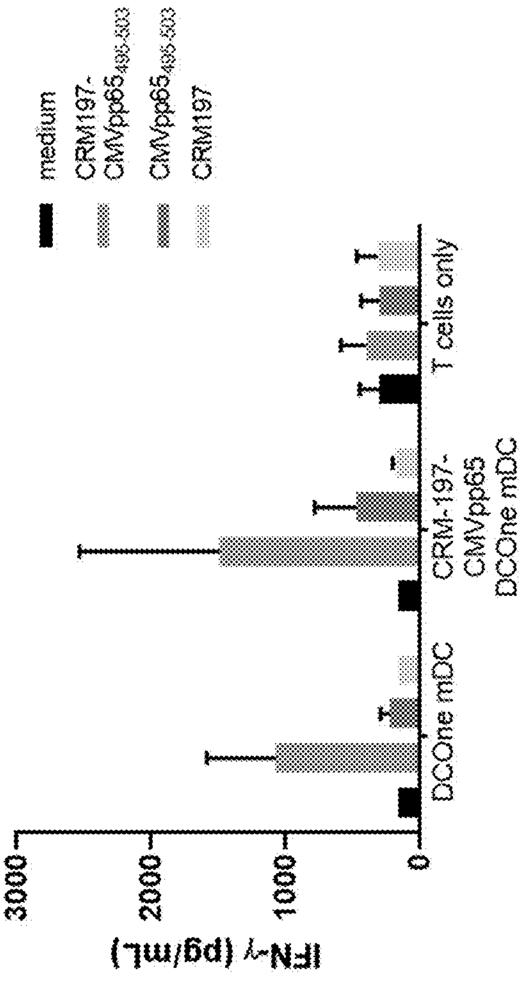
FIGS. 17A-17C are plots showing a CMVpp65 T cell clone stimulated with or without CRM-CMVpp65 conjugate-pulsed DCOne mDC incubated with HLA-A2+U87-MG tumor cells marked with CRM197-CMVpp65 conjugate/peptide at 5:1 effector:target (E:T) ratio, and effector cytokine IFN-γ analyzed in the supernatants by ELISA (FIG. 17A). Stimulation of CMVpp65-specific CD8 T cells by tumor cells marked with CMVpp65 peptide lead to an increase in CD107a expression (FIG. 17B) and lysis of the tumor cells (FIG. 17C).

Evaluation of the Cytotoxic Ability of CMVpp65 T Cell Clone to Kill HLA-A2+Tumor Cells Marked with CRM197-CMVpp65 Conjugate/Peptide:

To study the cytotoxic capacity of a foreign antigen specific-T cell, CMVpp65 T cell clone stimulated with or without CRM-CMVpp65 conjugate pulsed DCOne mDC is incubated with HLA-A2+ U87-MG tumor cells marked with CRM197-CMVpp65 conjugate/peptide at 5:1 effector:target (E:T) ratio and effector cytokine IFN-γ is analyzed in the supernatants by ELISA (FIG. 17A)

Figure 17B:
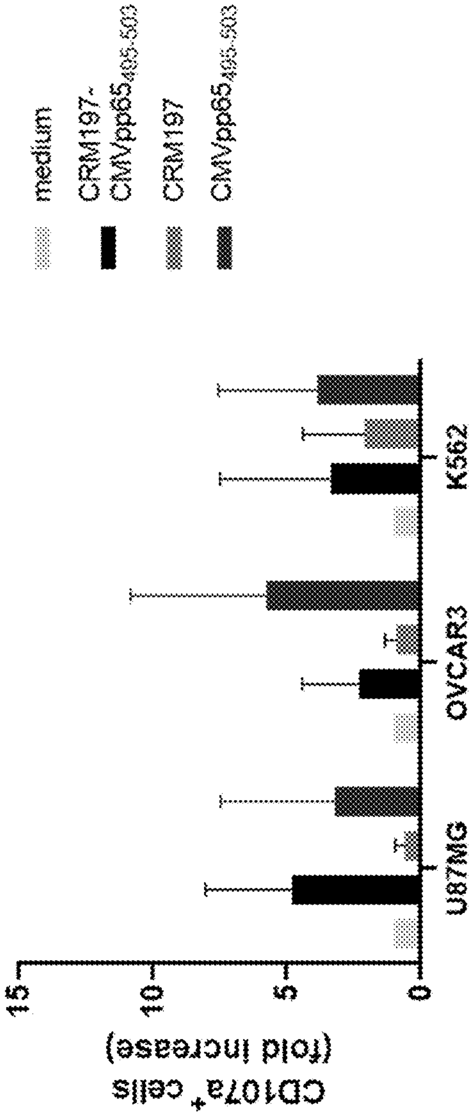

In another experiment, it was found that stimulation of CMVpp65-specific CD8+ T cells by tumor cell lines marked with CMVpp65 peptide resulted in an increase in CD107a expression (FIG. 17B). CMVpp65-specific CD8+ T cells were cultured in the presence or absence of CRM197-CMVpp65 peptide conjugate loaded tumor cell lines for 24 hours and subsequently analysed for intracellular cytolytic granules by measuring expression of CD107a using flow cytometry. The HLA deficient cell line K562 served as negative control. In FIG. 17B, the data presented is in fold increase compared to medium control. Data is presented as mean±SEM from 3-4 independent experiments.

To assay tumor cell killing, three different tumor cell lines were loaded overnight with the CRM197-CMVpp65 peptide conjugate. The killing of tumor cells by activated CMVpp65 specific T cells were evaluated after 60 minutes of incubation time using the GranToxiLux assay (OncoImmunin). This assay visualized the active amount of the cytolytic enzyme Granzyme B (GrzB) inside the tumor cells; and the binding of a fluorochrome-labelled substrate (TFL4) to active GrzB in tumor cells is visualized by flow cytometry.

Figure 17C:
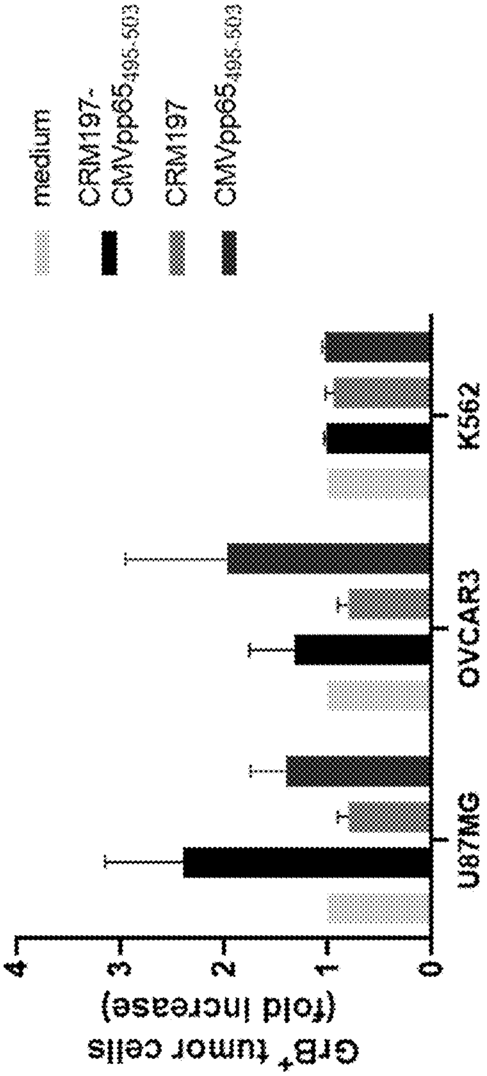

Tumor cells lines were labeled with fluorescent cell linker dye TFL4 and co-incubated with CMVpp65-specific CD8+ T cells for 1 hour at an effector:target ratio of 5:1 in the presence of fluorogenic granzyme B substrate. As shown in FIG. 17C, co-incubation with CMVpp65-specific CD8+ T cells resulted in increased detection of fluorescence in the tumor, as detected by multichannel flow cytometry. Fluorogenic Granzyme B activity in the target tumor cells after cleavage of the granzyme B substrate was measured by using the GranToxiLux™ kit (OncoImmunin, Inc., MD). The HLA deficient cell line K562 served as negative control. In FIG. 17C, the data presented is in fold increase compared to medium control. Data is presented as mean±SD from 4 independent experiments.

What is claimed is:

1. A method for generating a population of modified autologous T cells with enhanced activation status, comprising:

(a) obtaining a population of autologous T cells from a patient suffering from a cancer, wherein the population of autologous T cells have been modified to express a chimeric antigen receptor (CAR) which binds a tumor antigen in the patient;

(b) contacting the population of modified autologous T cells with a modified cell of leukemic origin, wherein the modified cell of leukemic origin comprises a mature dendritic cell phenotype and is non-proliferating; and (c) co-culturing the population of modified autologous T cells with the modified cell of leukemic origin under conditions suitable to stimulate proliferation of the modified autologous T cells, thereby generating the population of modified autologous T cells with enhanced activation status;

wherein the method results in multiplying the population of modified autologous T cells by at least 10 fold; and wherein the population of modified autologous T cells comprise both CD4+ and CD8+ cells, and the method results in an increased ratio of CD4+ to CD8+ cells.

2. The method of claim 1, wherein:

the method is for treating the patient suffering from the cancer, the method further comprising administering the population of modified autologous cells with enhanced activation status to the patient suffering from the cancer.

3. The method of claim 1, wherein the increased ratio of CD4+ to CD8+ cells is between at or about 1:5 and at or about 5:1.

4. The method of claim 1, wherein the increased ratio of CD4+ to CD8+ cells is between at or about 1:3 and at or about 3:1.

5. The method of claim 1, wherein modified cell of leukemic origin is CD40-positive, CD80-positive, and CD86-positive.

6. The method of claim 1, wherein the modified cell of leukemic origin comprises a CD70 costimulatory molecule.

7. The method of claim 1, where the modified cell of leukemic origin is a cell derived from cell line DCOne as deposited under the conditions of the Budapest treaty with the DSMZ under accession number DSMZ ACC3189 on 15 Nov. 2012.

8. A method for generating and expanding a population of modified autologous T cells comprising anti-tumor antigen specificity, comprising:

(a) obtaining a population of autologous T cells from a human patient suffering from a cancer, wherein the population of autologous T cells have been modified to express a chimeric antigen receptor (CAR) which binds a tumor antigen on a tumor cell in the patient; and (b) co-culturing the population of modified autologous T cells with a modified cell of leukemic origin under conditions suitable to expand and stimulate the population of modified autologous T cells, thereby generating and expanding the population of modified autologous T cells comprising anti-tumor antigen specificity, wherein the modified cell of leukemic origin comprises a mature dendritic cell phenotype and is non-proliferating, wherein the method results in multiplying the population of modified autologous T cells by at least 10 fold; and wherein the population of modified autologous T cells comprise both CD4+ and CD8+ cells, and the method results in an increased ratio of CD4+ to CD8+ cells.

9. The method of claim 8, wherein:

the modified cell of leukemic origin comprises an exogenous antigen or peptide fragments of the exogenous antigen, wherein the exogenous antigen is a tumor-associated antigen (TAA) or non-tumor-associated antigen, optionally, wherein the exogenous antigen is the same or different from the antigen to which the CAR binds;

wherein the modified cell of leukemic origin is loaded with the exogenous antigen or peptide fragments thereof prior to its exhibiting a mature dendritic cell phenotype, during transition of the modified cell of leukemic origin to a mature dendritic cell phenotype, or after the modified cell of leukemic origin exhibits a mature dendritic cell phenotype.

10. The method of claim 9, wherein the population of modified autologous T cells targets the exogenous antigen of the modified cell of leukemic origin.

11. The method of claim 9, wherein the population of modified autologous T cells targets the exogenous antigen of the modified cell of leukemic origin and is cross-reactive with non-tumor derived antigens displayed by the modified cell of leukemic origin.

12. The method of claim 8, wherein:

the population of autologous T cells comprises non-stimulated T cells.

13. The method of claim 8, wherein the CAR comprises an antigen binding domain, a transmembrane domain, and an intracellular domain comprising a costimulatory domain and a primary signaling domain.

14. The method of claim 13, wherein:

the transmembrane domain is selected from the group consisting of an artificial hydrophobic sequence, a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), ICOS (CD278), or CD154, and a transmembrane domain derived from a killer immunoglobulin-like receptor (KIR); and/or the intracellular domain comprises a costimulatory signaling domain and an intracellular signaling domain.

15. The method of claim 14, wherein:

the costimulatory signaling domain comprises a costimulatory domain of a protein selected from proteins in the TNFR superfamily, CD27, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS (CD278), NKG2C, B7-H3 (CD276), and an intracellular domain derived from a killer immunoglobulin-like receptor (KIR), or a variant thereof; and/or the intracellular signaling domain comprises an intracellular domain selected from cytoplasmic signaling domains of a human CD3 zeta chain (CD3ζ), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof.

16. A method for treating a disease or disorder, and/or a tumor in a subject in need thereof, comprising administering to the subject the plurality of modified autologous T cells generated and expanded by the method of claim 8.

17. The method of claim 16, wherein the disease or disorder is a cancer, and wherein the cancer comprises a liquid tumor or a solid tumor.

18. The method of claim 8, wherein the modified cell of leukemic origin is CD34-positive, CD1a-positive, CD83-positive, and CD14-negative; and optionally wherein the modified cell of leukemic origin comprises at least one tumor antigen selected from the group consisting of WT-1, RHAMM, PRAME, MUC-1, p53, and Survivin.

19. The method of claim 8, wherein the modified cell of leukemic origin comprises a cell surface marker selected from the group consisting of DC-SIGN, Langerin, CD40, CD70, CD80, CD83, CD86, and any combination thereof.

20. The method of claim 8, wherein the increased ratio of CD4+ to CD8+ cells is between at or about 1:5 and at or about 5:1.

21. The method of claim 8, wherein the increased ratio of CD4+ to CD8+ cells is between at or about 1:3 and at or about 3:1.

22. The method of claim 8, wherein modified cell of leukemic origin is CD40-positive, CD80-positive, and CD86-positive.

23. The method of claim 8, wherein the modified cell of leukemic origin comprises a CD70 costimulatory molecule.

24. The method of claim 8, where the modified cell of leukemic origin is a cell derived from cell line DCOne as deposited under the conditions of the Budapest treaty with the DSMZ under accession number DSMZ ACC3189 on 15 Nov. 2012.

25. A method for expanding a population of modified immune cells, comprising:

(a) obtaining a population of modified immune cells, wherein the modified immune cells comprise a chimeric antigen receptor (CAR);

(b) contacting the population of modified immune cells with a modified cell of leukemic origin, wherein the modified cell of leukemic origin comprises a mature dendritic cell phenotype and is non-proliferating; and (c) co-culturing the population of modified immune cells with the modified cell of leukemic origin under conditions suitable to stimulate proliferation of the modified immune cells, thereby expanding the population of modified immune cells;

wherein the method results in multiplying the population of modified immune cells by at least 10 fold; and wherein the population of modified immune cells comprise both CD4+ and CD8+ T cells, and the method results in an increased ratio of CD4+ to CD8+ cells.

26. The method of claim 25, wherein the increased ratio of CD4+ to CD8+ cells is between at or about 1:5 and at or about 5:1.

27. The method of claim 26, wherein the increased ratio of CD4+ to CD8+ cells is between at or about 1:3 and at or about 3:1.

28. The method of claim 25, wherein modified cell of leukemic origin is CD40-positive, CD80-positive, and CD86-positive.

29. The method of claim 25, wherein the modified cell of leukemic origin comprises a CD70 costimulatory molecule.

30. The method of claim 25, where the modified cell of leukemic origin is a cell derived from cell line DCOne as deposited under the conditions of the Budapest treaty with the DSMZ under accession number DSMZ ACC3189 on 15 Nov. 2012.

* * * * *